(12) United States Patent
Benedini et al.

(10) Patent No.: US 8,101,658 B2
(45) Date of Patent: Jan. 24, 2012

(54) NITRIC OXIDE DONATING PROSTAMIDES

(75) Inventors: Francesca Benedini, San Donato Milanese (IT); Stefano Biondi, Pero (IT); Valerio Chiroli, Milan (IT); Wesley Kwan Mung Chong, Encinitas, CA (US); Liming Dong, San Diego, CA (US); Achim Hans-Peter Krauss, San Marcos, CA (US); Fabio Nicoli, Milan (IT); Ganesh Prasanna, San Diego, CA (US); William Francois Vernier, San Diego, CA (US); Yi Yang, San Diego, CA (US)

(73) Assignee: Nicox S.A., Sophia Antipolis-Valbonne (FR)

( * ) Notice: Subject to any disclaimer, the term of this patent is extended or adjusted under 35 U.S.C. 154(b) by 0 days.

(21) Appl. No.: 12/991,855

(22) PCT Filed: May 11, 2009

(86) PCT No.: PCT/IB2009/005594
§ 371 (c)(1),
(2), (4) Date: Nov. 9, 2010

(87) PCT Pub. No.: WO2009/136281
PCT Pub. Date: Nov. 12, 2009

(65) Prior Publication Data
US 2011/0092590 A1 Apr. 21, 2011

Related U.S. Application Data

(60) Provisional application No. 61/139,333, filed on Dec. 19, 2008, provisional application No. 61/052,084, filed on May 9, 2008.

(51) Int. Cl.
*A61K 31/04* (2006.01)
*A61K 31/16* (2006.01)
*C07C 203/04* (2006.01)
*C07C 291/00* (2006.01)
(52) U.S. Cl. ........................................ 514/509; 558/482
(58) Field of Classification Search .................... None
See application file for complete search history.

(56) References Cited

U.S. PATENT DOCUMENTS 7,718,656 B2 * 5/2010 Benedini et al. .......... 514/252.12
2007/0015838 A1 * 1/2007 Voet ............................. 514/622

FOREIGN PATENT DOCUMENTS

WO WO 02/096432 * 12/2002
WO WO-2007/000641 A2 1/2007

* cited by examiner

*Primary Examiner* — Fiona T Powers
(74) *Attorney, Agent, or Firm* — Arent Fox LLP

(57) ABSTRACT

Nitroderivatives of prostaglandins having improved pharmacological activity and enhanced tolerability are described. They can be employed for the treatment of glaucoma and ocular hypertension.

19 Claims, 1 Drawing Sheet

NITRIC OXIDE DONATING PROSTAMIDES

CROSS-REFERENCE TO RELATED APPLICATION

This application is a National Stage entry of International Application No. PCT/IB2009/005594, filed May 11, 2009, which claims priority to Provisional Application No. 61/052,084, filed May 9, 2008, and Provisional Application No. 61/139,333 filed Dec. 19, 2008 the disclosure of the prior applications are hereby incorporated in their entirety by reference.

BACKGROUND OF THE INVENTION

The present invention relates to new prostaglandin derivatives. More particularly, the present invention relates to nitrooxyderivatives of prostaglandin amides (also known as prostamides), pharmaceutical compositions containing them and their use as drugs for treating glaucoma and ocular hypertension.

Glaucoma is a disease of the eye characterized by a progressive loss of visual field due to irreversible damage to the optic nerve to the point where, if untreated, may result in total blindness. Glaucoma occurs when an imbalance in production and drainage of fluid in the eye (aqueous humor) increases eye pressure to unhealthy levels. The chief pathophysiological feature of glaucoma is raised intraocular pressure (IOP). The loss of visual field, in one form of primary open angle glaucoma (POAG), is associated with a sustained increase in the intraocular pressure of the diseased eye. Moreover, elevated intraocular pressure without visual field loss is thought to be indicative of the early stages of this form of POAG.

It is known that elevated IOP can be at least partially controlled by administering drugs which either reduce the production of aqueous humor within the eye or increase the fluid drainage, such as beta-blockers, α-agonists, cholinergic agents, carbonic anhydrase inhibitors, or prostaglandin analogs.

Several side effects are associated with the drugs conventionally used to treat glaucoma. Topical beta-blockers show serious pulmonary side effects, depression, fatigue, confusion, impotence, hair loss, heart failure and bradycardia. Topical α-agonists have a fairly high incidence of allergic or toxic reactions; topical cholinergic agents (miotics) can cause visual side effects.

Topical prostaglandin analogs (bimatoprost, latanoprost, travoprost and unoprostone) used in the treatment of glaucoma can produce ocular side effects, such as increased pigmentation of the iris, ocular irritation, conjunctival hyperaemia, iritis, uveitis and macular oedema (Martindale, Thirty-third edition, p. 1445).

U.S. Pat. No. 3,922,293 describes monocarboxyacylates of prostaglandins F-type and their 15β isomers, at the C-9 position, and processes for preparing them; U.S. Pat. No. 6,417,228 discloses 13-aza prostaglandins having functional $PGF_{2\alpha}$ receptor agonist activity and their use in treating glaucoma and ocular hypertension.

WO90/02553 discloses the use of prostaglandin derivatives of PGA, PGB, PGE and PGF, in which the omega chain contains a ring structure, for the treatment of glaucoma or ocular hypertension.

WO00/51978 describes novel nitrosated and/or nitrosylated prostaglandins, in particular novel derivatives of $PGE_1$, novel compositions and their use for treating sexual dysfunctions.

U.S. Pat. No. 5,625,083 discloses dinitroglycerol esters of prostaglandins which may be used as vasodilators, antihypertensive cardiovascular agents or bronchodilators.

U.S. Pat. No. 6,211,233 discloses compounds of the general formula $A\text{-}X_1\text{—}NO_2$, wherein A contains a prostaglandin residue, in particular $PGE_1$, and $X_1$ is a bivalent connecting bridge, and their use for treating impotence.

FIELD OF THE INVENTION

It is an object of the present invention to provide new derivatives of prostaglandins able not only to eliminate or at least reduce the side effects associated with these compounds, but also to possess an improved pharmacological activity. It has been surprisingly found that certain prostaglandin nitroderivatives have an improved IOP-reducing efficacy and an improved overall profile as compared to the known prostaglandin analogs both in terms of broad range of therapeutic applicability for the treatment of eye diseases and of enhanced activity and tolerability. In particular, it has been recognized that the prostaglandin nitroderivatives of the present invention can be employed for treating glaucoma and ocular hypertension. The compounds of the present invention are indicated for the reduction of intraocular pressure in patients with open-angle glaucoma or with chronic angle-closure glaucoma who underwent peripheral iridotomy or laser iridoplasty.

SUMMARY OF THE INVENTION

An object of the present invention is, therefore, a compound of formula (I):

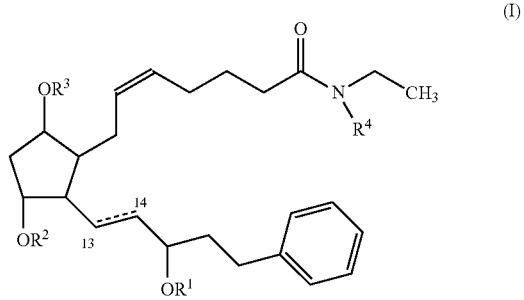

wherein the symbol ⚌ represents a single or double bond in the cis or trans configuration; $R^1$, $R^2$, $R^3$ and $R^4$ are each independently H, —C(O)$R^5$—$ONO_2$, —C(O)O$R^5$—$ONO_2$, —C(O)$R^5R^6$—$ONO_2$, —[C(O)$R^5$]$_m$—$ONO_2$, —C(O)$R^5$—[OC(O)$R^6$]$_n$—$ONO_2$, —C(O)$R^5$—[(O)C$R^6$]$_n$—$ONO_2$, —C(O)$R^5$—[(O)$R^6$]$_n$—$ONO_2$, —[C(O)$R_5$]$_m$—[C(O)O$R_6$]$_n$—$ONO_2$, with the proviso that $R^1$, $R^2$, $R^3$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, $NO_2$ or $ONO_2$; each m is independently selected from 1 to 6; and each n is independently selected from 1 to 6;
or a pharmaceutically acceptable salt or stereoisomer thereof.

In another aspect of the invention, there is provided a compound of formula (I) wherein at least two of $R_1$, $R_2$, $R_3$ and $R_4$ are H, or wherein $R_1$ and $R_2$ are both H, or wherein $R_1$, $R_2$ and $R_3$ are H, or wherein the bond between the carbon atoms in positions 13 and 14 is a double bond.

In another aspect of the invention, there is provided a compound of formula (I) wherein $R_1$ and $R_2$ are both H and the bond between the carbon atoms in positions 13 and 14 is a double bond, or wherein $R_1$, $R_2$ and $R_3$ are H and the bond between the carbon atoms in positions 13 and 14 is a double bond.

In a further aspect of the invention, there is provided a compound of formula (II):

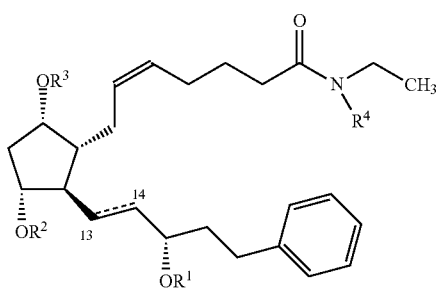

(II)

wherein the symbol $\rightleftharpoons$ represents a single or double bond in the cis or trans configuration; $R^1$, $R^2$, $R^3$ and $R^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^1$, $R^2$, $R^3$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; and each n is independently selected from 1 to 6;

or a pharmaceutically acceptable salt or stereoisomer thereof.

In yet another aspect of the invention, there is provided a compound of formula (II) wherein at least two of $R^1$, $R^2$, $R^3$ and $R^4$ are H, or wherein $R^1$ and $R^2$ are both H, or wherein $R^2$, $R^3$ and $R^4$ are H.

In still another aspect of the invention, there is provided a compound of formula (II) wherein the bond between the carbon atoms in positions 13 and 14 is a single bond or a double bond.

In yet another aspect of the invention, there is provided a compound of formula (II) wherein $R^1$, $R^3$ and $R^4$ are H, and the bond between the carbon atoms in positions 13 and 14 is a single bond.

In another aspect of the invention, there is provided a compound of formula (II) wherein $R^2$, $R^3$ and $R^4$ are H, and the bond between the carbon atoms in positions 13 and 14 is a single bond.

In another aspect of the invention, there is provided a compound of formula (III):

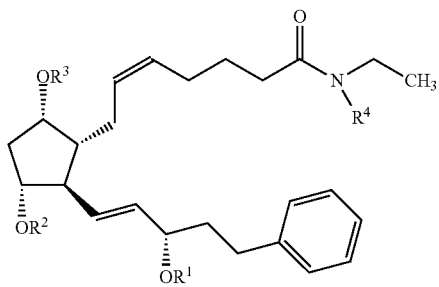

(III)

wherein $R^1$, $R^2$, $R^3$ and $R^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^1$, $R^2$, $R^3$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; and each n is independently selected from 1 to 6; or a pharmaceutically acceptable salt or stereoisomer thereof.

In a further aspect of the invention, there is provided a compound of formula (III) wherein at least two of $R^1$, $R^2$, $R^3$ and $R^4$ are H.

In yet another aspect of the invention, there is provided a compound of formula (IV):

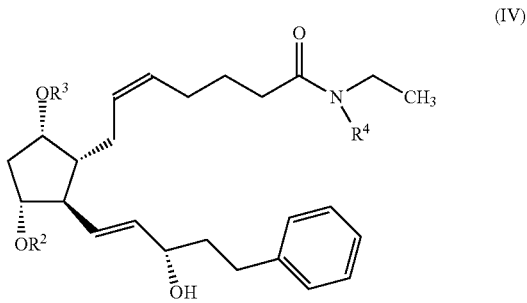

(IV)

wherein $R^2$, $R^3$ and $R^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^2$, $R^3$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; each n is independently selected from 1 to 6; or a pharmaceutically acceptable salt or stereoisomer thereof.

In another aspect of the invention, there is provided a compound of formula (IV) wherein at least two of $R^2$, $R^3$ and $R^4$ are H.

In a further aspect of the invention, there is provided a compound of formula (V):

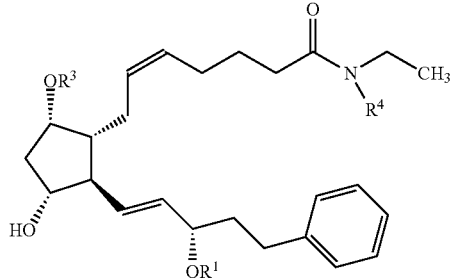

(V)

wherein $R^1$, $R^3$ and $R^4$ are each independently H, —C(O)$R^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^1$, $R^3$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; each n is independently selected from 1 to 6; or a pharmaceutically acceptable salt or stereoisomer thereof.

In still another aspect of the invention, there is provided a compound of formula (V) wherein at least two of $R^1$, $R^3$ and $R^4$ are H, or wherein $R^1$ is H.

In yet another aspect of the invention, there is provided a compound of formula (VI):

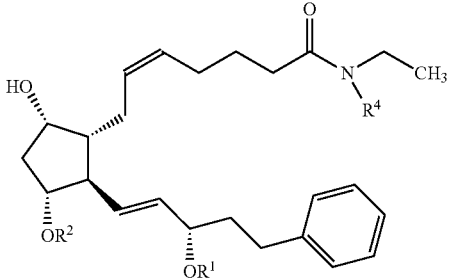

(VI)

wherein $R^1$, $R^2$ and $R^4$ are each independently H, —C(O)$R^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^1$, $R^2$ and $R^4$ cannot all be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; and each n is independently selected from 1 to 6; or a pharmaceutically acceptable salt or stereoisomer thereof.

In still another aspect of the invention, there is provided a compound of formula (VI) wherein at least two of $R^1$, $R^2$ and $R^4$ are H.

In a further aspect of the invention, there is provided a compound of formula (VII):

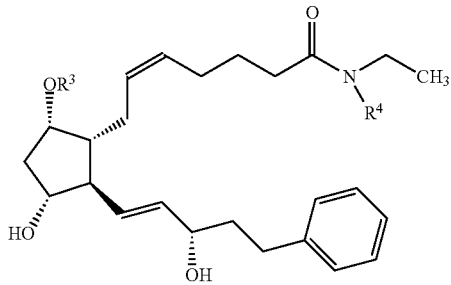

(VII)

wherein $R^3$ and $R^4$ are each independently H, —C(O)$R^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)R$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^3$ and $R^4$ cannot both be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$; each m is independently selected from 1 to 6; and each n is independently selected from 1 to 6; or a pharmaceutically acceptable salt or stereoisomer thereof.

In still another aspect of the invention, there is provided a compound of formula (VIII):

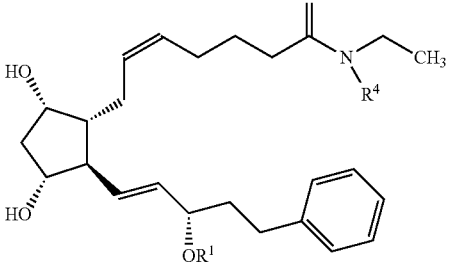

(VIII)

wherein $R^1$ and $R^4$ are each independently H, —C(O)$R^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$_6$]$_n$—ONO$_2$, with the proviso that $R^1$ and $R^4$ cannot both be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, $NO_2$ or $ONO_2$; each m is independently selected from 1 to 6; and each n is independently selected from 1 to 6; or a pharmaceutically acceptable salt or stereoisomer thereof.

In yet another aspect of the invention, there is provided a compound of formula (VIII) wherein $R^1$ is H.

In still another aspect of the invention, there is provided a compound of formula (IX):

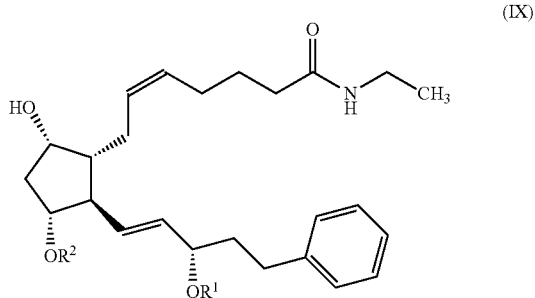

(IX)

wherein $R^1$ and $R^2$ are each independently H, —C(O)$R^5$—$ONO_2$, —C(O)O$R^5$—$ONO_2$, —C(O)$R^5R^6$—$ONO_2$, —[C(O)$R^5$]$_m$—$ONO_2$, —C(O)$R^5$—[OC(O)$R^6$]$_n$—$ONO_2$, —C(O)$R^5$—[(O)C$R^6$]$_n$—$ONO_2$, —C(O)$R^5$—[(O)$R^6$]$_n$—$ONO_2$, —[C(O)$R_5$]$_m$—[C(O)O$R_6$]$_n$—$ONO_2$, with the proviso that $R^1$ and $R^2$ cannot both be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, $NO_2$ or $ONO_2$; each m is independently selected from 1 to 6; and each n is independently selected from 1 to 6; or a pharmaceutically acceptable salt or stereoisomer thereof.

In still another aspect of the invention, there is provided a compound of formula (IX) wherein $R^1$ is H.

In a further aspect of the invention, there is provided a compound of formula (X):

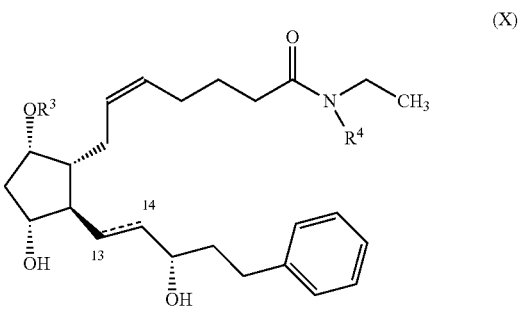

(X)

wherein the symbol ═ represents a single or double bond in the cis or trans configuration; $R^3$ and $R^4$ are each independently H, —C(O)$R^5$—$ONO_2$, —C(O)O$R^5$—$ONO_2$, —C(O)$R^5R^6$—$ONO_2$, —[C(O)$R^5$]$_m$—$ONO_2$, —C(O)$R^5$—[OC(O)$R^6$]$_n$—$ONO_2$, —C(O)$R^5$—[(O)C$R^6$]$_n$—$ONO_2$, —C(O)$R^5$—[(O)$R^6$]$_n$—$ONO_2$, —[C(O)$R_5$]$_m$—[C(O)O$R_6$]$_n$—$ONO_2$, with the proviso that $R^3$ and $R^4$ cannot both be H; each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic; wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, $NO_2$ or $ONO_2$; each m is independently selected from 1 to 6; and each n is independently selected from 1 to 6; or a pharmaceutically acceptable salt or stereoisomer thereof.

In still another aspect of the invention, there is provided a compound of formula (X) wherein the bond between the carbon atoms in positions 13 and 14 is a double bond.

In another aspect of the invention, there is provided a compound selected from the group consisting of:

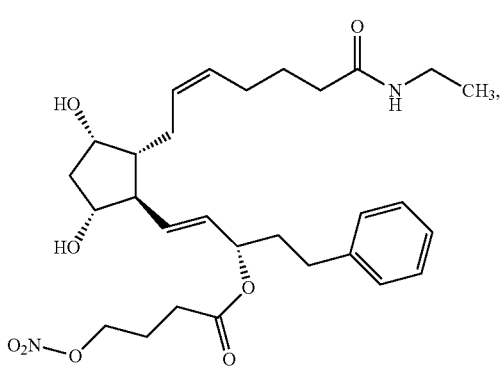

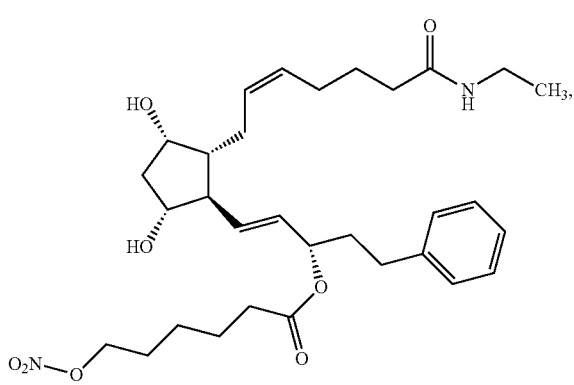

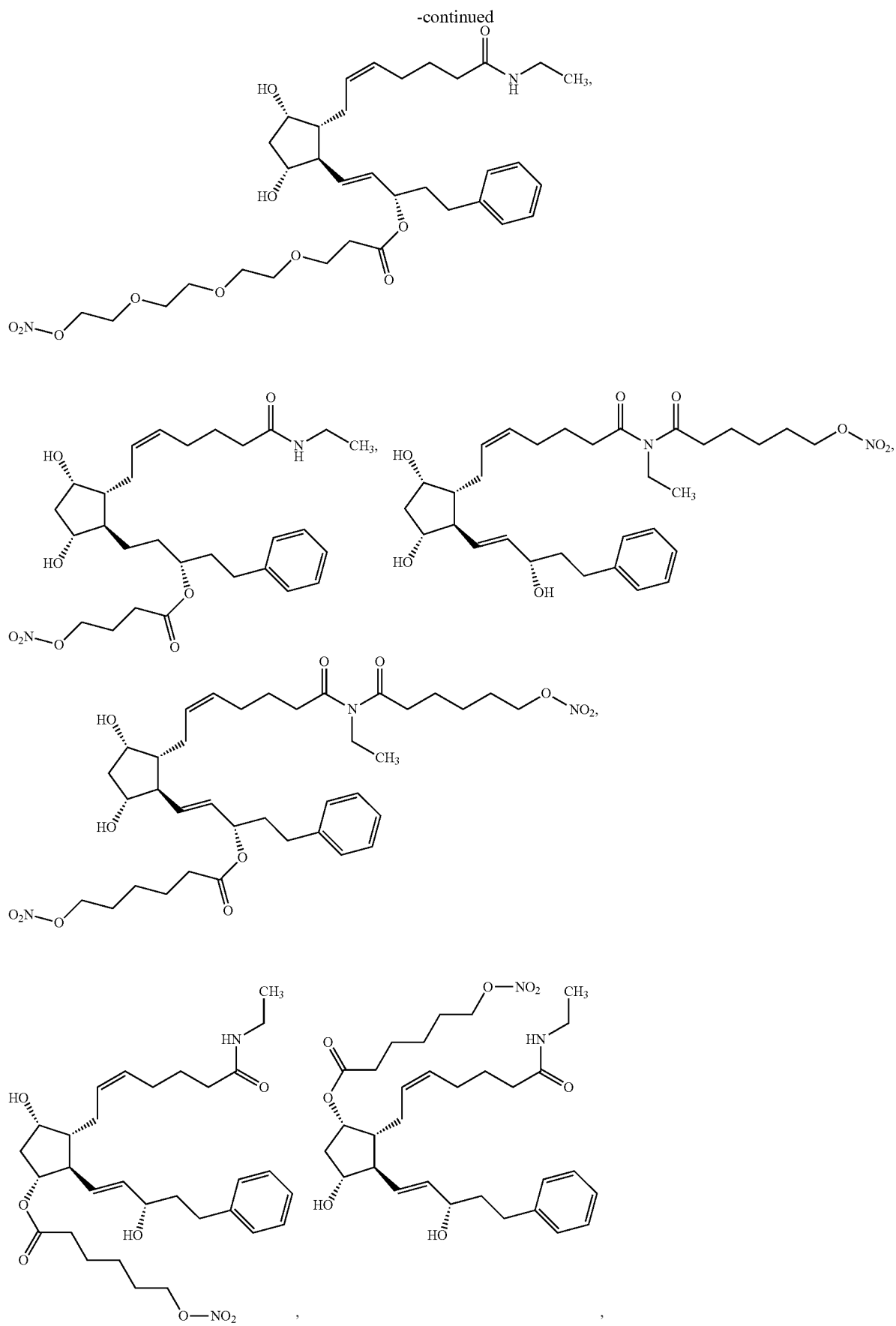

11
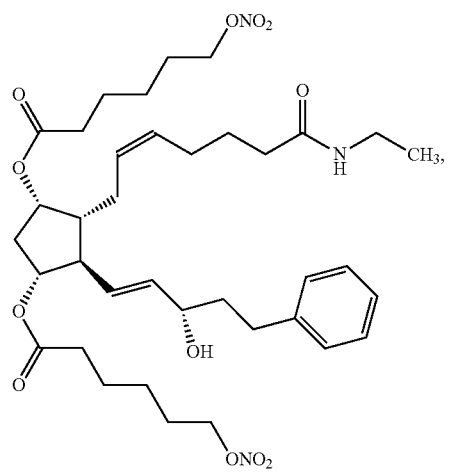
-continued
12
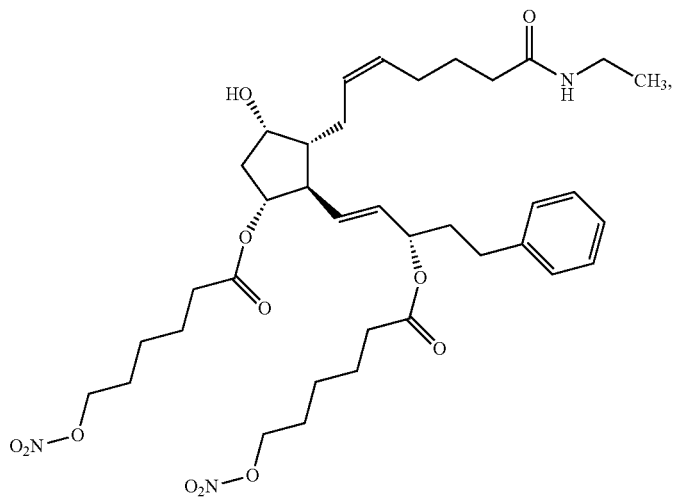
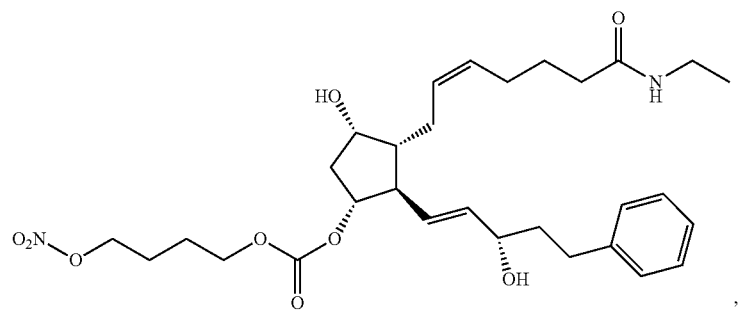
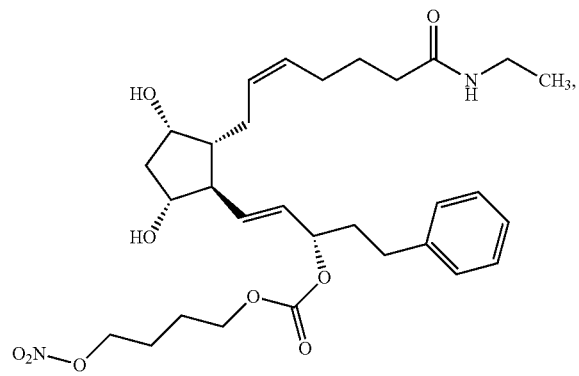
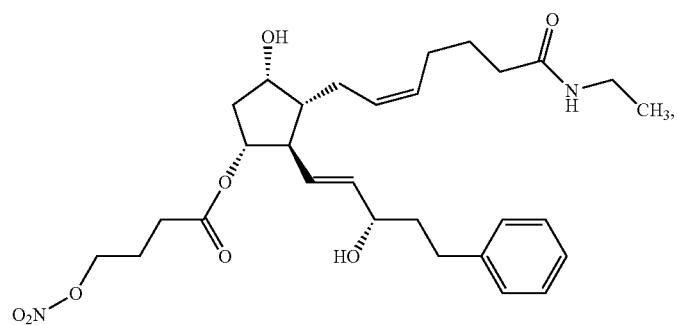

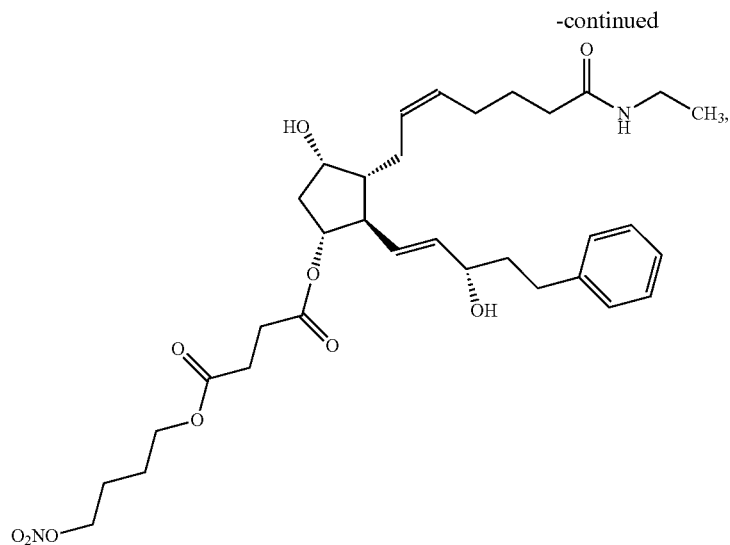
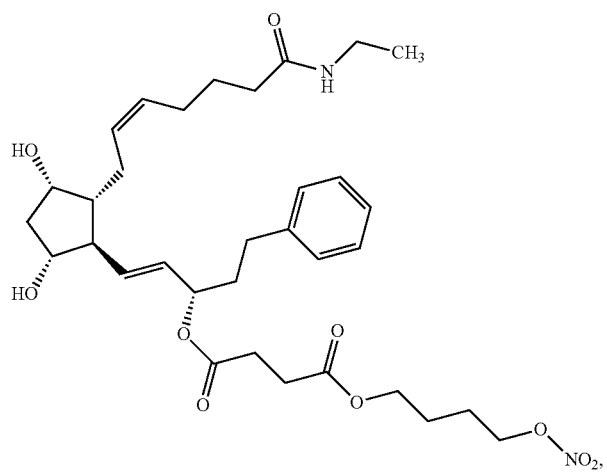
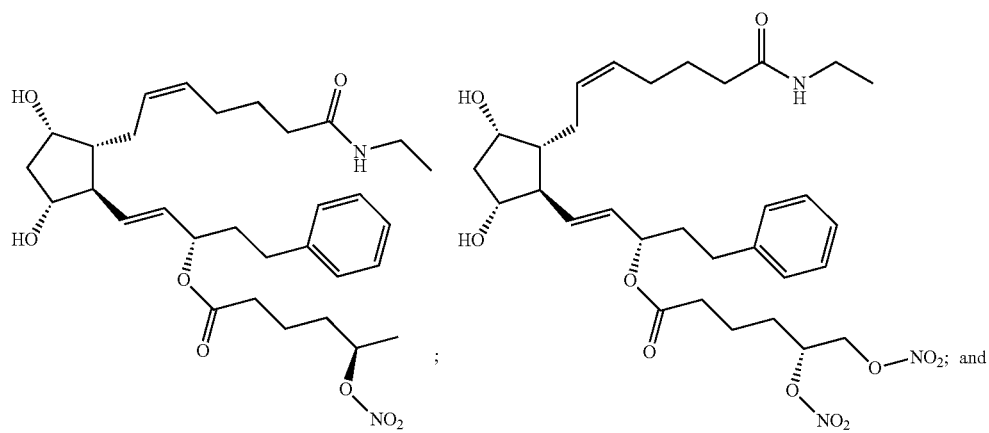

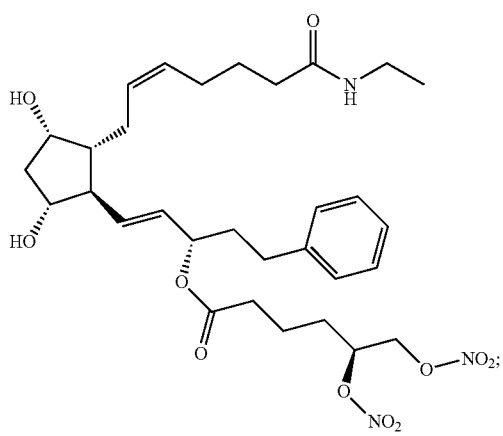

or a pharmaceutically acceptable salt or stereoisomer thereof.

In another aspect of the invention, there is provided a compound of any one of formula (I) to (X) for use as a medicament, or for the preparation of a medicament for treating glaucoma and ocular hypertension.

In yet another aspect of the invention, there is provided a pharmaceutical composition comprising a pharmaceutically acceptable carrier and a pharmaceutically effective amount of a compound of any one of formula (I) to (X) and/or a salt or stereoisomer thereof, or such a pharmaceutical composition in a suitable form for topical administration.

In still another aspect of the invention, there is provided a pharmaceutical composition as herein described for the treatment of glaucoma and ocular hypertension, or wherein the compound is administered as a solution, suspension or emulsion in an ophthalmically acceptable vehicle.

In a further aspect of the invention, there is provided a method for treating glaucoma or ocular hypertension comprising contacting an effective intraocular pressure reducing amount of a pharmaceutical composition as herein described with the eye in order to reduce eye pressure and to maintain said pressure on a reduced level.

In another aspect of the invention, there is provided a pharmaceutical composition comprising a mixture of a compound of any one of formula (I) to (X) and/or a salt or stereoisomer thereof as herein described and (i) a beta-blocker or (ii) a carbonic anhydrase inhibitor or (iii) an adrenergic agonist; or a nitrooxy derivative thereof.

DEFINITIONS

Figure 1:
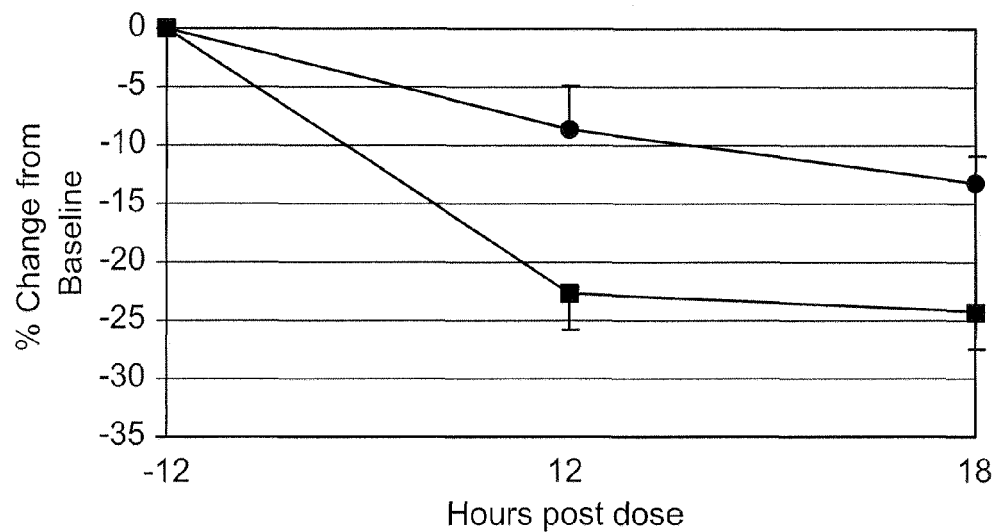
FIG. 1 is a graph illustrating the intraocular pressure response when administering an example compound and Bimatoprost to an ocular hypertensive primate in accordance with aspects of the present invention.

As used herein, the terms "comprising" and "including" are used in their open, non-limiting sense.

As used herein, the term "substituted," means that the specified group or moiety bears one or more substituents. The term "unsubstituted," means that the specified group bears no substituents.

As used herein, the term "optionally substituted" means that the specified group is unsubstituted or is substituted by one or more substituents.

As used herein, the terms "treat," "treating" or "treatment" includes preventative (e.g., prophylactic) and palliative treatment.

As used herein, the term "pharmaceutically acceptable" means the carrier, diluent, excipients and/or salt must be compatible with the other ingredients of the formulation and not deleterious to the recipient thereof.

As used herein, the term "alkyl" means a straight or branched chain saturated hydrocarbon. Exemplary alkyl groups include but are not limited to methyl, ethyl, propyl, isopropyl, n-butyl, sec-butyl, tert-butyl, pentyl, isopentyl, neopentyl, tert-pentyl, 1-methylbutyl, 2-methylbutyl, 3-methylbutyl, hexyl, isohexyl, heptyl, octyl and the like.

As used herein, the term "alkenyl" means a straight or branched chain hydrocarbon having at least one double bond, i.e., a C=C. Exemplary alkenyl groups include but are not limited to vinyl, propenyl, butenyl, pentenyl, hexenyl, heptenyl, octenyl and the like.

As used herein, the term "alkynyl" means a straight or branched chain hydrocarbon having at least one triple bond, i.e., a C≡C. Exemplary alkynyl groups include but are not limited to acetylenyl, propargyl, butynyl, pentynyl, hexynyl, heptynyl, octynyl and the like.

As used herein, the term "cycloalkyl" means a cyclic saturated hydrocarbon. Exemplary cycloalkyl groups include but are not limited to cyclopropyl, cyclobutyl, cyclopentyl, cyclohexyl, cycloheptyl, cyclooctyl and the like.

As used herein, the term "cycloalkenyl" means a cyclic hydrocarbon having at least one double bond, i.e., a C=C. Exemplary cycloalkenyl groups include but are not limited to cyclopropenyl, cyclobutenyl, cyclopentenyl, cyclohexenyl, cycloheptenyl, cyclooctenyl and the like.

As used herein, the term "cycloalkynyl" means a cyclic hydrocarbon having at least one triple bond, i.e., a C≡C. Exemplary cycloalkynyl groups include but are not limited to cyclohexynyl, cycloheptynyl, cyclooctynyl and the like.

As used herein, the term "alkoxy" means a straight or branched chain saturated alkyl group bonded through oxygen. Exemplary alkoxy groups include but are not limited to methoxy, ethoxy, propoxy, isopropoxy, butoxy, isobutoxy, tert-butoxy, pentoxy, isopentoxy, neopentoxy, tert-pentoxy, hexoxy, isohexoxy, heptoxy, octoxy and the like.

As used herein, the term "alkylene" means a straight chain or branched chain saturated hydrocarbon wherein a hydrogen atom is removed from each of the terminal carbons. Exemplary alkylene groups include but are not limited to methylene, ethylene, propylene, butylene, pentylene, hexylene, heptylene and the like.

As used herein, the term "halo" or "halogen" means fluoro, chloro, bromo or iodo.

As used herein, the terms "heterocyclic" and "heterocyclyl" mean an aromatic or non-aromatic cyclic group containing one to four heteroatoms each independently selected from O, S and N, wherein each group has from 3 to 10 atoms in its ring system. Non-aromatic heterocyclic groups include groups having only 3 atoms in their ring system, whereas aromatic heterocyclic groups have at least 5 atoms in their ring system. Heterocyclic groups include fused ring systems such as benzo-fused rings and the like. An exemplary 3 membered heterocyclic group is aziridine; 4 membered heterocyclic group is azetidinyl (derived from azetidine); 5 membered heterocyclic group is thiazolyl; 7 membered ring heterocyclic group is azepinyl; and a 10 membered heterocyclic group is quinolinyl.

Examples of non-aromatic heterocyclic groups include but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl.

Examples of aromatic heterocyclic (heteroaryl) groups include but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Heterocyclic groups may be optionally substituted on any ring carbon, sulfur or nitrogen atom(s) by one to two oxygens (oxo), per ring. An example of a heterocyclic group wherein 2 ring carbon atoms are substituted with oxo moieties is 1,1-dioxo-thiomorpholinyl.

Exemplary five to six membered heterocyclic aromatic rings having one or two heteroatoms selected independently from oxygen, nitrogen and sulfur include but are not limited to isothiazolyl, pyridinyl, pyridiazinyl, pyrimidinyl, pyrazinyl and the like.

Exemplary partially saturated, fully saturated or fully unsaturated five to eight membered heterocyclic rings having one to four heteroatoms selected independently from oxygen, sulfur and nitrogen include but are not limited to 3H-1,2-oxathiolyl, 1,2,3-oxadizaolyl, 1,2,4-oxadiazolyl, 1,2,5-oxadiazolyl and the like. Further exemplary five membered rings are furyl, thienyl, 2H-pyrrolyl, 3H-pyrroyl, pyrrolyl, 2-pyrrolinyl, 3-pyrrolinyl, pyrrolidinyl, 1,3-dioxolanyl, oxazolyl, thiazolyl, thiazolyl, imidazolyl, 2H-imidazolyl, 2-imidazolinyl, imidazolidinyl, pyrazolyl, 2-pyrazolinyl, pyrazolinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4-oxadiazolyl, 1,2,3-triazolyl, 1,2,4-trizaolyl, 1,3,4-thiadiazolyl, 1,2,3,4-oxatriazolyl, 1,2,3,5-oxatrizaolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl. Further exemplary six member rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-trizainyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings are azepinyl, oxepinyl, thiepinyl and 1,2,4-diazepinyl. Further exemplary eight membered rings are cyclooctyl, cyclooctenyl and cyclooctadienyl.

Exemplary 3-10 membered heterocyclyl groups include but are not limited to oxetane, azetidine, tetrahydrofuran, pyrrolidine, 2,5-dihydro-1H-pyrrole, 1,3-dioxalane, isoxazolidine, oxazolidine, pyrazolidine, imidazolidine, pyrrolidin-2-one, tetrahydrothiophene-1,1-dioxide, pyrrolidine-2,5-dione, tetrahydro-2H-pyran, piperidine, 1,2,3,6-tetrahydropyridine, 1,4-dioxane, morpholine, piperazine, thiomorpholine, piperidin-2-one, piperidin-4-one, thiomorpholine-1,1-dioxide, 1,3-oxazinan-2-one, morpholin-3-one, piperazine-2-one, azepane, 1,4-oxazepane, 1,4-diazepane, azepan-2-one, 1,4-diazepan-5-one, quinuclidine, 2-aza-bicyclo[2.2.1]heptane, 8-aza-bicyclo[3.2.1]octane, 5-oxa-2-aza-bicyclo[2.2.1]heptane, 2-oxa-5-aza-bicyclo[2.2.1]heptan-3-one, 2-oxa-5-aza-bicyclo[2.2.2]octan-3-one, 1-methyl-5,6-pyrrolyl-7-oxa-bicyclo[2.2.1]heptane, 6-aza-bicyclo[3.2.1]octane, 3,8-diaza-bicyclo[3.2.1]octan-2-one, 2,2-dimethyl-tetrahydro-3aH-[1,3]dioxolo[4,5-c]pyrrole, 3,3-cyclohexylpyrrolidine, 1,5-diaxo-9-azaspiro[5,5]undecane, octahydro-1H-isoindole, decahydroquinoline, decahydroisoquinoline, octahydropyrrolo[1,2a]pyrazine, octahydro'1H-pyrido[1,2a]pyrazine, octahydropyrrolo[3,4-c]pyridine-3-one, decahydropyrazino[1,2-a]azepine, furan, 1H-pyrrole, isoxazole, oxazole, 1H-pyrazole, 1H-imidazole, thiazole, 1,2,4-oxadiazole, 1,3,4-oxadiazole, 4H-1,2,4-triazole, 1H-tetrazole, pyridine, pyridazine, pyrimidine, pyrazine, pyridine-2(1H)-one, 1,4,5,6-tetrahydrocyclopenta[c]pyrazole, 6,7-dihydro-5H-pyrrolo[2,1-c][1,2,4]triazole, 2,3-dihydroimidazo[2,1-b]thiazole, imidazo[2,1-b][1,3,4-c]pyridine, 4,5,6,7-tetrahydro-3H-imidazo[4,5-c]pyridine, 5,6,7,8-tetrahydroimidazo[1,5-a]pyrazine, 4,5,6,7-tetrahydrothiazole[5,4-c]pyridine, 5,6,7,8-tetrahydro-[1,2,4]triazolo[4,3-a]pyrazine, quinoline, isoquinoline, 2,3-dihydrobenzofuran, 5,6,7,8-tetrahydroquinoline, 3,4-dihydro-1H-isochromene, 1,2,3,4-tetrahydroisoquinoline, 4H-benzo[d][1,3]dioxane, 5,6,7,8-tetrahydropyrido[3,4-d]pyrimidine, benzofuran, 1H-indole, benzo[d]oxazole, 1H-benzo[d]imidazole, H-imidazo[1,2-a]pyridine, imidazo[1,2-a]pyrimidine, 5,6,7,8-tetrahydroimidazo[1,5-a]pyrazine-3(2H)-one, 2,3,4,5-tetrahydro-1H-benzo[d]azepine, 2,3,4,5-tetrahydrobenzo[f][1,4]oxazepine, 5,6,7,8-tetrahydro-4H-isoxazolo[4,3-d]azepine and 6,7,8,9-tetrahydro-2H-[1,2,4]triazolo[4,3-g][1,4]diazepin-3(5H)-one.

It is to be understood that if a carbocyclic or heterocyclic moiety may be bonded or otherwise attached to a designated substrate, through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

Pharmaceutically acceptable salts of the compounds of the invention include the acid addition and base salts (including disalts) thereof. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of a compound of the invention may be readily prepared by mixing together solutions of a compound of the invention and the desired acid or base, as appropriate. The salt may precipitate from solution and be collected by filtration or may be recovered by evaporation of the solvent. The degree of ionization in the salt may vary from completely ionized to almost non-ionized.

The compounds of the invention which are complexes, such as clathrates and drug-host inclusion complexes, are within the scope of the invention. In contrast to the aforementioned solvates, the drug and host are present in stoichiometric or non-stoichiometric amounts. Also included are complexes containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

The compounds of the invention include all polymorphs and isomers thereof, including optical, geometric and tautomeric isomers as hereinafter defined and isotopically-labeled compounds.

The compounds of the invention containing one or more asymmetric carbon atoms may exist as two or more stereoisomers. Where a compound contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

All stereoisomers, geometric isomers and tautomeric forms of the compounds of the invention are included within the scope of the invention, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art [see, for example, "Stereochemistry of Organic Compounds" by E. L. Eliel (Wiley, New York, 1994)].

The invention includes all pharmaceutically acceptable isotopically-labeled compounds of the invention, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described in the accompanying Examples and Preparations using an appropriate isotopically-labeled reagents in place of the non-labeled reagent previously employed.

The parenthetical negative or positive sign used herein in the nomenclature denotes the direction plane polarized light is rotated by the particular stereoisomer.

One of ordinary skill will recognize that certain compounds of the invention may contain one or more atoms which may be in a particular stereochemical or geometric configuration, giving rise to stereoisomers and configurational isomers. All such isomers and mixtures thereof are included in the invention. Solvates (hydrates) of the compounds of the invention are also included.

Other features and advantages will be apparent from the specification and claims which describe the invention.

DETAILED DESCRIPTION OF THE INVENTION

The examples and preparations provided below further illustrate and exemplify the compounds of the present invention and methods of preparing such compounds. It is to be understood that the scope of the present invention is not limited in any way by the scope of the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In general, the compounds of the invention may be prepared by processes known in the chemical arts, particularly in light of the description contained herein. Certain processes for the manufacture of the compounds of the invention are provided as further features of the invention and are illustrated in the reaction schemes provided below and in the experimental section. The use of various protecting groups in these reactions are also well known and are exemplified in Protective Groups In Organic Synthesis, Second Edition, T. W. Greene and P. G. M. Wuts, John Wiley and Sons, Inc. 1991, pages 227-229, which is hereby incorporated by reference in its entirety for all purposes.

The utility of the compounds of the invention as medical agents for the reduction of intraocular pressure and accordingly to treat glaucoma is demonstrated by the activity of the compounds in conventional assays, including the in vivo assay and a receptor binding assay. Such assays also provide a means whereby the activities of the compounds can be compared to each other and with the activities of other known compounds. The results of these comparisons are useful for determining dosage levels in mammals, including humans, for the treatment of such diseases.

The compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds of the invention intended for pharmaceutical use may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).]

The compounds of the invention may be administered directly to the eye, typically in the form of drops of a micronised suspension or solution in isotonic, pH-adjusted, sterile saline. Other formulations suitable for ocular administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid; a cellulosic polymer, for example, hydroxypropylmethylcellulose, hydroxyethylcellulose, or methyl cellulose; or a heteropolysaccharide polymer, for example, gelan gum, may be incorporated together with a preservative, such as benzalkonium chloride.

The compounds of the invention can be incorporated into various types of ophthalmic formulations for delivery to the eye. These compounds may be combined with ophthalmologically acceptable preservatives, surfactants, viscosity enhancers, penetration enhancers, buffers, sodium chloride and water to form aqueous, sterile ophthalmic suspensions or solutions. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940 or the like according to the published formulations for analogous ophthalmic preparations; preservatives and tonicity agents can be incorporated. Ophthalmic solution formulations may be prepared by dissolving the active ingredient in a physiologically acceptable isotonic aqueous buffer. Further, the ophthalmic solution may include an ophthalmologically acceptable surfactant to assist in dissolving the active ingredient. Furthermore, the ophthalmic solution may contain a thickener such as hydroxymethylcellulose, hydroxyethylcellulose, hydroxypropylmethylcellulose, methyl-cellulose, polyvinylpyrrolidone, or the like to improve the retention of the medicament in the conjunctival sac.

The compounds of the invention are preferably formulated as topical ophthalmic suspensions or solutions, with a pH of about 4.5 to 7.8. The compounds will normally be contained in these formulations in an amount of 0.1% to 10% by weight, but preferably in an amount of 0.25% to 5.0% by weight. Thus, for topical presentation, 1 to 3 drops of these formulations would be delivered to the surface of the eye 1 to 4 times a day according to the routine discretion of a skilled clinician.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO91/11172, WO94/02518 and WO98/55148.

Depending on the disease and condition of the patient, the term "treatment" as used herein may include one or more of curative, palliative and prophylactic treatment.

As mentioned above, objects of the present invention are also pharmaceutical compositions containing at least a compound of the present invention of formula (I) together with non-toxic adjuvants and/or carriers typically employed in the pharmaceutical field.

The preferred route of administration is topical. The compounds of the present invention can be administered as solutions, suspensions or emulsions (dispersions) in an ophthalmically acceptable vehicle. The term "ophthalmic acceptable vehicle" as used herein refers to any substance or combination of substances which are non-reactive with the compounds and suitable for administration to patient.

Preferred are aqueous vehicles suitable for topical application to the patient's eyes.

Other ingredients which may be desirable to use in the ophthalmic compositions of the present invention include antimicrobials, preservatives, co-solvents, surfactants and viscosity building agents.

The invention also relates to a method for treating glaucoma or ocular hypertension, said method consisting in contacting an effective intraocular pressure reducing amount of a composition with the eye in order to reduce eye pressure and to maintain said pressure on a reduced level.

The doses of prostaglandin nitroderivatives can be determined by standard clinical techniques and are in the same range or less than those described for the corresponding underivatized, commercially available prostaglandin compounds as reported in the: Physician's Desk Reference, Medical Economics Company, Inc., Oradell, N. J., 58$^{th}$ Ed., 2004; The pharmacological basis of therapeutics, Goodman and Gilman, J. G. Hardman, L. e. Limbird, Tenth Ed.

The compositions contain 0.1-0.30 μg especially 1-10 μg, per application of the active compound.

The treatment may be advantageously carried out whereby one drop of the composition, corresponding to about 30 μl is administered about 1 to 2 times per day to the patient's eye.

It is further contemplated that the compounds of the present invention can be used with other medicaments known to be useful in the treatment of glaucoma or ocular hypertension, either separately or in combination. For example, the compounds of the present invention can be combined with (i) beta-blockers, such as timolol, betaxolol, levobunolol and the like (see U.S. Pat. No. 4,952,581); (ii) carbonic anhydrase inhibitors, such as brinzolamide; (iii) adrenergic agonists including clonidine derivatives, such as apraclonidine or brimonidine (see U.S. Pat. No. 5,811,443). Also contemplated is the combination with nitrooxy derivatives of the above reported compounds, for example nitrooxy derivatives of beta-blockers such as those described in U.S. Pat. No. 6,242, 432.

The following non-limiting preparations and Examples illustrate the preparation of the compounds of the invention.

EXAMPLES

In the examples described below, unless otherwise indicated, all temperatures are set forth in degrees Celsius and all parts and percentages are by weight. Reagents may be purchased from commercial suppliers, such as Sigma-Aldrich Chemical Company, Acros Organics, or Lancaster Synthesis Ltd. and may be used without further purification unless otherwise indicated. Tetrahydrofuran (THF), methylene chloride ($CH_2Cl_2$ or DCM), N,N-dimethylacetamide (DMA), acetonitrile (MeCN or ACN), and N,N-dimethylformamide (DMF) may be purchased from Aldrich in Sure-Seal bottles and used as received. All solvents may be purified using standard methods known to those skilled in the art, unless otherwise indicated. Diethyl ether is abbreviated as $Et_2O$. Ethyl acetate is abbreviated as EtOAc or EA. Trifluoroacetic acid is abbreviated as TFA. Acetic acid is abbreviated as HOAc or AcOH. Trifluoromethanesulfonate, or triflate, is abbreviated as "OTf." tert-Butoxycarbonyl is abbreviated as BOC. 4-(N,N-Dimethylamino)pyridine is abbreviated as DMAP. N-Methyl-morpholine is abbreviated as NMM. acetic anhydride as $Ac_2O$. N-(3-dimethylaminopropyl)-N'-ethylcarbodiimide hydrochloride is abbreviated as EDAC or EDC.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Microwave chemistry was carried out using an Emrys™ Optimizer EXP from Personal Chemistry, Inc. (now Biotage). Analytical thin layer chromatography (TLC) was performed using glass-backed silica gel 60 F 254 pre-coated plates (Merck Art 5719) and eluted with appropriate solvent ratios (v/v). Reactions were assayed by TLC or LCMS and terminated as judged by the consumption of starting material. Visualization of the TLC plates was done with UV light (254 nm wavelength) or with an appropriate TLC visualizing solvent and activated with heat. Analytical HPLC performed with Waters or Agilent instruments. Flash column chromatography (Still et al., *J. Org. Chem.*, 1978, 43, 2923) was performed using silica gel 60 (Merck Art 9385) or various MPLC systems, such as Biotage or ISCO purification systems (i.e., Biotage SP4 model). Preparative HPLC was done with several methods as follows: Prep LC 4000 system from Water with Ultra 120 10 mm C8 column from Peeke Scientific. Mass-directed prep HPLC with an Agilent A2Prep System, with computer-controlled gradients of two mobile phases (100% water with 0.1% formic acid and 100% acetonitrile with 0.1% formic acid) through a XBridge C18 column, 250 mm×30 mm, 5 μmicron particle size, and fraction collection guided by a detector tandem of UV diode array and (ESI) mass spectrometer. Supercritical Fluid Chromatography (SFC) purification was performed on Multigram II SFC from Berger Instruments using the ProNTo software platform. Chiralpak AS-H 21.2× 250 mm 5 u column was typically used and eluted with 20% MeOH in $CO_2$ at 140 bar. Flow rate was 60 mL/min. Peaks were collected with UV detection at 260 nm.

The compound structures in the examples below were confirmed by one or more of the following methods: proton magnetic resonance spectroscopy, mass spectroscopy, and elemental microanalysis. Proton magnetic resonance ($^1$H NMR) spectra were determined using a Bruker spectrometer operating at field strength of 300, 400, or 700 megahertz (MHz). Chemical shifts are reported in parts per million (ppm, δ) downfield from an internal tetramethylsilane standard. Alternatively, $^1$H NMR spectra were referenced relative to signals from residual protons in deuterated solvents as follows: $CDCl_3$=7.25 ppm; DMSO-$d_6$=2.49 ppm; $CD_3CN$=1.94 ppm, $CD_3OD$ or methanol-$d_4$=3.30 ppm; $C_6D_6$=7.16 ppm. Peak multiplicities are designated as follows: s, singlet; d, doublet; dd, doublet of doublets; t, triplet; dt, doublet of triplets; q, quartet; br, broadened; m, multiplet. Coupling constants are given in Hertz (Hz). For detailed structural elucidation of selected examples—proton, gCOSY, gHSQC, and gHMBC NMR spectra were acquired using a Bruker Avance 700 MHz NMR spectrometer equipped with a cryo-probe with the proton and carbon coils tuned to 700.13 MHz and 176.07 MHz respectively. A solution of about 10 mg of sample dissolved in 0.75 mL dimethylsulfoxide (d-6; 99.8% D) was used to acquire the spectra, which were referenced to the solvent signal (2.50 ppm for proton and 39.51 ppm for carbon).

Mass spectra (MS) data were obtained using Agilent LC mass spectrometer with APCI or (ESI) ionization. High resolution MS (HRMS) were performed on an Agilent G3250AA LCMSD/TOF mass spectrometer. Elemental microanalyses were performed by Atlantic Microlab Inc. and gave results for the elements stated within ±0.4% of the theoretical values.

Preferred compounds in accordance with the invention may be prepared in manners analogous to those specifically described below.

The examples and preparations provided below further illustrate and exemplify the compounds of the present invention and methods of preparing such compounds. It is to be understood that the scope of the present invention is not limited in any way by the scope of the following examples and preparations. The skilled artisan will recognize that different acids, amines, alkyl halides, aryl halides, coupling reagents, and heterocycles may be substituted in the following descriptions to suit the preparations of a desired embodiment. The following methods may be scaled upwards or downwards to suit the amount of desired material.

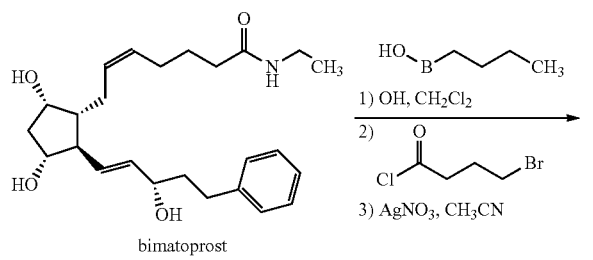

Example A-1

NCX 469

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 4-(Nitrooxy)butanoate
(A-1)

Following an analogous procedure from Bundy, G. L.; Peterson, D. C.; Cornette, J. C.; Miller, W. L.; Spilman, C. H.; Wilks, J. W. *J. Med. Chem.* 1983, 26, 1089-1099, to a solution of bimataprost (Cayman Chemicals; 200 mg, 0.481 mmol) in dichloromethane (4.8 mL) was added butylboronic acid (55.0 mg, 0.541 mmol). After 1 h at 42° C., some dichloromethane was evaporated and fresh dichloromethane added. This evaporation-fresh solvent addition sequence was repeated 3 times. 4 Å molecular sieves were added and the mixture stirred at 42° C. for 18 h. 4-Bromobutyryl chloride (0.061 mL; 0.53 mL) was added and allowed to stir at ambient temperature for 48 h. The solvent was removed under reduced pressure and the residue dissolved in acetonitrile (2.4 mL). Silver nitrate (163 mg, 0.962 mmol) was added and allowed to stir at ambient temperature for 18 h. An additional 100 mg of silver nitrate was added and stirred at 40° C. for 2 h. The resultant mixture was filtered through Celite, which was washed with acetonitrile. The filtrate was concentrated and dissolved in ethyl acetate (10 mL) and brine (2.5 mL). The organic layer was separated, washed with brine (2×2.5 mL), and concentrated under reduced pressure. The residue was purified by preparative reverse phase HPLC (water:acetonitrile 65-÷25%, with 0.1% acetic acid) and the pure fractions concentrated under reduced pressure to give A-1 (57 mg, 22%) as a yellow oil. Acylation regiochemistry at the alcohol at C-15 was confirmed using COSY and HMBC NMR. Correlations between $H_{15}$ and $C_{13}$, $C_{14}$, $C_{16}$, $C_{17}$, $C_{24}$, $H_{14}$ and $H_{16}$ were observed as depicted in the structure below:

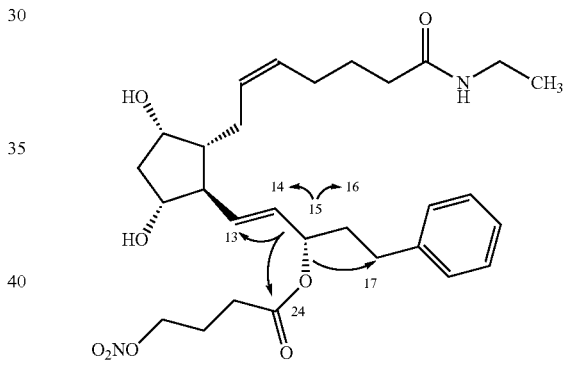

Specifically after these multiple NMR analyses, the methine proton assigned to C15, δ 5.20 (q, J=6.47 Hz, 1 H), which in turn showed correlations in the HMBC to the ester carbonyl at δ 171, in addition to C13, 14, 16, and 17.

$^1$H NMR (300 MHz, DMSO-$d_6$) δ 1.00 (t, J=7.16 Hz, 3 H), 1.27-1.58 (m, 4 H), 1.83-2.04 (m, 9 H), 2.07-2.30 (m, 3 H), 2.45 (t, J=7.25 Hz, 2 H), 2.62 (t, J=7.72 Hz, 2 H), 2.97-3.12 (m, 2 H), 3.63-3.77 (m, 1 H), 3.88-3.97 (m, 1 H), 4.41 (s, 1 H), 4.51-4.63 (m, 3 H), 5.20 (q, J=6.47 Hz, 1 H), 5.25-5.34 (m, 1 H), 5.38-5.57 (m, 3 H), 7.14-7.22 (m, 3 H), 7.25-7.34 (m, 2 H), 7.70 (s, 1 H).

$^{13}$C NMR (176 MHz, DMSO-$d_6$) δ 14.81, 21.76, 24.81, 25.32, 26.29, 29.92, 30.89, 33.21, 34.92, 35.69, 40.01, 44.01, 48.75, 54.24, 69.49, 72.89, 73.80, 75.47, 125.86, 128.22, 128.35, 128.99, 129.31, 135.81, 141.22, 171.36, 171.57.

LCMS (ESI): m/z 585.0 [MK]$^+$.

HRMS (TOF): calcd for $C_{29}H_{42}N_2O_8Na$[MNa]$^+$: 569.28334. Found: 569.28202.

Anal. Calcd for $C_{29}H_{42}N_2O_8 \cdot 0.8H_2O$: C, 62.08; H, 7.83; N, 4.99. Found: C, 61.87; H, 7.82; N, 4.95.

Scheme B

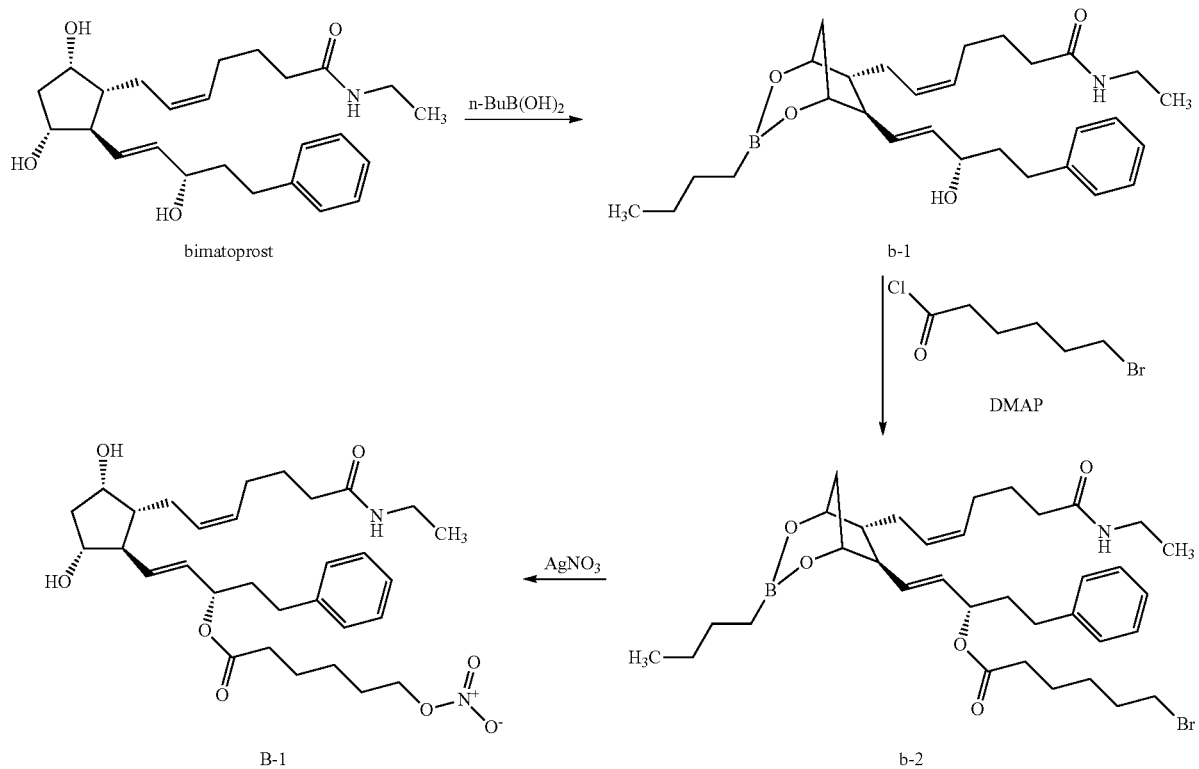

Example B-1

NCX470

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 6-(Nitrooxy)hexanoate (B-1)

Step 1: (5Z)-7-{(6R,7R)-3-Butyl-7-[(1E,3S)-3-hydroxy-5-phenylpent-1-en-1-yl]-2,4-dioxa-3-borabicyclo[3.2.1]oct-6-yl}-N-ethylhept-5-enamide (b-1)

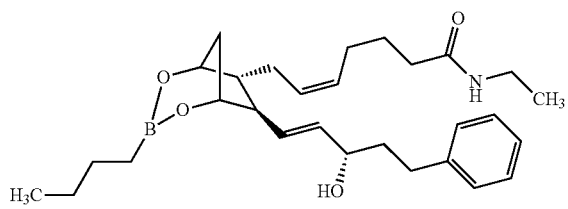

Following an analogous procedure from Bundy, G. L.; Peterson, D. C.; Cornette, J. C.; Miller, W. L.; Spilman, C. H.; Wilks, J. W. *J. Med. Chem.* 1983, 26, 1089-1099, to a solution of bimatoprost (Cayman Chemicals 16820, Lot 188757; 679 mg, 1.63 mmol) in DCM (10.9 mL) was added butylboronic acid (187 mg, 1.84 mmol). After 1 hour at 42° C., solvent was removed under reduced pressure and dried under high vacuum pump for 2 hours. Fresh DCM was added and stirred at 42° C. for another hour. Solvent was removed and dried under high vacuum pump for 1.5 hour. Fresh DCM was added again and stirred at 42° C. for 16 hours. Solvent was evaporated and dried in vacuum oven at 45° C. for 3 hours to give 904 mg (100%) of boronate b-1 as an oil, which was used directly in the next step without further purification.

$^1$H NMR (400 MHz, DMSO-$d_6$) δ 0.50-0.66 (m, 2 H), 0.76-0.91 (m, 3 H), 0.98 (t, J=7.20 Hz, 3 H), 1.16-1.35 (m, 4 H), 1.52 (quin, J=7.39 Hz, 2 H), 1.57-1.71 (m, 2 H), 1.74 (br. s., 1 H), 1.78-2.09 (m, 6 H), 2.08-2.23 (m, 2 H), 2.23-2.32 (m, 1 H), 2.52-2.65 (m, 2 H), 2.95-3.12 (m, 2 H), 3.79-3.93 (m, 1 H), 4.02 (s, 1 H), 4.25 (br. s., 1 H), 4.75 (d, J=4.55 Hz, 1 H), 5.26-5.54 (m, 4 H), 7.09-7.22 (m, 3 H), 7.26 (t, J=7.45 Hz, 2 H), 7.62-7.82 (m, 1 H).

Step 2: (1S,2E)-3-{(6R,7R)-3-Butyl-7-[(2Z)-7-(ethylamino)-7-oxohept-2-en-1-yl]-2,4-dioxa-3-borabicyclo[3.2.1]oct-6-yl}-1-(2-phenylethyl)prop-2-en-1-yl 6-Bromohexanoate (b-2)

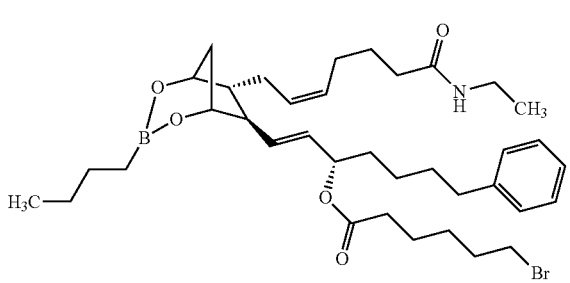

To a solution of (5Z)-7-{(6R,7R)-3-butyl-7-[(1E,3S)-3-hydroxy-5-phenylpent-1-en-1-yl]-2,4-dioxa-3-borabicyclo

[3.2.1]oct-6-yl}-N-ethylhept-5-enamide (b-1; 1.63 mmol) in DCM (12 mL) at 0° C. were slowly introduced DMAP (226 mg, 1.79 mmol) and 6-bromohexanoyl chloride (282 uL, 1.88 mmol). After 3 days at ambient temperature, another 0.25 eq. of DMAP (57 mg) and 0.25 eq. of 6-bromohexanoyl chloride (71 uL) were added and allowed to stir at ambient temperature for one day. An additional 0.25 eq. of 6-bromohexanoyl chloride (71 uL) was added and stirred at ambient temperature for 16 hours. The mixture was diluted with DCM and washed with water (1×) and brine (1×). The DCM layer was dried over anhydrous sodium sulfate and concentrated to give 1330 mg of crude ester b-2 as a light yellow oil, which was used without further purification.

$^1$H NMR (400 MHz, DMSO-$d_6$) δ 0.57 (s, 2 H), 0.77-0.92 (m, 3 H), 0.98 (t, J=7.20 Hz, 3 H), 1.18-1.32 (m, 4 H), 1.39 (d, J=6.57 Hz, 3 H), 1.46-1.64 (m, 4 H), 1.81 (dt, J=13.89, 6.95 Hz, 6 H), 1.95-2.08 (m, 3 H), 2.08-2.24 (m, 2 H), 2.29 (t, J=7.20 Hz, 3 H), 2.51-2.62 (m, 3 H), 3.03 (dd, J=7.33, 5.56 Hz, 2 H), 3.62 (d, J=6.57 Hz, 2 H), 4.01 (s, 1 H), 4.19-4.33 (m, 1 H), 5.03-5.18 (m, 1 H), 5.36 (d, J=6.32 Hz, 2 H), 5.47-5.57 (m, 2 H), 7.16 (d, J=7.58 Hz, 3 H), 7.26 (d, J=7.07 Hz, 2 H), 7.61-7.81 (m, 1 H).

Step 3: (1S,2E)-3-{(1R,2R,3S,5R)-2-[(2Z)-7-(Ethylamino)-7-oxohept-2-en-1-yl]-3,6-dihydroxycyclopentyl}-1-(2-phenylethyl)prop-2-en-1-yl 6-(Nitrooxy)hexanoate (B-1)

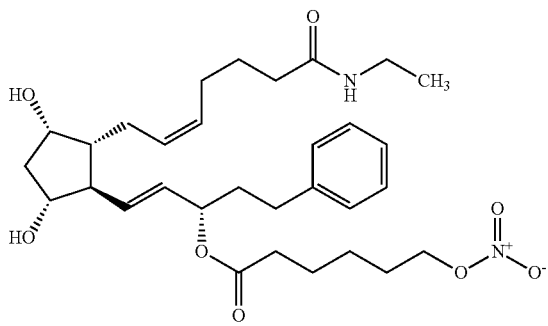

To a solution of (1S,2E)-3-{(6R,7R)-3-butyl-7-[(2Z)-7-(ethylamino)-7-oxohept-2-en-1-yl]-2,4-dioxa-3-borabicyclo[3.2.1]oct-6-yl}-1-(2-phenylethyl)prop-2-en-1-yl 6-bromohexanoate (b-2; 1.63 mmol) in MeCN (10.1 mL) was added silver nitrate (1030 mg, 6.06 mmol). After stirring at ambient temperature for two days, another 0.5 eq. silver nitrate (217 mg) was added and stirred at ambient temperature for three days. The mixture was filtered through a pad of Celite. The solid was washed with EtOAc. The filtrate was concentrated and residue was dissolved in EtOAc. The solution was washed with water (1×) and brine (1×), dried over anhydrous sodium sulfate and concentrated to give the crude product, which was then purified by preparative reverse phase HPLC (water:acetonitrile, with 0.1% acetic acid) to give 372 mg (39.7%) of nitrate B-1 as a yellow-brownish oil.

$^1$H NMR (700 MHz, DMSO-$d_6$) δ 0.97 (t, J=7.08 Hz, 3 H), 1.28-1.37 (m, 3 H), 1.42 (ddd, J=14.04, 5.64, 2.43 Hz, 1 H), 1.47 (qd, J=7.45, 7.30 Hz, 2 H), 1.52-1.58 (m, J=7.63, 7.63, 7.52, 7.30 Hz, 2 H), 1.62-1.68 (m, J=7.35, 7.35, 7.19, 6.86 Hz, 2 H), 1.81-1.90 (m, 2 H), 1.93 (q, J=7.08 Hz, 3 H), 1.97 (t, J=7.52 Hz, 2 H), 2.08 (dd, J=13.49, 5.97 Hz, 2 H), 2.13-2.21 (m, 2 H), 2.29 (t, J=7.30 Hz, 2 H), 2.58 (t, J=7.96 Hz, 2 H), 2.99-3.05 (m, 2 H), 3.66 (t, J=7.96 Hz, 1 H), 3.89 (d, J=3.54 Hz, 1 H), 4.40 (d, J=4.87 Hz, 1 H), 4.49 (t, J=6.63 Hz, 1 H), 4.56 (d, J=5.75 Hz, 1 H), 5.15 (q, J=6.63 Hz, 1 H), 5.26 (t, J=7.08 Hz, 1 H), 5.38-5.45 (m, 1 H), 5.45-5.52 (m, 1 H), 7.16 (d, J=7.96 Hz, 2 H), 7.26 (t, J=7.52 Hz, 1 H), 7.63-7.73 (m, 1 H).

$^{13}$C NMR (101 MHz, DMSO-$d_6$) δ 14.79, 24.02, 24.57, 24.78, 25.31, 25.71, 26.28, 30.89, 33.19, 33.48, 34.91, 35.74, 44.01, 48.75, 54.18, 69.47, 73.3, 73.65, 75.48, 125.83 128.20, 128.32, 128.95, 129.09, 129.29, 135.61, 141.21, 171.53, 171.97.

Proton, gCOSY, gHSQC, and gHMBC NMR spectra were found to be consistent with the structure depicted, based upon detailed inspection of proton chemical shifts, integration, couplings, as well as key homo and hetero-nuclear correlation observed in 2D spectra. The absence of carbon correlations in the HSQC spectrum allowed for the identification of hydroxyl protons. The observation of correlations from the hydroxyl protons to neighboring methine and methylene protons in the COSY spectrum enabled the determination of substitution of the cyclopentyl ring. Observation of key correlations in the HMBC spectra from hydroxy and methine signals to distinct carbon resonances allowed for further confirmation of structure.

Key COSY Correlations Observed for Example B-1

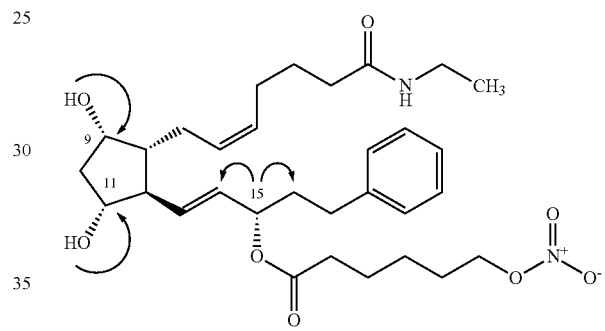

The COSY and HSQC helped assign the hydroxyl protons to resonances at δ 4.56 (d, J=5.75 Hz, 1 H) and 4.40 (d, J=4.87 Hz, 1 H) and methine protons: C-9 to δ 3.89 (d, J=3.54 Hz, 1 H), C-11 to δ 3.66 (t, J=7.96 Hz, 1 H), and C15 to δ 5.15 (q, J=6.63 Hz, 1 H).

Key HMBC Correlations Observed for Example B-1

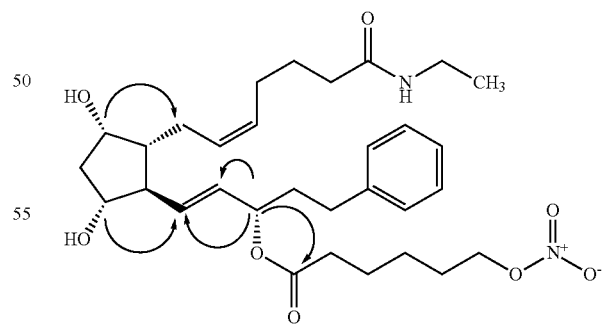

A key correlation for the site of attachment was found in the HMBC spectrum for proton at C-15 assigned to resonance at δ 5.15 (q, J=6.63 Hz, 1 H) to the carbonyl of the ester at δ 171.97.

LCMS (ES-API): m/z 597.2 (M+Na)$^+$.

Elemental analysis: Calcd for $C_{31}H_{46}N_2O_8$: C, 64.79; H, 8.07; N, 4.87. Found: C, 64.71; H, 8.08; N, 4.90.

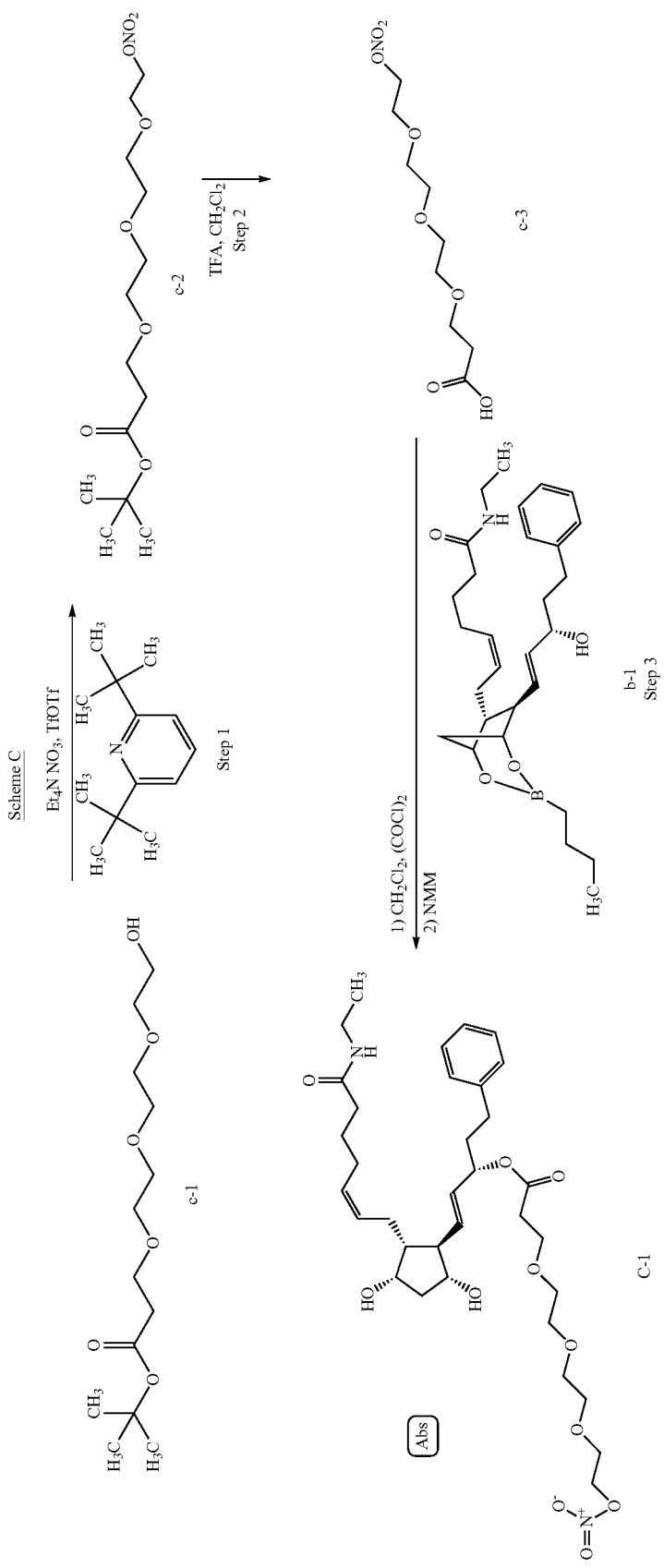

Example C-1

NCX 471

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 3-(2-{2-[2-(Nitrooxy)ethoxy]ethoxy}ethoxy)propanoate (C-1)

Step 1: tert-Butyl 3-(2-{2-[2-(Nitrooxy)ethoxy]ethoxy}ethoxy)propanoate (c-1)

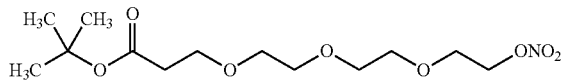

To a solution of tert-butyl 12-hydroxy-4,7,10-trioxadodecanoate (Fluka; 2.50 g, 8.98 mmol) in dichloromethane (45 mL) at −50° C. was added tetraethylammonium nitrate (3.45 g, 18.0 mmol), followed by 2,6-di-tert-butylpyridine (2.98 mL, 13.50 mmol). Trifluoromethanesulfonic anhydride (1.66 mL, 9.88 mmol) in methylene chloride (0.5 mL) was slowly added, stirred at −50° C. for 1 h, and then allowed to warm to room temperature over 18 h. Dichloromethane (45 mL) and 1N aq. HCl (45 mL) were added. The organic layer was separated, washed with brine (45 mL), dried (MgSO$_4$), and concentrated under reduced pressure. The residue was purified by column chromatography (ethyl acetate-hexane 10-100%) to give c-1 (2.68 g, 92%) as a colorless oil.

$^1$H NMR (300 MHz, DMSO-d$_6$) δ 1.41 (s, 9 H), 2.43 (t, J=6.2 Hz, 2 H), 3.48-3.56 (m, 8 H), 3.60 (t, J=6.2 Hz, 2 H), 3.68-3.77 (m, 2 H), 4.60-4.73 (m, 2 H).

HRMS (TOF): calcd for C$_{13}$H$_{26}$NO$_8$ [MH]$^+$: 324.16529. Found: 324.16601.

Anal. Calcd for C$_{13}$H$_{25}$NO$_8$: C, 48.29; H, 7.79; N, 4.33. Found: C, 48.21; H, 7.96; N, 4.39.

Step 2: 3-(2-{2-[2-(Nitrooxy)ethoxy]ethoxy}ethoxy)propanoic Acid (c-2)

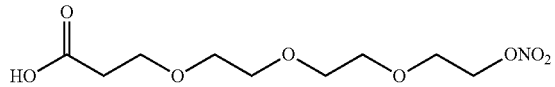

To a solution of c-1 (1.0 g, 3.1 mmol) in dichoromethane (7.5 mL) at 0° C. was added trifluoroacetic acid (7.5 mL) and allowed to warm to ambient temperature over 3 h. Toluene (2 mL) was added and then the mix concentrated under reduced pressure to give acid c-2 (0.87 g, 100%) as a colorless oil, which was used without further purification.

$^1$H NMR (300 MHz, DMSO-d$_6$) δ 2.46 (t, J=6.3 Hz, 2 H), 3.49-3.58 (m, 8 H), 3.62 (t, J=6.4 Hz, 2 H), 3.70-3.76 (m, 2 H), 4.59-4.73 (m, 2 H).

LCMS (ESI): m/z 268.1 [MH]$^+$.

HRMS (TOF): calcd for C$_9$H$_{18}$NO$_8$ [MH]$^+$: 268.10269. Found: 268.10435.

Step 3: (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 3-(2-{2-[2-(Nitrooxy)ethoxy]ethoxy}ethoxy)propanoate (C-1)

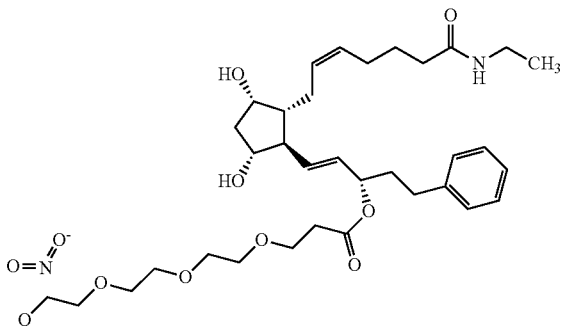

To a 0° C. solution of acid c-2 (204 mg, 0.764 mmol) in dichloromethane (2.5 mL) was added oxalyl chloride (0.065 mL, 0.764 mmol) and allowed to warm to ambient temperature for 18 h. Crude alcohol b-1 (727 mg, 1.44 mmol) in dichloromethane (1 mL) followed by NMM (0.113 mL, 1.02 mmol) and DMAP (6.2 mg, 0.051 mmol) were added and allowed to stir at ambient temperature for 18 h. The mix was cooled to 0° C., additional oxalyl chloride (0.035 mL) added, and allowed to warm to ambient temperature over 18 h. The mixture was quenched with water (0.5 mL) and concentrated in vacuo. The residue was purified by preparative reverse phase HPLC (water:acetonitrile 60→25%, with 0.1% acetic acid) and the pure fractions concentrated under reduced pressure to give C-1 (38 mg, 11%) as a colorless oil.

$^1$H NMR (300 MHz, DMSO-d$_6$) δ 0.98 (t, J=7.16 Hz, 3 H), 1.22-1.36 (m, 1 H), 1.40-1.56 (m, 3 H), 1.79-2.03 (m, 7 H), 2.06-2.29 (m, 3 H), 2.53-2.65 (m, 4 H), 2.94-3.11 (m, 2 H), 3.44-3.53 (m, 8 H), 3.60-3.71 (m, 5 H), 3.85-3.94 (m, 1 H), 4.37-4.41 (m, 1 H), 4.54-4.59 (m, 1 H), 4.61-4.65 (m, 2 H), 5.13-5.22 (m, 1 H), 5.23-5.30 (m, 1 H), 5.38-5.43 (m, 1 H), 5.46-5.51 (m, 2 H), 7.14-7.20 (m, 3 H), 7.23-7.31 (m, 2 H), 7.63-7.73 (m, 1 H).

LCMS (ESI): m/z 687.2 [MNa]$^+$.

HRMS (TOF): calcd for C$_{34}$H$_{52}$N$_2$O$_{11}$Na[MNa]$^+$: 687.34633. Found: 687.35495.

Scheme D

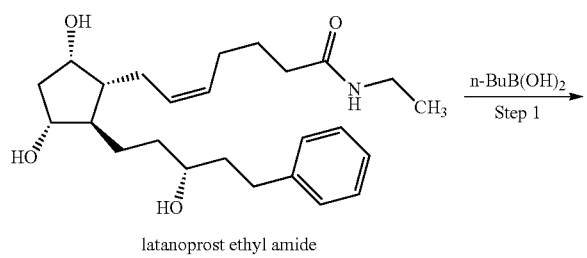

latanoprost ethyl amide

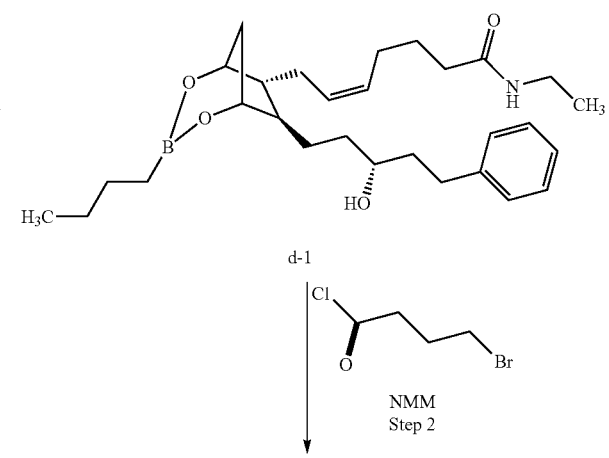

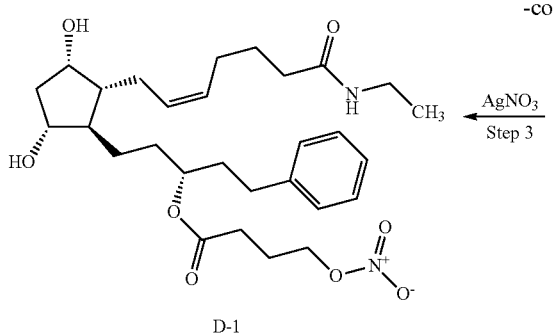

D-1

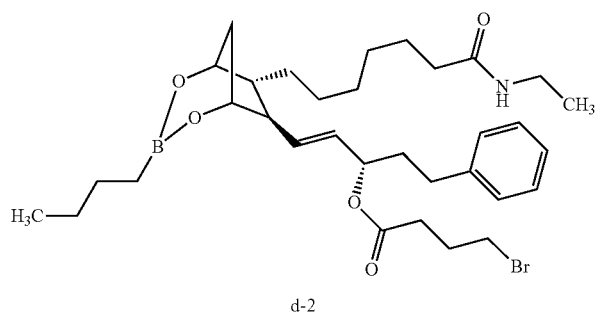

d-2

Example D-1

(1R)-3-{(1R,2R,3S,5R)-2-[(2Z)-7-(Ethylamino)-7-oxohept-2-en-1-0]-3,5-dihydroxycyclopentyl}-1-(2-phenylethyl)propyl 4-(Nitrooxy)butanoate (D-1)

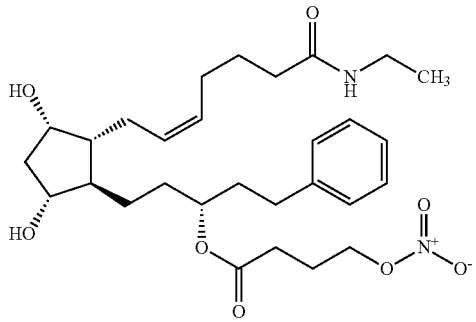

In an analogous sequence to that for Example A-1, for a first step: following a procedure from Bundy, G. L; Peterson, D. C.; Cornette, J. C.; Miller, W. L; Spilman, C. H.; Wilks, J. W. *J. Med. Chem.* 1983, 26, 1089-1099, to a solution of latanoprost ethyl amide (Cayman Chemicals Lot 181408; 730 mg, 1.75 mmol) in dichloromethane (17.5 mL) was added butylboronic acid (200 mg, 1.97 mmol). After 1 hour at 42° C., solvent was removed under reduced pressure and dried under high vacuum pump for 2 hours. Fresh DCM was added and stirred at 42° C. for another hour. Solvent was removed and dried under high vacuum pump for 1.5 hour. Fresh DCM was added again and stirred at 42° C. for 16 hours. Solvent was evaporated and dried under high vacuum pump for 3.5 hours to give 767 mg (71.0%) of boronate d-1 as a colorless oil, which was used directly in the next step without further purification.

In an analogous sequence to that for Example A-1, for a second step: to a solution of crude (5Z)-7-{(6R,7R)-3-butyl-7-[(3R)-3-hydroxy-5-phenylpentyl]-2,4-dioxa-3-borabicyclo[3.2.1]oct-6-yl}-N-ethylhept-5-enamide (d-1; 308 mg, 0.637 mmol) in DCM (6.4 mL) at 0° C. was added N-methyl morpholine (69 mg, 0.669 mmol) and 4-bromobutyryl chloride (148 mg, 0.796 mmol). The mixture was allowed to warm and stir at ambient temperature for 22 h. DCM (20 mL) and water (5 mL) were added. The organic layer was separated, washed with brine (5 mL), dried over anhydrous sodium sulfate, and concentrated at reduced pressure to give 340 mg (46%) of bromoester d-2 as a yellow oil, which was used without further purification.

In an analogous sequence to that for Example A-1, for a third step: crude (1S,2E)-3-{(6R,7R)-3-butyl-7-[7-(ethylamino)-7-oxoheptyl]-2,4-dioxa-3-borabicyclo-[3.2.1]oct-6-yl}-1-(2-phenylethyl)prop-2-en-1-yl 4-bromobutanoate (d-2; 340 mg of 46% pure by HPLC, theoretically 0.247 mmol) was dissolved in acetonitrile (5.4 mL). Silver nitrate (160 mg, 0.942 mmol) was added and stirred at ambient temperature for three days. An additional 91 mg of silver nitrate was added and stirred at 60° C. for 4 h. The resultant mixture was filtered through a pad of Celite, which was washed with EtOAc. The filtrate was concentrated and dissolved in ethyl acetate (10 mL), washed with brine water (1×) and brine (1×), and concentrated under reduced pressure. The residue was purified by preparative reverse phase HPLC (water:acetonitrile 65→25%, with 0.1% acetic acid) and the pure fractions concentrated under reduced pressure to give 13 mg (9.6%) of nitrate D-1 as a yellow oil.

$^1$H NMR (400 MHz, CHLOROFORM-d) δ 1.06-1.17 (m, 3 H), 1.29-1.48 (m, 2 H), 1.61-1.79 (m, 6 H), 1.81-1.94 (m, 4 H), 2.04 (qd, J=6.74, 6.57 Hz, 4 H), 2.08-2.26 (m, 4 H), 2.31-2.48 (m, 3 H), 2.63 (dt, J=9.16, 6.54 Hz, 2 H), 2.76-3.02 (m, 1 H), 3.20-3.36 (m, 2 H), 3.90 (br. s., 1 H), 4.15 (br. s., 1 H), 4.51 (t, J=6.32 Hz, 2 H), 4.86-5.08 (m, 1 H), 5.31-5.66 (m, 3 H), 7.12-7.23 (m, 3 H), 7.25-7.36 (m, 2 H).

LCMS (ES-API): m/z 549.2 (M+H)$^+$.

HRMS (TOF): calcd for $C_{29}H_{43}N_2O_8$ [MH]$^+$: 549.31704. Found: 549.31945.

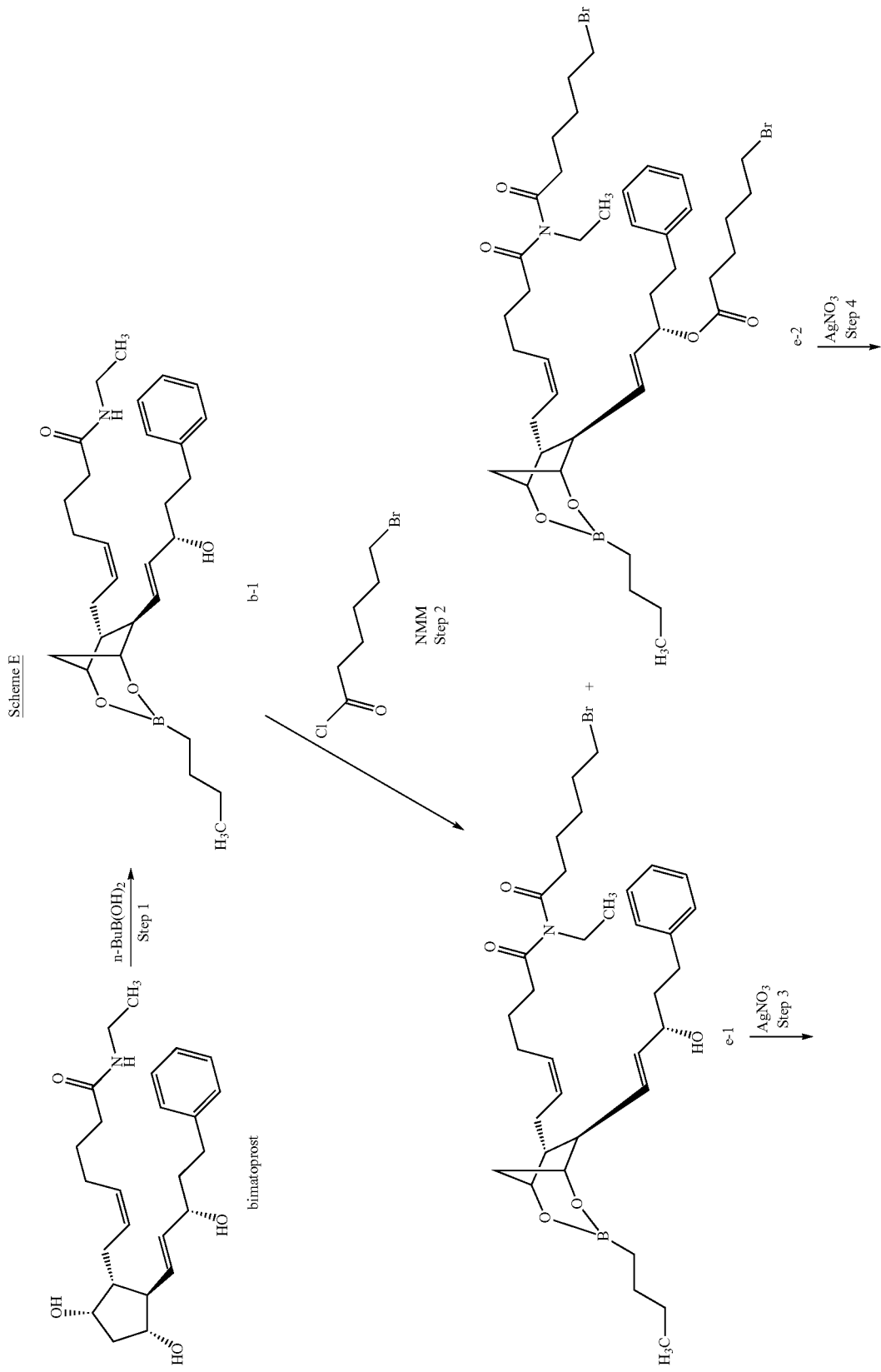

-continued
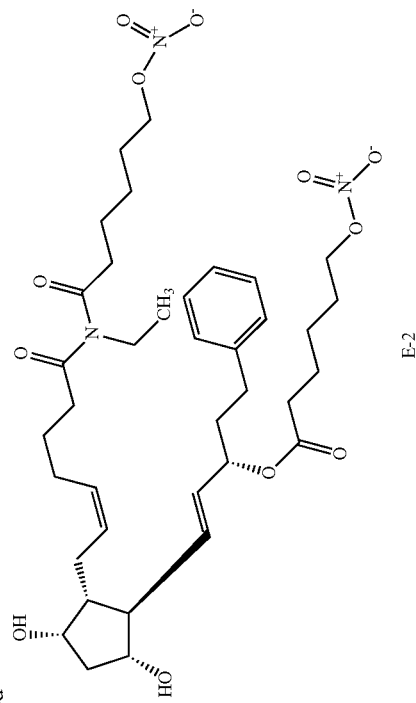
E-2
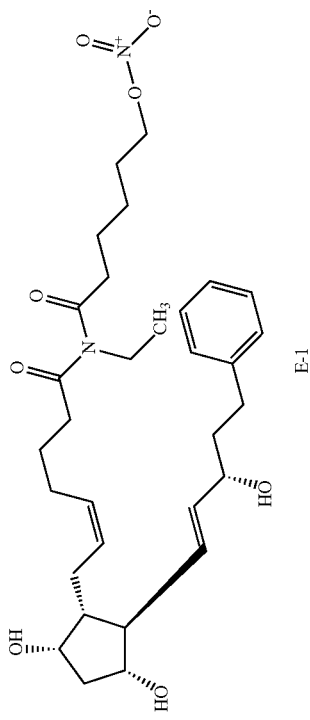
E-1

Example E-1

6-{[(5Z)-7-{(1R,2R,3R,5S)-3,5-Dihydroxy-2-[(1E,3S)-3-hydroxy-5-phenylpent-1-en-1-yl]cyclopentyl}hept-6-enoyl](ethyl)amino}-6-oxohexyl Nitrate and

Example E-2

(1S,2E)-3-{(1R,2R,3S,5R)-2-[(2Z)-7-{Ethyl[6-(nitrooxy)hexanoyl]amino}-7-oxohept-2-en-1-yl]-3,5-dihydroxycyclopentyl}-1-(2-phenylethyl)prop-2-en-1-yl 6-(Nitrooxy)hexanoate Step 2: (5Z)—N-(6-Bromohexanoyl)-7-{(6R,7R)-3-butyl-7-[(1E,3S)-3-hydroxy-6-phenylpent-1-en-1-yl]-2,4-dioxa-3-borabicyclo[3.2.1]oct-6-yl}-N-ethylhept-6-enamide (e-1) and (1S,2E)-3-{(6R,7R)-7-{(2Z)-7-[(6-Bromohexanoyl)(ethyl)amino]-7-oxohept-2-en-1-yl}-3-butyl-2,4-dioxa-3-borabicyclo[3.2.1]oct-6-yl}-1-(2-phenylethyl)prop-2-en-1-yl 6-Bromohexannate (e-2)

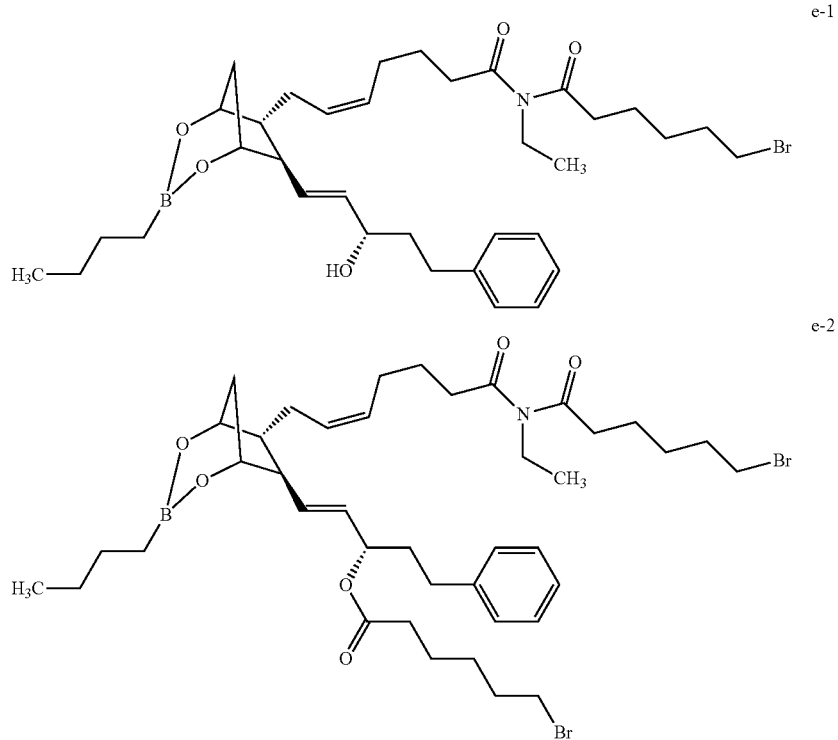

e-1 e-2

To a solution of (5Z)-7-{(6R,7R)-3-butyl-7-[(1E,3S)-3-hydroxy-5-phenylpent-1-en-1-yl]-2,4-dioxa-3-borabicyclo[3.2.1]oct-6-yl}-N-ethylhept-5-enamide (b-1; 708 mg, 1.47 mmol) in DCM (9.8 mL) at 0° C. were slowly introduced NMM (190 mg, 1.84 mmol) and 6-bromohexanoyl chloride (274 uL, 1.84 mmol). It was then stirred at ambient temperature for 3 days. The mixture was diluted with DCM and washed with water (1×) and brine (1×). The DCM layer was dried over anhydrous sodium sulfate and concentrated to give 819 mg crude product. The crude product was further purified by prep. HPLC (water:acetonitrile 65-425%, with 0.1% acetic acid) and the pure fractions concentrated under reduced pressure to give e-1 (291 mg; 30.1%) and e-2 (90 mg; 7.3%), respectively. Both intermediates e-1 and e-2 were each used respectively without further characterization.

Step 3: 6-{[(5Z)-7-{(1R,2R,3R,5S)-3,5-Dihydroxy-2-[(1E,3S)-3-hydroxy-5-phenylpent-1-en-1-yl]cyclopentyl}hept-5-enoyl](ethyl)amino}-6-oxohexyl Nitrate (E-1)

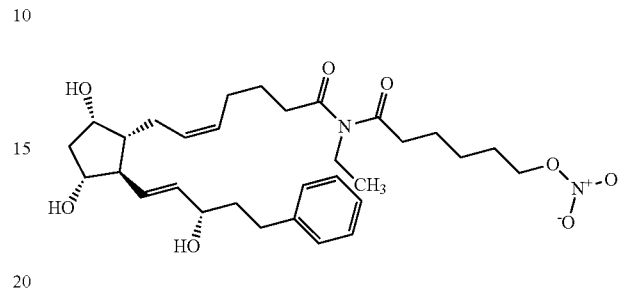

To a solution of (5Z)—N-(6-bromohexanoyl)-7-{(6R,7R)-3-butyl-7-[(1E,3S)-3-hydroxy-5-phenylpent-1-en-1-yl]-2,4-dioxa-3-borabicyclo[3.2.1]oct-6-yl}-N-ethylhept-5-enamide (e-1; 240 mg, 0.364 mmol) in MeCN (3.6 mL) was added silver nitrate (186 mg, 1.09 mmol). After stirring at ambient temperature for 1 day, another 2 eq. silver nitrate (124 mg) was added and stirred at ambient temperature for another day. The mixture was filtered through a pad of Celite. The solid was washed with EtOAc. The filtrate was concentrated and residue was dissolved in EtOAc. The solution was washed with water (1×) and brine (1×), dried over anhydrous sodium sulfate and concentrated to give the crude product, which was then purified by preparative reverse phase HPLC (water:acetonitrile, with 0.1% acetic acid) to give 160 mg (76.5%) of imide E-1 as colorless oil.

¹H NMR (400 MHz, DMSO-d₆) δ 1.00-1.10 (m, 3 H), 1.25-1.41 (m, 4 H), 1.48-1.60 (m, 5 H), 1.61-1.77 (m, 5 H), 1.89-2.06 (m, 5 H), 2.09-2.26 (m, 4 H), 3.55-3.73 (m, 4 H), 3.83-3.97 (m, 2 H), 4.36 (d, J=4.80 Hz, 1 H), 4.44-4.54 (m, 3 H), 4.66 (d, J=4.55 Hz, 1 H), 5.21-5.32 (m, 1 H), 5.35-5.52 (m, 3 H), 7.11-7.20 (m, 3 H), 7.25 (t, J=7.45 Hz, 2 H).

LCMS (ES-API): m/z 597.2 (M+Na⁺).

¹³C NMR (176 MHz, DMSO-d₆) δ 14.14, 23.97, 24.39, 24.59, 24.77, 25.89, 26.04, 31.35, 36.48, 36.74, 38.45, 40.01, 43.96, 48.86, 54.26, 69.46, 70.59, 73.71, 75.73, 125.54, 128.18, 128.21, 128.73, 129.65, 132.13, 135.18, 142.25, 175.33, 175.40.

Step 4: (1S,2E)-3-{(1R,2R,3S,6R)-2-[(2Z)-7-{Ethyl [6-(nitrooxy)hexanoyl]amino}-7-oxohept-2-en-1-yl]-3,6-dihydroxycyclopentyl}-1-(2-phenylethyl)prop-2-en-1-yl 6-(Nitrooxy)hexanoate (E-2)

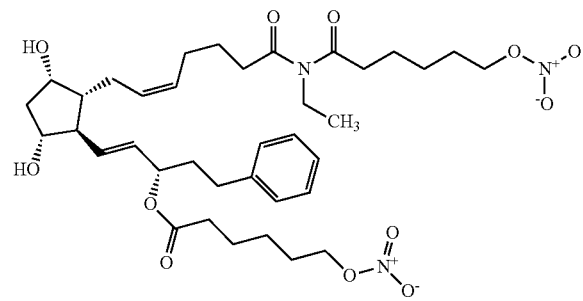

To a solution of (1S,2E)-3-[(6R,7R)-7-{(2Z)-7-[(6-bromo-hexanoyl)(ethyl)amino]-7-oxohept-2-en-1-yl}-3-butyl-2,4-dioxa-3-borabicyclo[3.2.1]oct-6-yl]-1-(2-phenylethyl)prop-2-en-1-yl 6-bromo-hexanoate (e-2; 700 mg, 0.838 mmol) in MeCN (0.91 mL) was added silver nitrate (93 mg, 0.546 mmol). After stirring at ambient temperature for 1 day, another 4 eq. silver nitrate (64 mg) was added and stirred at ambient temperature for another day. The mixture was filtered through a pad of Celite. The solid was washed with EtOAc. The filtrate was concentrated and residue was dissolved in EtOAc. The solution was washed with water (1×) and brine (1×), dried over anhydrous sodium sulfate and concentrated to give the crude product, which was then purified by preparative reverse phase HPLC (water:acetonitrile, with 0.1% acetic acid) to give 50 mg (8.1%) of imide-ester E-2 as colorless oil.

¹H NMR (700 MHz, DMSO-d₆) δ 1.04 (t, J=7.08 Hz, 3 H), 1.26-1.38 (m, 5 H), 1.42 (dt, J=14.15, 2.87 Hz, 1 H), 1.48-1.59 (m, 6 H), 1.61-1.70 (m, 4 H), 1.79-1.92 (m, 2 H), 1.93-2.02 (m, 3 H), 2.03-2.10 (m, 1 H), 2.12-2.23 (m, 2 H), 2.24-2.33 (m, 2 H), 2.58 (t, J=7.30 Hz, 4 H), 2.65 (t, J=7.30 Hz, 2 H), 3.61 (q, J=7.08 Hz, 2 H), 3.64-3.69 (m, 1 H), 3.90 (d, J=3.54 Hz, 1 H), 4.40 (d, J=4.87 Hz, 1 H), 4.50 (q, J=6.49 Hz, 4 H), 4.57 (d, J=5.75 Hz, 1 H), 5.16 (q, J=6.19 Hz, 1 H), 5.23-5.30 (m, 1 H), 5.40-5.53 (m, 3 H), 7.16 (d, J=7.96 Hz, 3 H), 7.26 (t, J=7.74 Hz, 2 H).

¹³C NMR (176 MHz, DMSO-d₆) δ 14.61, 24.44, 24.50, 24.86, 25.07, 25.20, 26.19, 26.37, 26.47, 31.39, 33.97, 36.25, 37.00, 37.18, 38.93, 40.48, 44.51, 49.29, 54.69, 69.90, 73.83, 74.13, 74.19, 75.97, 126.31, 128.65, 128.79, 129.28, 129.61, 129.98, 136.12, 141.67, 172.43, 175.82, 175.89.

LCMS (ES-API): m/z 756.2 (M+Na)⁺.

Scheme F

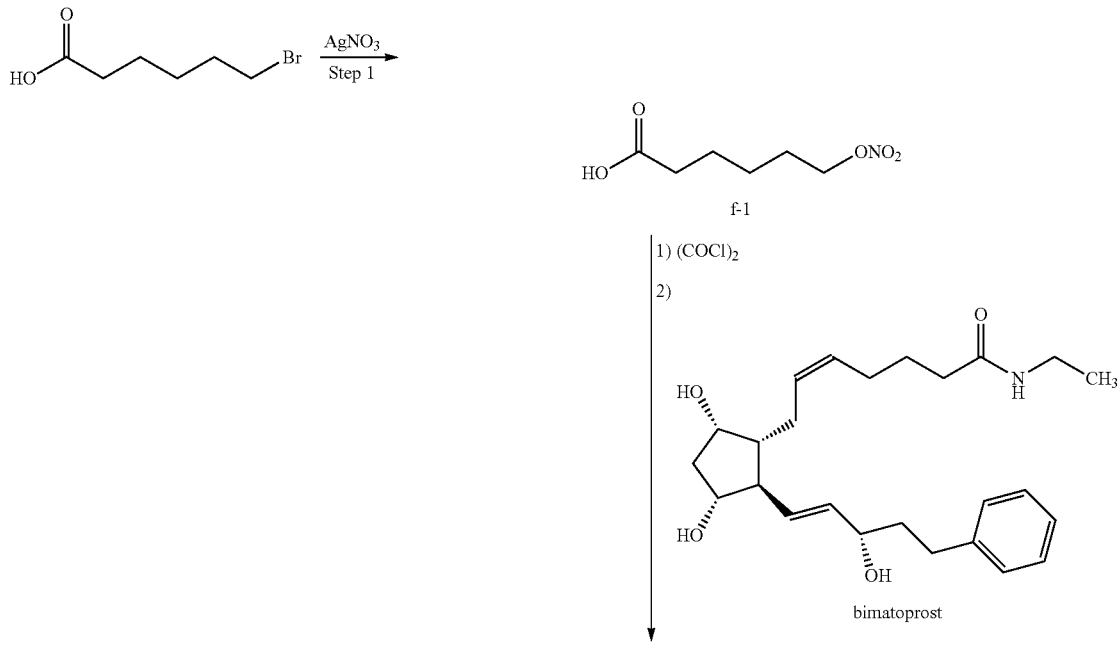

-continued

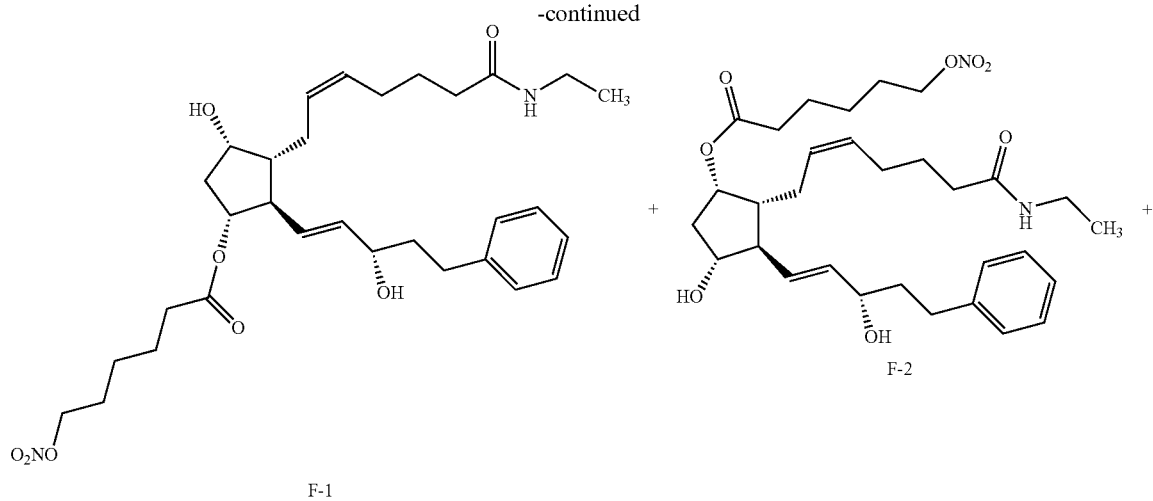

F-1

F-2

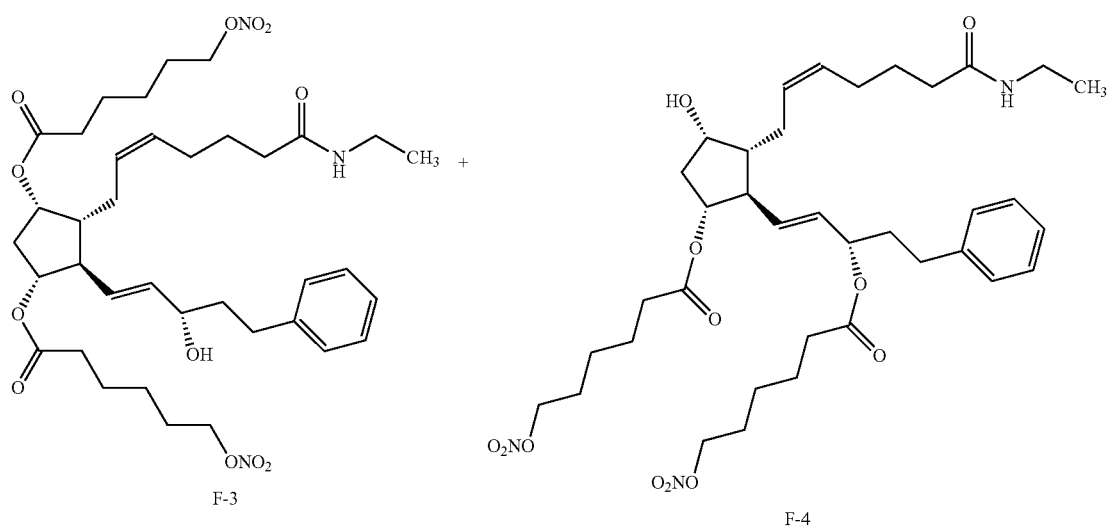

F-3

F-4

Step 1: 6-(Nitrooxy)hexanoic Acid

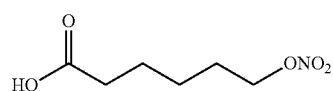

Similar to that described in US2006/189603 A1, silver nitrate was added to a solution of 6-bromohexanoic acid (4.88 g, 25 mmol) in acetonitrile (25 mL). After 12 h at ambient temperature, the residue after filtration and evaporation was chromatographed on silica gel with Biotage, eluting with EtOAc—CH$_2$Cl$_2$ 25-50% to yield product (4.0 g, 90%) as colorless oil.

$^1$H NMR (400 MHz, Chloroform-d$_6$) δ 1.40-1.60 (m, 2 H), 1.62-1.86 (m, 3 H), 2.03 (s, 1 H), 2.41 (t, J=7.33 Hz, 2 H), 4.48 (t, J=6.57 Hz, 2 H), 10.20 (bs, 1 H).

LCMS (ESI): m/z 200.20 (M+Na)$^+$.

HRMS. Calcd for $C_6H_{11}NO_5Na$ [M+Na]$^+$: 200.0529. Found: 200.0531.

Step 2: (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 6-(Nitrooxy)hexanoate (F-1) (1S,2R,3R,4R)-2-[(2Z)-7-(Ethylamino)-7-oxohept-2-en-1-yl]-4-hydroxy-3-[(1E,3S)-3-hydroxy-6-phenylpent-1-en-1-yl]cyclopentyl 6-(Nitrooxy)hexanoate (F-2) (1R,3S,4R,5R)-4-[(2Z)-7-(Ethylamino)-7-oxohept-2-en-1-yl]-5-[(1E,3S)-3-hydroxy-6-phenylpent-1-en-1-yl]cyclopentane-1,3-diyl bis[6-(Nitrooxy)hexanoate] (F-3) (1S,2E)-3-[(1R,2R,3S,5R)-2-[(2Z)-7-(Ethylamino)-7-oxohept-2-en-1-yl]-3-hydroxy-5-{[6-(nitro-oxy)hexanoyl]oxy}cyclopentyl]-1-(2-phenylethyl)prop-2-en-1-yl 6-(Nitrooxy)hexanoate (F-4)

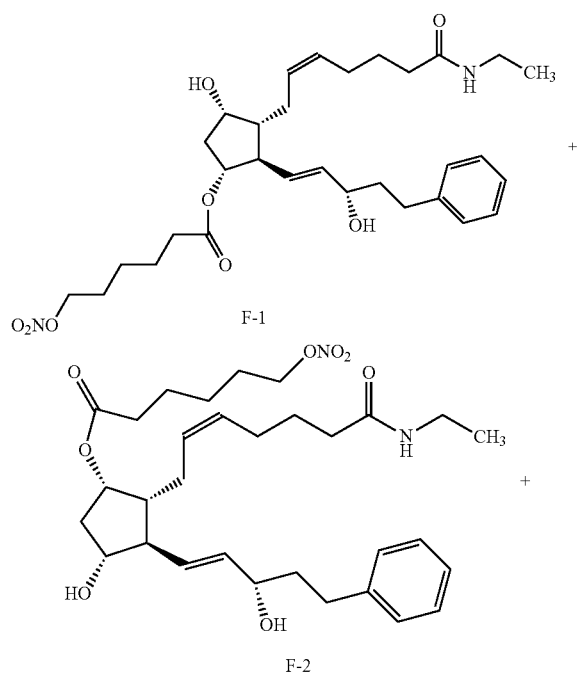

F-1

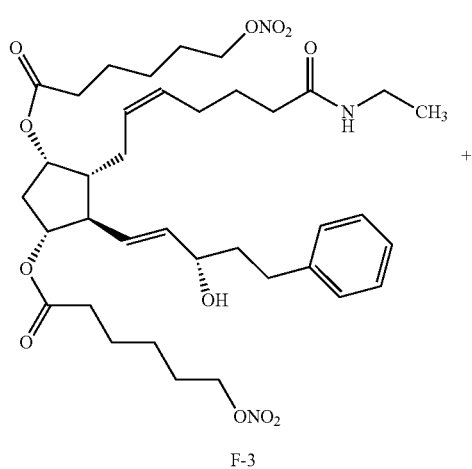

F-2

F-3

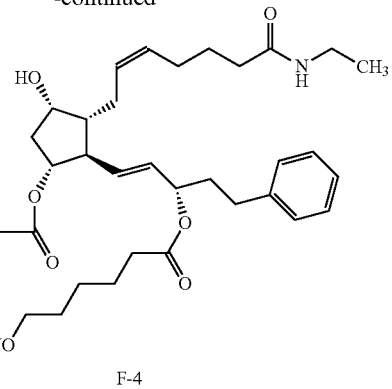

F-4

6-(Nitrooxy)hexanoic acid (1.77 g, 10.0 mmol) was dissolved in anhydrous dichloromethane (80 mL) under nitrogen at ambient temperature. The solution was cooled to 0° C., successively added 4 drops of anhydrous DMF and oxalyl chloride (870 uL, 10 mmol), and allowed to warm to ambient temperature. After 12 h, the mixture was filtered through a silica plug, which was washed with anhydrous dichloromethane (50 mL). The solvent was evaporated to give 1.71 g (88%) of crude presumed acid chloride (6-nitroxy-hexanoyl chloride) as a yellow oil, which was immediately used without further purification.

To a suspension of bimataprost (Cayman Chemicals; 831 mg, 2.00 mmol) in dichloromethane (10 mL) at 0° C. were added DMAP resin (Argonaut (Biotage "PS-DMAP"); 2.75 g of 1.60 mmol/g, 4.20 mmol) and the above crude 6-nitroxyhexanoyl chloride (822 mg, 2.1 mmol) under nitrogen. After 20 min at 0° C., the cooling bath was removed and stirred at ambient temperature 18 hours. The resin was filtered off, and the filtrate concentrated, then the crude mixture was separated by preparative reverse phase HPLC to provide 15-ester F-1 (142 mg, 12.4%) as colorless oil, 9-ester F-2 (20 mg, 1.7%) as a white solid, 9,11-diacyl nitrate F-3 as colorless oil, and 11.15-diacyl ester F-4 as colorless oil, respectively.

Example F-1

(1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 6-(Nitrooxy)hexanoate

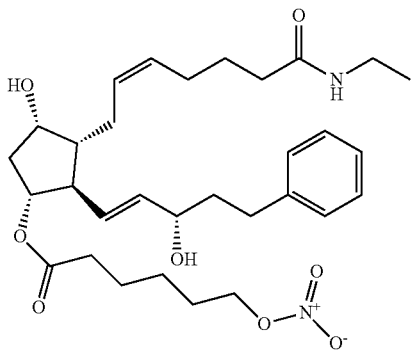

$^1$H NMR (700 MHz, DMSO-d$_6$) δ 0.98 (t, J=7.30 Hz, 3 H), 1.31 (dq, J=7.74, 7.59 Hz, 2 H), 1.42 (dd, J=15.48, 3.98 Hz, 1 H), 1.45-1.50 (m, 2 H), 1.50-1.54 (m, 2 H), 1.57-1.63 (m,

J=7.35, 7.35, 7.19, 6.86 Hz, 2 H), 1.63-1.70 (m, 2 H), 1.95 (d, J=7.08 Hz, 2 H), 1.98 (t, J=7.52 Hz, 3 H), 2.11 (t, J=15.70 Hz, 1 H), 2.25 (t, J=7.30 Hz, 2 H), 2.33 (ddd, J=14.82, 9.29, 5.53 Hz, 1 H), 2.45 (t, J=8.18 Hz, 1 H), 2.55-2.64 (m, 2 H), 2.98-3.06 (m, 2 H), 3.91 (qd, J=5.68, 5.53 Hz, 1 H), 3.95 (d, J=3.98 Hz, 1 H), 4.46 (t, J=6.63 Hz, 2 H), 4.61 (d, J=3.98 Hz, 1 H), 4.75 (d, J=4.87 Hz, 1 H), 4.77 (dd, J=7.74, 4.64 Hz, 1 H), 5.24-5.32 (m, 1 H), 5.38-5.49 (m, 3 H), 7.16 (d, J=7.52 Hz, 3 H), 7.25 (t, J=7.74 Hz, 2 H), 7.70 (t, J=4.64 Hz, 1 H).

$^{13}$C NMR (176 MHz, DMSO-$d_6$): δ 14.78, 24.04, 24.34, 24.49, 25.29, 25.67, 26.31, 31.14, 33.20, 33.40, 34.90, 40.00, 41.30, 48.67, 50.77, 69.27, 69.92, 73.88, 78.27, 125.54, 128.17, 128.22, 128.94, 129.24, 129.84, 136.07, 142.23, 171.57, 172.62.

Confirmed the structure as depicted, based upon detailed inspection of proton chemical shifts, integration, couplings, as well as key homo and hetero-nuclear correlation observed in 2D spectra. The absence of carbon correlations in the HSQC spectrum allowed for the identification of hydroxyl protons. The observation of correlations from the hydroxyl protons to neighboring methine and methylene protons in the COSY spectrum enabled the determination of substitution of the cyclopentyl ring.

Key COSY Correlations Observed

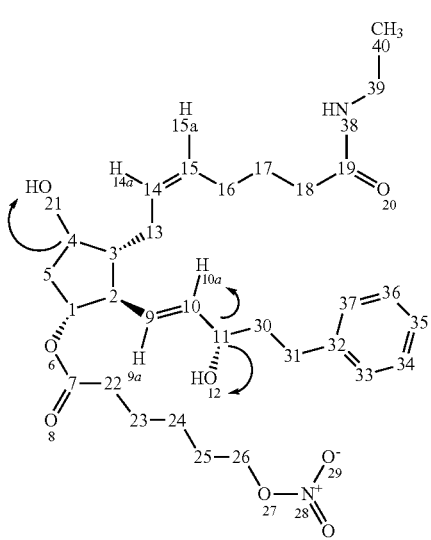

Key HMBC Correlations Observed

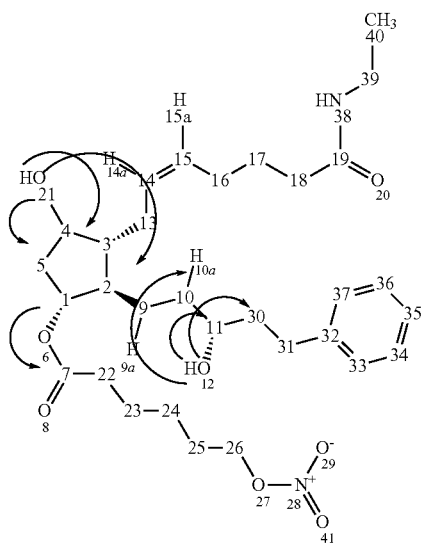

A key correlation for the site of attachment was found in the HMBC spectrum for proton at C-11 (numbered 1 above) assigned to resonance at δ 4.77 (dd, J=7.74, 4.64 Hz, 1 H) to the carbonyl of the ester (numbered 7 above) at δ 172.62.

LCMS ESI: m/z 597.2 (M+Na$^+$).

HRMS. Calcd for $C_{29}H_{42}BrNO_5Na$ [M+Na]$^+$: 597.3146. Found: 597.3134.

Example F-2

(1S,2R,3R,4R)-2-[(2Z)-7-(Ethylamino)-7-oxohept-2-en-1-yl]-4-hydroxy-3-[(1E,3S)-3-hydroxy-5-phenyl-pent-1-en-1-yl]cyclopentyl 6-(Nitrooxy)hexanoate

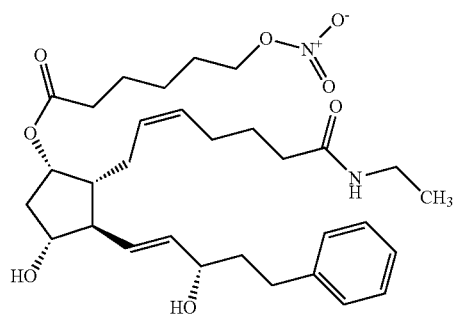

$^1$H NMR (700 MHz, DMSO-$d_6$) δ 0.98 (t, J=7.30 Hz, 3 H), 1.17-1.30 (m, 2 H), 1.33-1.41 (m, 4 H), 1.47 (dt, J=15.48, 7.74 Hz, 2 H), 1.56 (qd, J=7.67, 7.52 Hz, 2 H), 1.59-1.74 (m, 5 H), 1.86 (dd, J=13.71, 7.96 Hz, 1 H), 1.90-1.96 (m, 1 H), 1.98 (t, J=7.52 Hz, 2 H), 2.02 (t, J=5.09 Hz, 2 H), 2.17 (dt, J=11.94, 7.96 Hz, 1 H), 2.29 (q, J=7.08 Hz, 2 H), 2.36 (ddd, J=14.82, 8.62, 6.19 Hz, 1 H), 2.56-2.66 (m, 2 H), 3.03 (dd, J=7.30, 5.53 Hz, 2 H), 3.76 (dd, J=13.71, 2.65 Hz, 1 H), 3.88-3.95 (m, 1 H), 4.50 (t, J=6.63 Hz, 2 H), 4.73 (d, J=4.42 Hz, 1 H), 4.75 (d, J=5.75 Hz, 1 H), 4.91 (t, J=4.64 Hz, 1 H), 5.29 (d, J=4.42 Hz, 1 H), 5.36-5.44 (m, 1 H), 5.46-5.53 (m, 1 H), 7.10-7.20 (m, 3 H), 7.26 (t, J=7.52 Hz, 2 H), 7.70 (qd, J=5.68, 5.53 Hz, 1 H).

$^{13}$C NMR (176 MHz, DMSO-d$_6$) δ 14.78, 24.00, 24.58, 24.64, 25.23, 25.73, 26.33, 31.32, 33.19, 33.57, 34.85, 40.01, 41.45, 46.55, 54.70, 70.30, 73.67, 73.76, 75.04, 125.57, 128.05, 128.23, 128.26, 129.73, 130.77, 136.00, 142.27, 171.43, 172.27.

Confirmed the structure as depicted based upon detailed inspection of proton chemical shifts, integration, couplings, as well as key homo and hetero-nuclear correlation observed in 2D spectra. The absence of carbon correlations in the HSQC spectrum allowed for the identification of hydroxyl protons. The observation of correlations from the hydroxyl protons to neighboring methine and methylene protons in the COSY spectrum enabled the determination of substitution of the cyclopentyl ring.

Key COSY Correlations Observed

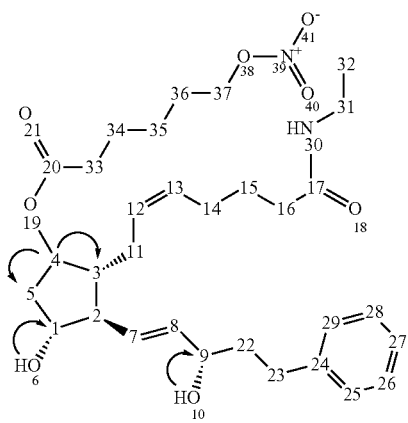

The COSY and HSQC helped assign the hydroxyl protons to resonances at δ 4.73 (d, J=4.42 Hz, 1 H), 4.75 (d, J=5.75 Hz, 1 H) and methine protons; C-9 (numbered 4 above) to δ 4.91 (t, J=4.64 Hz, 1 H), C-11 (numbered 1 above) to δ 3.88-3.95 (m, 1 H), and C15 (numbered 9 above) to δ 3.76 (dd, J=13.71, 2.65 Hz, 1 H).

Key HMBC Correlations Observed

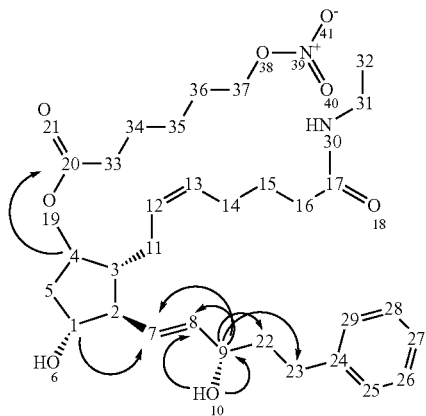

A key correlation for the site of attachment was found in the HMBC spectrum for the proton at C-9 (numbered 4 above) assigned to resonance at δ 4.91 (t, J=4.64 Hz, 1 H) to the carbonyl of the ester (numbered 20 above) at δ 172.27.

LCMS (ESI): m/t 597.2 (M+Na$^+$).

HRMS. Calcd for C$_{29}$H$_{42}$BrNO$_5$Na [M+Na]$^+$: 597.3146. Found: 597.3123.

Example F-3

(1R,3S,4R,5R)-4-[(2Z)-7-(Ethylamino)-7-oxohept-2-en-1-yl]-5-[(1E,3S)-3-hydroxy-5-phenylpent-1-en-1-yl]cyclopentane-1,3-diyl bis[6-(Nitrooxy)hexanoate] (F-3)

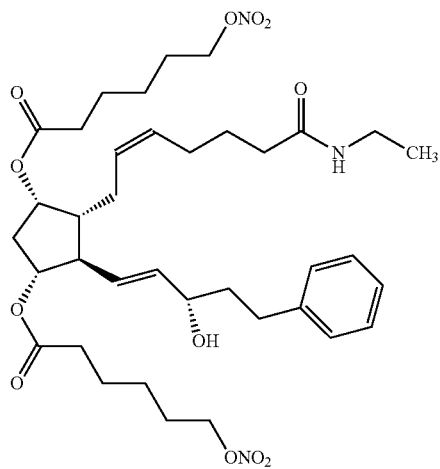

$^1$H NMR (400 MHz, DMSO-d$_6$) δ 7.71 (br. s., 1 H), 7.23-7.32 (m, 2 H), 7.17 (d, J=7.33 Hz, 3 H), 5.44-5.61 (m, 2 H), 5.25-5.38 (m, 2 H), 4.95-5.22 (m, 1 H), 4.84-4.90 (m, 1 H), 4.76-4.83 (m, 1 H), 4.43-4.55 (m, 5 H), 3.86-4.03 (m, 1 H), 2.97-3.10 (m, 2 H), 2.57-2.64 (m, 2 H), 2.54-2.57 (m, 1 H), 2.41-2.48 (m, 1 H), 2.21-2.36 (m, 5 H), 1.84-2.10 (m, 6 H), 1.43-1.72 (m, 12 H), 1.25-1.41 (m, 4 H), 0.99 (t, J=7.33 Hz, 3 H).

HRMS. Calcd. for C$_{37}$H$_{56}$N$_3$O$_{12}$Na[M+Na]$^+$: 756.3679. Found: 756.3646.

Anal. Calcd for C$_{37}$H$_{55}$N$_3$O$_{12}$.0.28H$_2$O: C, 60.04; H, 7.59; N, 5.68. Found: C, 60.03; H, 7.53; N, 5.67.

Example F-4

(1S,2E)-3-[(1R,2R,3S,5R)-2-[(2Z)-7-(Ethylamino)-7-oxohept-2-en-1-yl]-3-hydroxy-6-{[6-(nitro-oxy)hexanoyl]oxy}cyclopentyl]-1-(2-phenylethyl)prop-2-en-1-yl 6-(Nitrooxy)hexanoate (F-4)

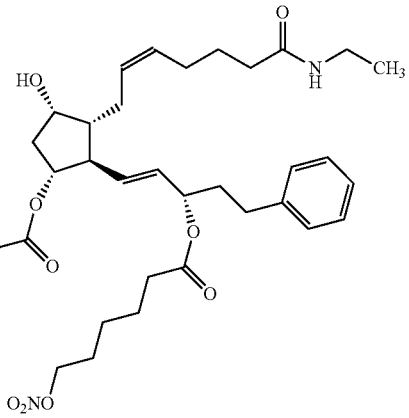

$^1$H NMR (400 MHz, DMSO-d$_6$) δ 7.70 (br. s., 1 H), 7.27 (t, J=7.45 Hz, 2 H), 7.11-7.22 (m, 3 H), 5.35-5.46 (m, 1 H), 5.48-5.57 (m, 2 H), 5.21-5.34 (m, 1 H), 5.09-5.18 (m, 1 H), 4.74-4.85 (m, 1 H), 4.66 (d, J=4.04 Hz, 1 H), 4.48 (dt,

J=12.95, 6.54 Hz, 5 H), 3.89-4.02 (m, 1 H), 2.97-3.09 (m, 2 H), 2.63-2.74 (m, 1 H), 2.55-2.70 (m, 2 H), 2.19-2.37 (m, 6 H), 1.82-2.03 (m, 6 H), 1.57-1.71 (m, 4 H), 1.41-1.57 (m, 8 H), 1.25-1.41 (m, 4 H), 0.98 (t, J=7.20 Hz, 3 H).

HRMS. Calcd. for $C_{37}H_{55}N_3O_{12}Na$ [M+Na]$^+$: 756.3678. Found: 756.3641.

Anal. Calcd for $C_{37}H_{66}N_3O_{12}$-0.08H$_2$O: C, 60.44; H, 7.56; N, 5.71. Found: C, 60.45; H, 7.55; N, 5.67.

added DMAP (39 mg, 0.31 mmol) followed by the slow addition of 4-chlorobutyl chloroformate (43 uL, 0.31 mmol). After 3 days at ambient temperature, the mixture was diluted with DCM and washed with water (1×) and brine (1×). The DCM layer was dried over anhydrous sodium sulfate and concentrated under reduced pressure. The crude mixture of regioisomers and diacylated products was submitted to column chromatography (ethyl acetate-hexane 25-100%, followed by methanol-dichloromethane (5-15%) to provide as the major component isolated, 11-acylated chloride g-1 (25 mg, 15%) as a colorless oil.

LCMS (ES-API): m/z 572.2 (M+Na)$^+$.

Scheme G

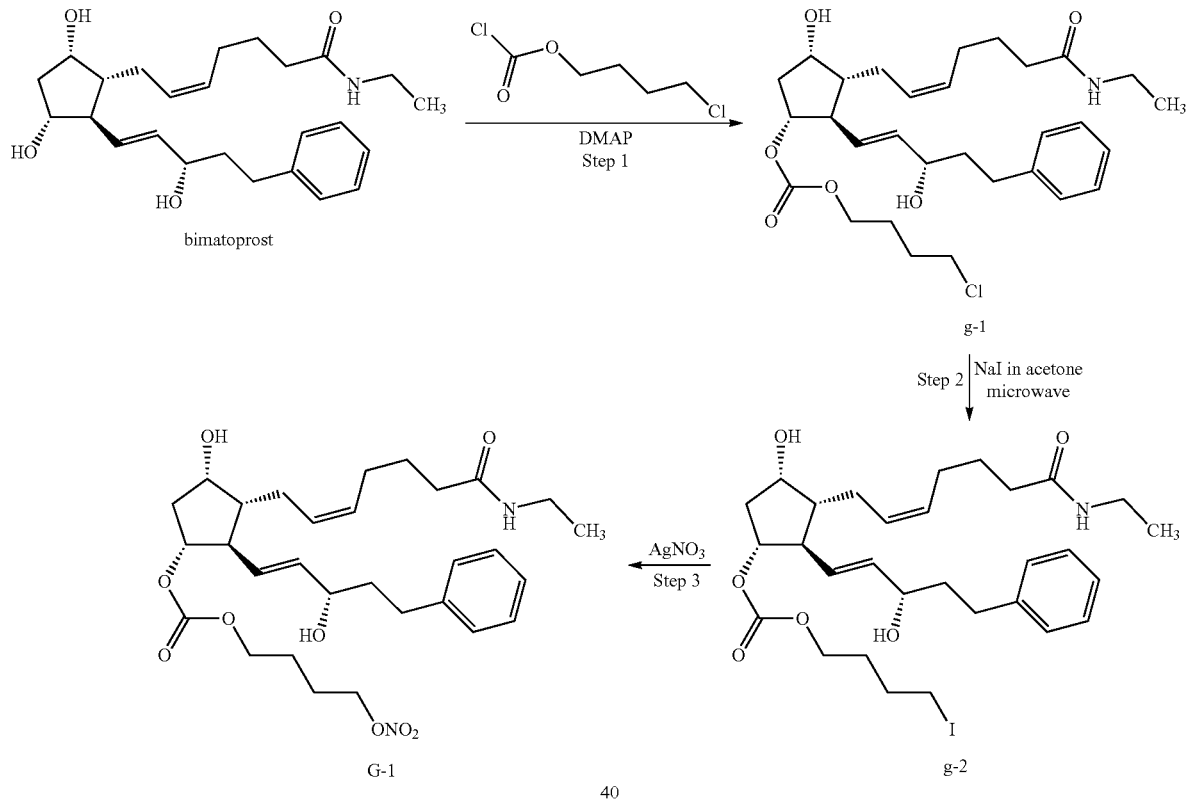

Example G-1

(2R,3R)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butyl Carbonate (G-1)

Step 1: 4-Chlorobutyl (2R,3R)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl Carbonate (g-1)

Step 2: (2R,3R)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-Iodobutyl Carbonate (g-2)

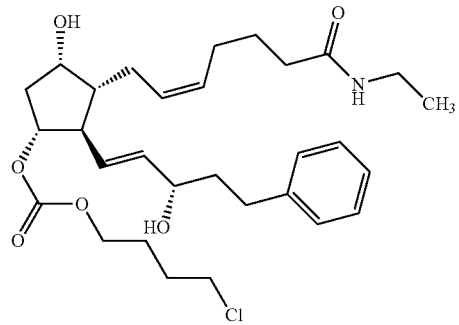

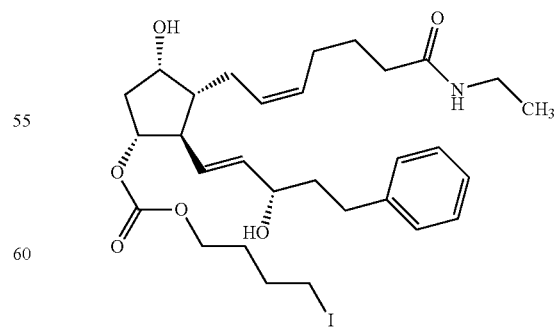

To a solution of bimatoprost (Cayman Chemicals 16820, Lot 188757; 123 mg, 0.30 mmol) in DCM (3 mL) at 0° C. was 4-Chlorobutyl (2R,3R)-3-[(2Z)-7-(ethylamino)-7-oxohept-2-en-1-yl]-4-hydroxy-2-[(1E,3S)-3-hydroxy-5-phenylpent-1-en-1-yl]cyclopentyl carbonate (g-1; 25 mg, 0.045 mmol) was dissolved in acetone (0.9 mL). Sodium iodide (68 mg, 0.45 mmol) was added to the solution. The mix was microwaved at 135° C. for 35 mins and then concentrated under reduced pressure. The residue was dissolved in EA+water. EA phase was separated, washed with brine, dried over anhydrous sodium sulfate and concentrated to give 23 mg (80%) crude iodide g-2, which was used immediately without further purification.

LCMS (ES-API): m/z 664.2 (M+Na)+.

Step 3: (2R,3R)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butyl Carbonate (G-1)

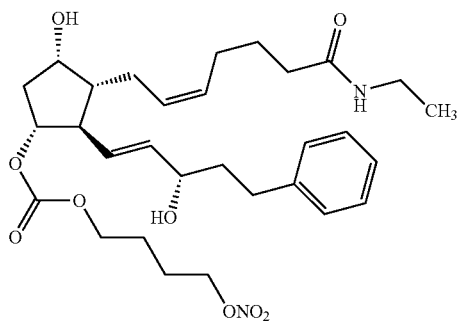

To a solution of (2R,3R)-3-[(2Z)-7-(ethylamino)-7-oxohept-2-en-1-yl]-4-hydroxy-2-[(1E,3S)-3-hydroxy-5-phenyl-pent-1-en-1-yl]cyclopentyl 4-iodobutyl carbonate (g-2; 23 mg, 0.036 mmol) in MeCN (0.72 mL) was added silver nitrate (18 mg, 0.108 mmol). After stirring at ambient temperature overnight, the mixture was filtered through a pad of Celite. The solid was washed with ACN. The filtrate was concentrated and residue was dissolved in EtOAc+water. The EtOAc phase was washed with brine (1×), dried over anhydrous sodium sulfate and concentrated to give a crude mixture, which was then purified by preparative reverse phase HPLC (water:acetonitrile, with 0.1% acetic acid) to give 8.0 mg desired product (42%).

$^1$H NMR (400 MHz, DMSO-d$_6$) δ 0.98 (t, J=7.33 Hz, 3 H), 1.35-1.57 (m, 4 H), 1.58-1.74 (m, 6 H), 1.90-2.03 (m, 5 H), 2.03-2.17 (m, 1 H), 2.34 (ddd, J=14.65, 9.09, 5.31 Hz, 1 H), 2.42-2.49 (m, 1 H), 2.52-2.63 (m, 2 H), 2.96-3.09 (m, 2 H), 3.85-3.98 (m, 2 H), 3.99-4.14 (m, 2 H), 4.44-4.57 (m, 2 H), 4.62-4.74 (m, 2 H), 4.78 (d, J=4.55 Hz, 1 H), 5.29 (dt, J=10.67, 7.17 Hz, 1 H), 5.37-5.55 (m, 3 H), 7.10-7.20 (m, 3 H), 7.21-7.32 (m, 2 H), 7.70 (t, J=5.05 Hz, 1 H).

LCMS (ES-API): m/z 599.2 (M+Na)+.

HRMS (TOF): calcd for C$_{30}$H$_{44}$N$_2$O$_9$Na[MNa]+: 599.29390. Found: 599.29203.

Example G-2

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 4-(Nitrooxy)butyl carbonate (G-2)

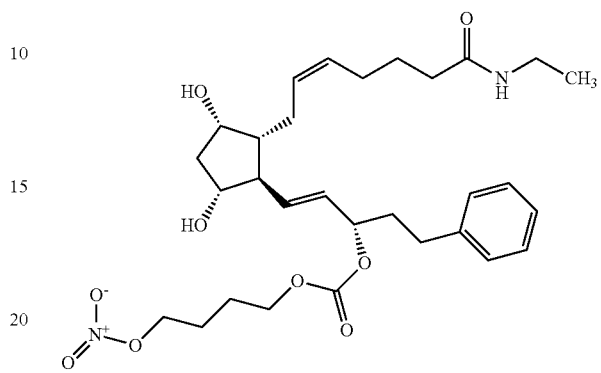

Prepared along a route similar to that of Example G-1, except using boronate b-1 to acylate with 3-chloropropyl chloroformate (100% crude yield), exchange with NaI in acetone (22%), nitration with silver nitrate, and preparative HPLC to give 55 mg (49%) of carbonate G-2 as a colorless oil.

$^1$H NMR (400 MHz, DMSO-d$_6$) δ 0.98 (t, J=7.33 Hz, 3 H), 1.27-1.39 (m, 1 H), 1.39-1.55 (m, 3 H), 1.60-1.83 (m, 4 H), 1.80-2.03 (m, 7 H), 2.04-2.26 (m, 3 H), 2.60 (t, J=7.83 Hz, 2 H), 2.97-3.10 (m, 2 H), 3.60-3.74 (m, 2 H), 3.91 (br. s., 1 H), 4.02-4.16 (m, 2 H), 4.35-4.48 (m, 1 H), 4.54 (t, J=6.19 Hz, 1 H), 4.57-4.69 (m, 1 H), 4.97 (q, J=6.74 Hz, 1 H), 5.20-5.33 (m, 1 H), 5.37-5.63 (m, 3 H), 7.12-7.22 (m, 3 H), 7.23-7.35 (m, 2 H), 7.63-7.77 (m, 1 H).

LCMS (ESI): m/z 599.2 (M+Na)+.

Anal. Calcd for C$_{30}$H$_{44}$N$_2$O$_9$·0.4C$_6$H$_{10}$: C, 63.84; H, 7.94; N, 4.38. Found: C, 63.66; H, 8.13; N, 4.38.

Scheme H

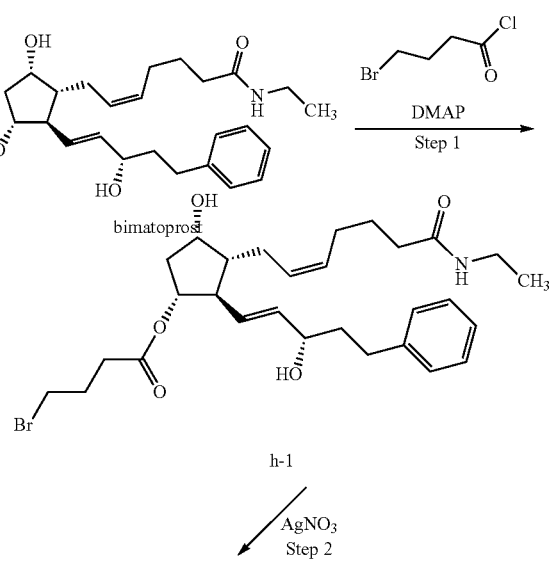

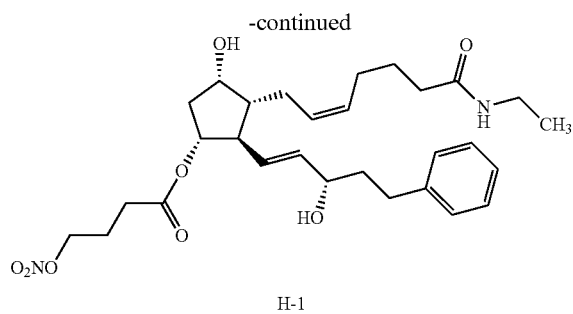

H-1

Example H-1

(1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butanoate

Step 1: (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-Bromobutanoate (h-1)

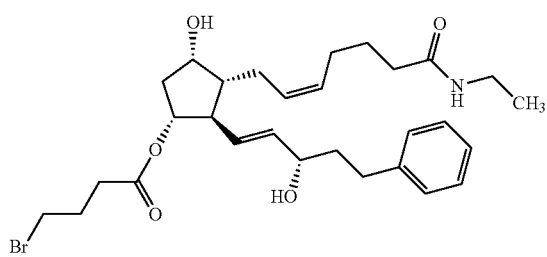

To a suspension of bimatoprost (Cayman Chemicals; 540 mg, 1.30 mmol) in anhydrous dichloromethane (5.2 mL) at 0° C. was added DMAP (850 mg, 1.33 mmol) and 4-bromobutyryl chloride (0.154 ml, 0.32 mmol) and allowed to stir for 72 h. The resultant mixture was filtered and solvent removed by nitrogen flow. The residue was redissolved in dichloromethane, washed with saturated $NaHCO_3$ and brine, and dried over $MgSO_4$ to give a crude mixture, which was submitted to preparative reverse phase HPLC to give as a major separable pure component, 11-bromoester h-1 as a colorless oil, 42 mg (6%).

$^1$H NMR (400 MHz, DMSO-$d_6$) δ 7.70 (bs., 1 H), 7.22-7.32 (m, 2 H), 7.10-7.21 (m, 3 H), 5.37-5.54 (m, 3 H), 5.20-5.35 (m, 1 H), 4.72-4.86 (m, 2 H), 4.57-4.66 (m, 1 H), 3.84-4.01 (m, 2 H), 3.51 (t, J=6.57 Hz, 2 H), 2.96-3.10 (m, 2 H), 2.54-2.66 (m, 2 H), 2.21-2.45 (m, 4 H), 2.05-2.21 (m, 1 H), 1.89-2.04 (m, 7 H), 1.57-1.73 (m, 2 H), 1.30-1.54 (m, 4 H), 0.98 (t, J=7.33 Hz, 3 H).

LCMS (ESI): m/z 588.2 (M+Na)$^+$.

HRMS: Calcd for $C_{29}H_{42}BrNO_5Na$ [M+Na]$^+$: 586.2138. Found: 586.2132.

Step 2: (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butanoate

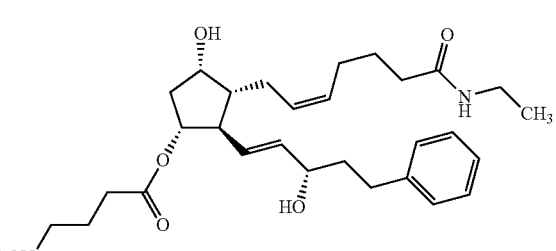

To (1R,2R,3R,4S)-3-[(2Z)-7-(ethylamino)-7-oxohept-2-en-1-yl]-4-hydroxy-2-[(1E,3S)-3-hydroxy-5-phenylpent-1-en-1-yl]cyclopentyl 4-bromobutanoate (h-1; 40 mg, 0.071 mmol) in acetonitrile (0.3 mL) was added silver nitrate (36 mg, 0.213 mmol). After 18 h at ambient temperature, the mix was filtered through Celite, which was washed with acetonitrile (10 mL). The filtrate was concentrated, dissolved in ethyl acetate (15 mL), and washed with brine (2×3 mL). The concentrate was purified by preparative reverse phase HPLC to yield 19 mg (49%) of nitrate H-1 as a colorless oil.

$^1$H NMR (400 MHz, DMSO-$d_6$) δ 7.71 (bs., 1 H), 7.26 (t, J=7.45 Hz, 2 H), 7.10-7.19 (m, 3 H), 5.37-5.51 (m, 3 H), 5.21-5.35 (m, 1 H), 4.70-4.83 (m, 2 H), 4.63 (d, J=4.04 Hz, 1 H), 4.51 (t, J=6.57 Hz, 2 H), 3.86-3.99 (m, 2 H), 2.96-3.10 (m, 2 H), 2.53-2.64 (m, 3 H), 2.26-2.41 (m, 3 H), 2.05-2.17 (m, 1 H), 1.81-2.05 (m, 7 H), 1.59-1.74 (m, 2 H), 1.34-1.54 (m, 4 H), 0.98 (t, J=7.20 Hz, 3H).

LCMS (ESI): m/z 569.2 (M+Na$^+$).

HRMS: Calcd for $C_{29}H_{42}N_2O_3Na$ [M+Na]$^+$: 569.2833. Found: 569.2822.

Scheme J

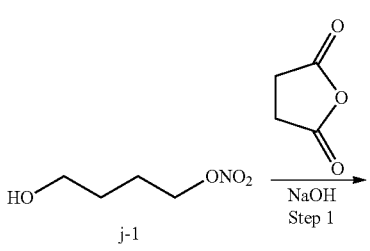

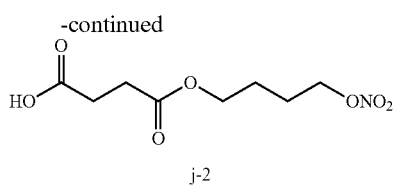

j-2

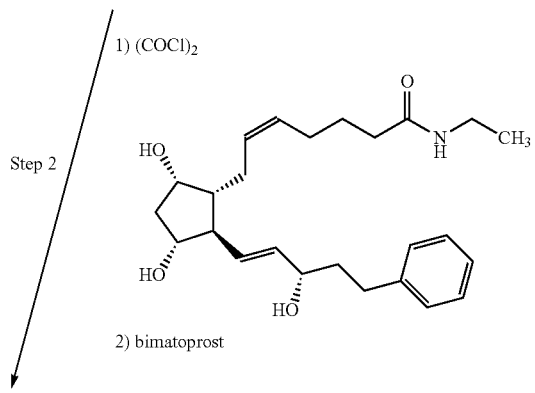

1) (COCl)₂

Step 2

2) bimatoprost

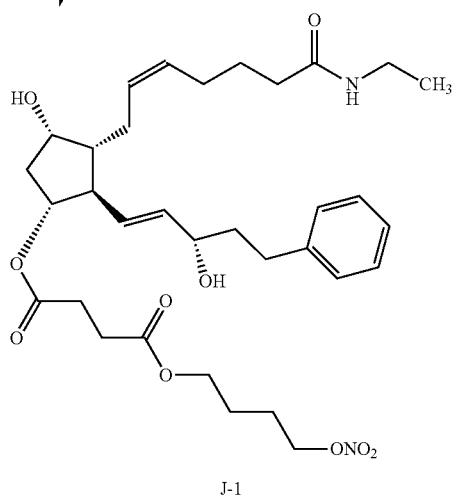

J-1

Example J-1

(1R,2R,3R,4S)-3-[(2Z)-7-(Ethylamino)-7-oxohept-2-en-1-yl]-4-hydroxy-2-[(1E,3S)-3-hydroxy-5-phenyl-pent-1-en-1-yl]cyclopentyl 4-(Nitrooxy)butyl butanedioate

Step 1: 4-[4-(Nitrooxy)butoxy]-4-oxobutanoic Acid (j-2)

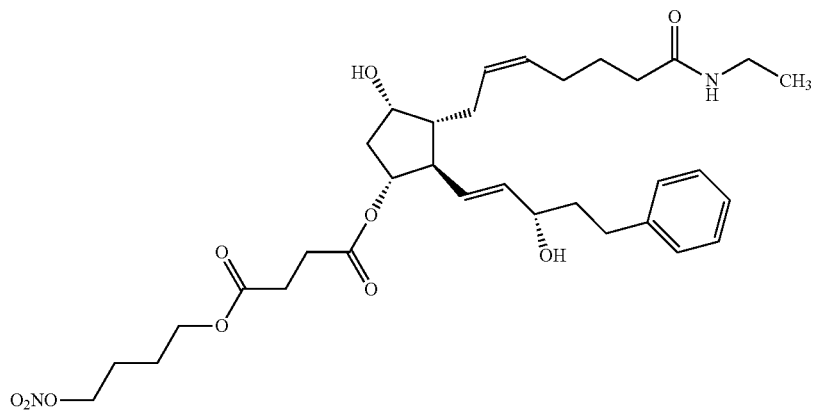

To a solution of crude 4-hydroxybutyl nitrate (j-1); 0.889 g, 3.78 mmol; patent application US2006/189603 A1) in t-BuOH (19 mL) with triethylamine (0.79 mL, 5.6 mmol) was added succinic anhydride (0.790 g, 7.90 mmol) and allowed to stir at ambient temperature for 12 h. A solution of 2.5% aq $H_3PO_4$ was added. After extraction with dichloromethane (3×50 mL), the combined organic layer was dried over $MgSO_4$, filtered, and solvent removed under reduced pressure. The residue was purified with a Biotage with silica gel, eluting with a gradient of 5%-20% EtOAc in $CH_2Cl_2$ to yield succinate j-2 as colorless oil (820 mg, 92%), which was used without further purification.

$^1$H NMR (400 MHz, DMSO-$d_6$) δ 12.23 (s, 1 H), 4.49-4.58 (m, 2 H), 4.00-4.08 (m, 2 H), 2.43-2.49 (m, 4 H), 1.59-1.77 (m, 4 H)

Step 2: (1R,2R,3R,4S)-3-[(2Z)-7-(Ethylamino)-7-oxonept-2-en-1-yl]-4-hydroxy-2-[(1E,3S)-3-hydroxy-5-phenylpent-1-en-1-yl]cyclopentyl 4-(Nitrooxy)butyl butanedioate (J-1)

Crude 4-[4-(nitrooxy)butoxy]-4-oxobutanoic acid (30 mg, 0.13 mmol) was dissolved in anhydrous dichloromethane (1.28 mL) under $N_2$ at room temperature. The solution was cooled to 0° C. and successively added anhydrous DMF (0.25 mL) and oxalyl chloride (10 uL, 0.128 mmol). After stirring at ambient temperature for 12 h, the mixture was filtered through a silica plug, which was washed with anhydrous dichloromethane (5 mL). The solvent was removed to yield 32 mg (100%) of presumed acid chloride (4-(nitrooxy)butyl 4-chloro-4-oxobutanoate) as a colorless oil, which was immediately used without further characterization or purification.

To a suspension of bimatoprost (Cayman Chemicals; 25 mg, 0.024 mmol) in dichloromethane at 0° C. was added DMAP resin (Argonaut (Biotage "PS-DMAP"); 30 mg of 1.6 mmol/g, 0.024 mmol) and the above crude 4-(nitrooxy)butyl 4-chloro-4-oxobutanoate. After 20 min at 0° C., the cooling bath was removed, and allowed to stir at ambient temperature for 72 h. The resin was filtered off, and the filtrate was concentrated, and gave a crude mixture as an oil, which was purified by flash chromatography with a Biotage instrument, eluting with a gradient of EtOAc with $CH_2Cl_2$, 25-100%, to yield 19 mg (30%) of J-1 as a colorless oil.

$^1$H NMR (400 MHz, DMSO-$d_6$) δ 7.70 (s, 1H), 7.26 (t, J=7.45 Hz, 2 H), 7.17 (d, J=7.83 Hz, 3 H), 5.76 (s, 2 H), 5.36-5.52 (m, 3 H), 5.31 (s, 1 H), 4.75 (d, J=4.80 Hz, 2 H), 4.62 (d, J=4.04 Hz, 1 H), 4.48-4.58 (m, 4 H), 3.93 (d, J=18.44 Hz, 2 H), 2.96-3.09 (m, 2 H), 2.63-2.71 (m, 1 H), 2.56 (d, J=1.77 Hz, 3 H), 2.22-2.36 (m, 2 H), 1.96 (s, 2 H), 1.56-1.80 (m, 10 H), 1.34-1.53 (m, 4 H), 0.98 (t, J=7.20 Hz, 3 H).

LCMS (ESI): m/z 655.2 (M+Na)$^+$.

HRMS: Calcd for $C_{33}H_{48}N_2O_{10}Na$ [M+Na]$^+$ 655.3201. Found: 655.3180.

Example J-2

(1R,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 4-(Nitrooxy)butyl Butanedioate

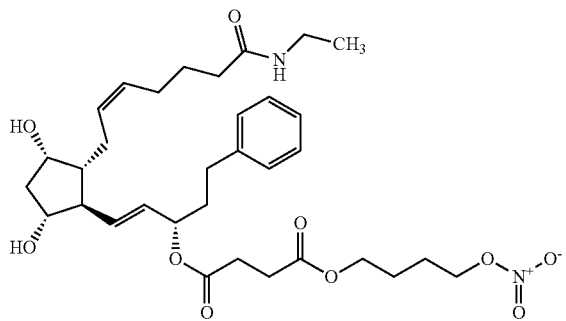

In a similar manner to that for Example J-1, acid j-2 was coupled to protected bimatoprost boronate b-1 and purified via chromatography with a Biotage to furnish 133 mg (18.1%) of 15-ester nitrate J-2 as a colorless oil.

$^1$H NMR (700 MHz, DMSO-$d_6$) δ 0.98 (t, J=7.30 Hz, 3H), 1.21-1.32 (m, 2H), 1.42 (dd, J=15.48, 3.98 Hz, 2H), 1.44-1.55 (m, 4H), 1.56-1.70 (m, J=7.35, 7.35, 7.19, 6.86 Hz, 4H), 1.85-2.05 (m, 5H), 2.05 2.17 (m, 1H), 2.25 (t, J=7.30 Hz, 2H), 2.33 (ddd, J=14.82, 9.29, 5.53 Hz, 1H), 2.46 (ddd, J=11.83, 8.07, 7.96 Hz, 1H), 2.54-2.65 (m, 2H), 2.95-3.08 (m, 2H), 3.84-4.00 (m, 2H), 4.46 (t, J=6.63 Hz, 2H), 4.61 (d, J=3.98 Hz, 1H), 4.77 (ddd, J=12.27, 4.53, 4.42 Hz, 2H), 5.21-5.35 (m, 1H), 5.36-5.55 (m, 3H), 7.16 (d, J=7.52 Hz, 3H), 7.25 (t, J=7.74 Hz, 2H), 7.70 (t, J=4.64 Hz, 1H).

HRMS. Calcd. for $C_{31}H_{46}N_2O_8Na$ [M+Na]$^+$: 597.3146. Found: 597.3133.

Anal. Calcd for $C_{31}H_{46}N_2O_8 \cdot 0.33H_2O$: C, 64.12; H, 8.10; N, 4.82. Found: C, 64.11; H, 8.07; N, 4.80.

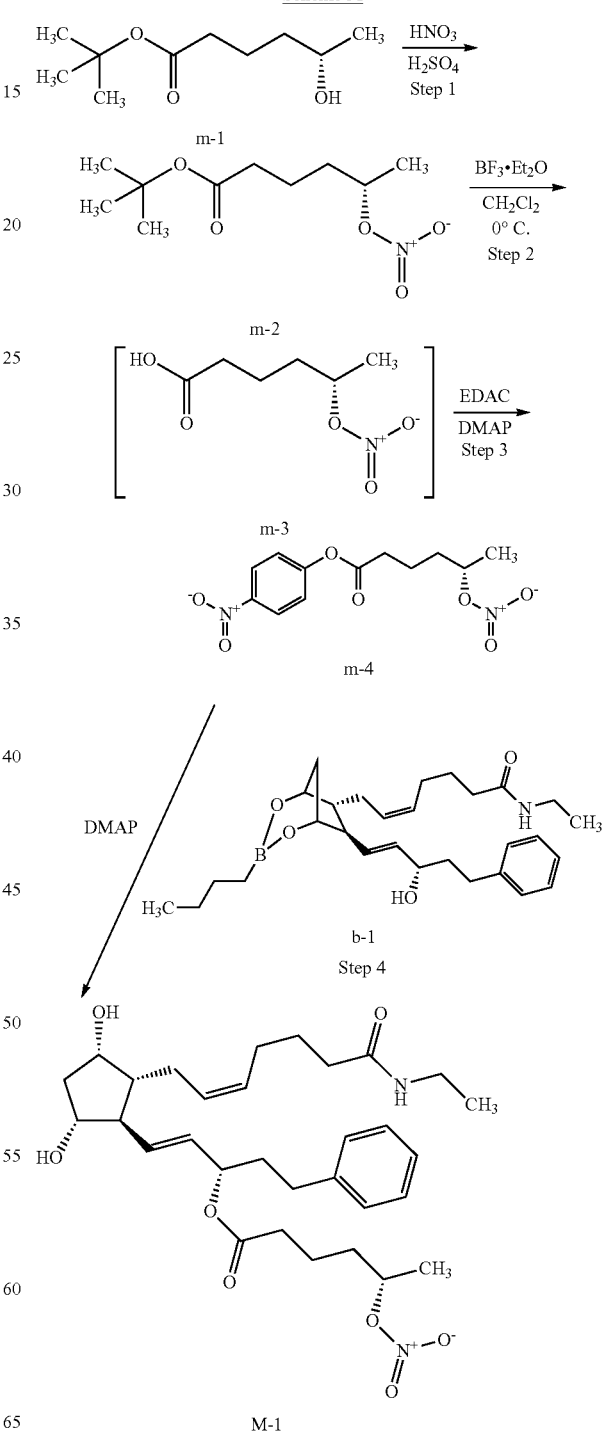

Scheme M

Example M-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy)hexanoate

Step 1: (R)-tert-Butyl 5-Nitrooxyhexanoate (m-2)

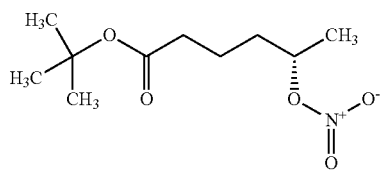

To a solution of HNO$_3$ (8.40 mL, 188 mmol) in acetic anhydride (20 mL) at 0° C. was slowly added a solution of (R)-tert-butyl 5-hydroxyhexanoate (m$^{-1}$; Pamies, O.; Backvall, J. E. *J. Org. Chem.* 2002, 67, 1261-1265; 5.84 g, 31 mmol) in CH$_2$Cl$_2$ (20 mL). The mixture stirred at 0° C. for 15 min, then poured into iced 10% aq NaOH. The organic layer was separated, then washed with H$_2$O, NaHCO$_3$ and brine, dried over Na$_2$SO$_4$, and concentrated. The crude residue was then purified by flash chromatography eluting with a gradient of 0/100 to 20/80 ethyl acetate/hexane to give the desired t-butyl ester m$^{-2}$, which was used without further purification.

$^1$H-NMR (300 MHz, CDCl$_3$): δ 5.09 (m, 1H); 2.25 (m, 2H); 1.69 (m, 4H); 1.45 (s, 9H); 1.38 (d, 3H, J=6.2 Hz).

Step 2: (R)-5-Nitrooxyhexanoic Acid (m-3)

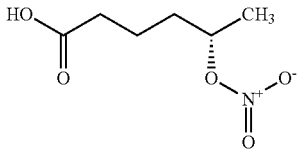

To a solution of crude (R)-tert-butyl 5-nitrooxyhexanoate (31 mmol) in CH$_2$Cl$_2$ (50 mL) at 0° C., was added BF$_3$.Et$_2$O (5.1 mL, 40 mmol). After 1 hour, the mixture was then washed with brine, dried over Na$_2$SO$_4$, and the volume of the solvent reduced. The resultant solution was used in the following step without further purification.

$^1$H-NMR (300 MHz, CDCl$_3$): δ 5.11 (m, 1H); 2.43 (m, 2H); 1.75 (m, 4H); 1.39 (d, 3H, J=6.2 Hz).

Step 3: (R)-4-Nitrophenyl 5-Nitrooxyhexanoate (m-4)

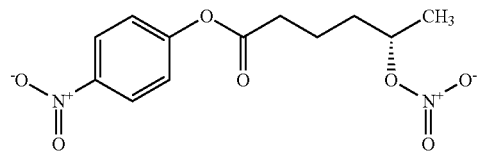

A solution of (R)-5-nitrooxyhexanoic acid (1.50 g, 8.57 mmol), 4-nitrophenol (1.20 g, 8.57 mmol), N-(3-dimethylaminopropyl)-N'-ethylcarbodiimide hydrochloride (EDAC; 2.00 g, 10.3 mmol), and DMAP (cat. amount) in CH$_2$Cl$_2$ (20 mL) stirred at ambient temperature for 3 days and solvent removed under reduced pressure to give the crude product, which was then purified by flash chromatography eluting with a gradient of 0/100 to 20/80 ethyl acetate/hexane to give phenyl ester m-4 (780 mg, 31%), which was used without further purification.

$^1$H-NMR (300 MHz, CDCl$_3$): δ 8.25 (d, 2H); 7.27 (d, 2H); 5.12 (m, 1H); 2.67 (m, 2H); 1.83 (m, 4H); 1.40 (d, 3H, J=6.2 Hz)

Step 4: (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy)hexanoate

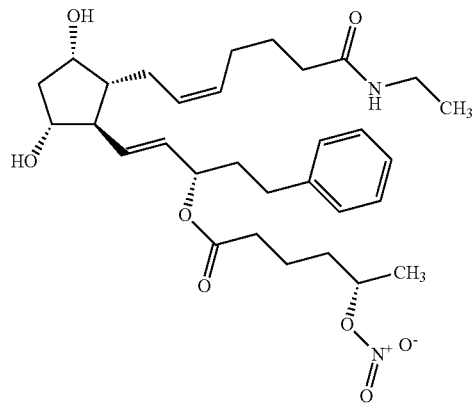

A solution of (5Z)-7-{(6R,7R)-3-butyl-7-[(1E,3S)-3-hydroxy-5-phenylpent-1-en-1-yl]-2,4-dioxa-3 borabicyclo [3.2.1]oct-6-yl}-N-ethylhept-5-enamide (380 mg, 0.79 mmol), (R)-4-nitrophenyl 5-nitrooxyhexanoate (780 mg, 2.61 mmol) and DMAP (320 mg, 2.61 mmol) in CH$_2$Cl$_2$ (20 mL) stirred at ambient temperature for 1 day. The solvent was removed under reduced pressure to give an oil, which was then dissolved in MeOH and stirred at ambient temperature overnight. The solvent was removed under reduced pressure to give a pale yellow oil, which was then purified by flash chromatography eluting with a gradient of 20/80 to 70/30 acetone/hexane followed by purification by preparative reverse phase HPLC (ammonium acetate 10 mM:acetonitrile) to give the desired product (310 mg, 69%).

$^1$H-NMR (300 MHz, DMSO-d$_6$): δ 7.68 (1H, t); 7.25 (2H, m); 7.17 (3H, m); 5.48 (3H, m); 5.35-5.05 (3H, m); 4.57 (1H, d); 4.39 (1H, d); 3.90 (1H, m); 3.67 (1H, m); 3.03 (2H, m); 2.59 (2H, t); 2.33 (2H, t); 2.15 (4H, m); 1.96 (7 H; m); 1.70-1.40 (7H, m); 1.30 (3H, d); 1.00 (3H, t).

Scheme K

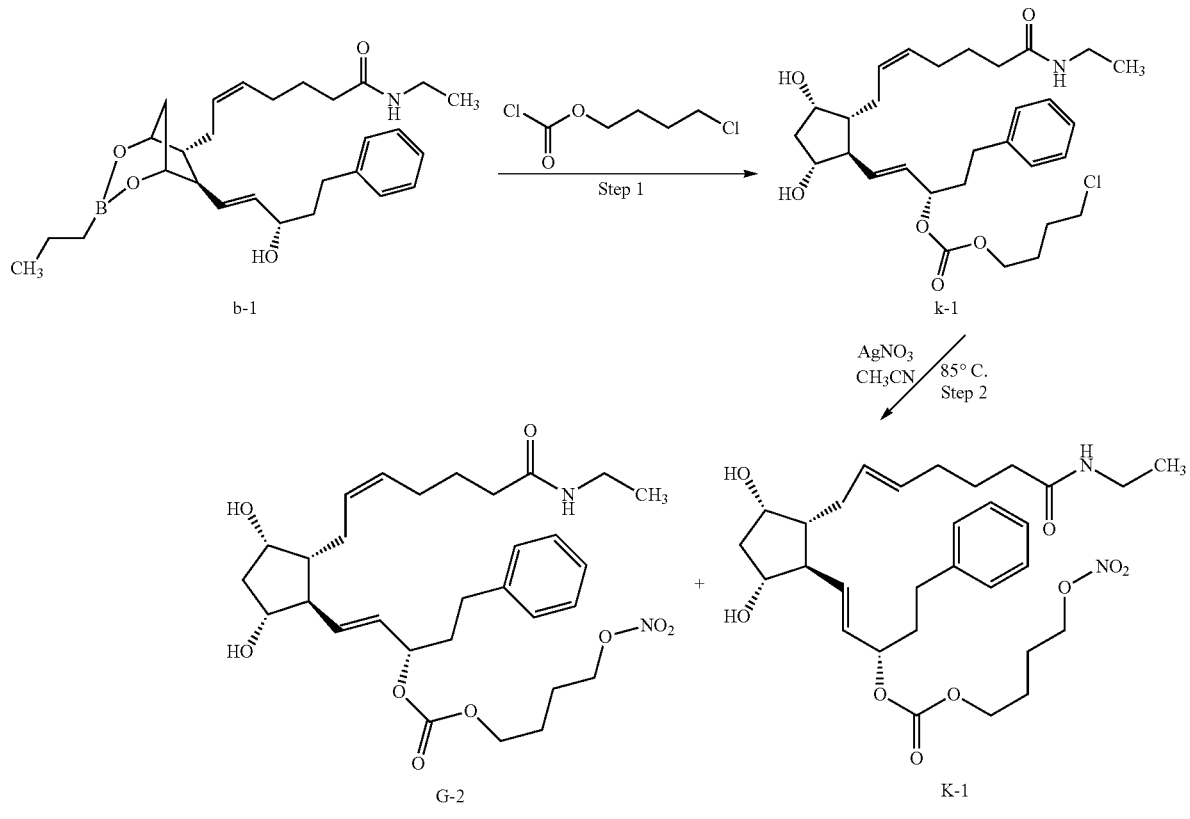

Example K-1

(1S,2E)-3-{(1R,2R,3S,5R)-2-[(2E)-7-(Ethylamino)-7-oxohept-2-en-1-yl]-3,5-dihydroxycyclopentyl}-1-(2-phenylethyl)prop-2-en-1-yl 4-(Nitrooxy)butyl carbonate

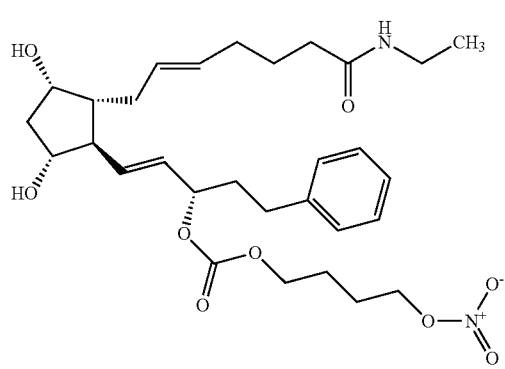

Isolated as significant by-product from an early attempt to optimize intended cis-carbonate Example G-2.

Step 1: 4-Chlorobutyl (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl Carbonate (k-1)

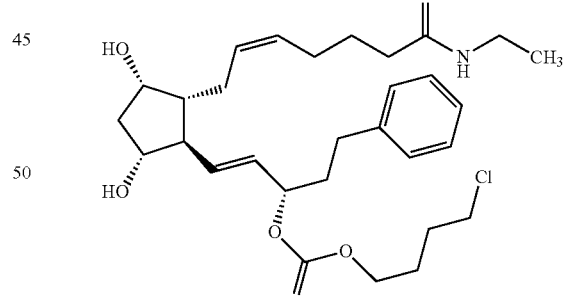

To a solution of bimatoprost boronate b-1 (529 mg, 1.10 mmol) in THF was added DMAP (6.9 mg, 0.055 mmol). The solution was cooled to 0° C. and successively slowly added pyridine (0.22 mL, 2.75 mmol) and 4-chlorobutyl chloroformate (0.375 mL, 2.75 mmol). Allowed to stir at ambient temperature over 2 days. Added more pyridine (89 uL, 1.11 mmol) and 4-chlorobutyl chloroformate (150 uL, 1.10 mmol) and stirred for another 24 h. The resultant mixture was concentrated under reduced pressure, residue partitioned with ethyl acetate and water. Washed organic layer with brine, dried over sodium sulfate, filtered, and concentrated in vacuo to provide 808 mg (134%) of a crude oil, which was used without further purification.

¹H NMR (400 MHz, CDCl₃) δ 0.62-0.71 (m, 1H), 0.88 (t, J=7.1 Hz, 2H), 1.11 (t, J=7.2 Hz, 2H), 1.22-1.38 (m, 3H), 1.57 (s, 2H), 1.64-1.77 (m, 2H), 1.77-1.92 (m, 4H), 1.86 (dq, J=10.5, 10.3 Hz, 2H), 1.96 (q, J=3.2 Hz, 1H), 2.01-2.15 (m, 3H), 2.17-2.34 (m, 1H), 2.64 (t, J=7.1 Hz), 3.26 (dd, J=7.2, 5.7 Hz, 1H), 3.53-3.62 (m, 1H), 3.58 (t, J=6.1 Hz, 3H), 4.17 (dt, J=7.8, 6.1 Hz, 2H), 5.34-5.59 (m, 3H), 7.11-7.22 (m, 2H), 7.27-7.34 (m, 1H).

LCMS (ESI) (M+Na⁺): 573.2.

Step 2

Example K-1

(1S,2E)-3-{(1R,2R,3S,5R)-2-[(2E)-7-(Ethylamino)-7-oxohept-2-en-1-yl]-3,5-dihydroxycyclopentyl}-1-(2-phenylethyl)prop-2-en-1-yl 4-(Nitrooxy)butyl carbonate

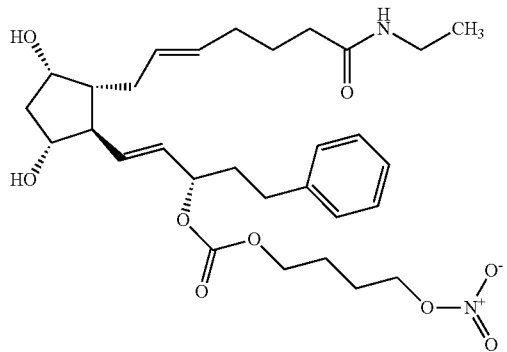

A mixture of chlorocarbonate k-1 (686 mg, 1.25 mmol) and silver nitrate (636 mg, 3.74 mmol) in acetonitrile (12.5 mL) stirred at 82° C. overnight. More silver nitrate (318 mg, 1.87 mmol) was added, another 5 h at 82° C., then allowed to stir at ambient temperature for 4 days. The resultant mix was filtered through Celite that was rinsed with dichloromethane. The filtrate was evaporated under reduced pressure, residue dissolved in dichloromethane, and washed with water and brine. The extract was concentrated in vacuo to give 611 mg of yellow-brown oil, which was purified with preparative SFC to provide 55 mg (7.6%) of intended cis G-2 as a pale yellow oil and 182 mg (25.3%) of trans-K-1 as pale yellow oil.

¹H NMR (400 MHz, DMSO-d₆) δ 0.97 (t, J=7.20 Hz, 3 H), 1.27-1.56 (m, 4 H), 1.59-1.80 (m, 4 H), 1.80-2.04 (m, 7 H), 2.04-2.28 (m, 3 H), 2.60 (t, J=7.83 Hz, 2 H), 2.96-3.09 (m, 2 H), 3.66 (t, J=6.32 Hz, 2 H), 3.92 (br. s., 1 H), 4.09 (t, J=5.81 Hz, 2 H), 4.38 (br. s., 1 H), 4.54 (t, J=6.06 Hz, 1 H), 4.60 (br. s., 1 H), 4.96 (q, J=6.65 Hz, 1 H), 5.26-5.38 (m, 1 H), 5.39-5.59 (m, 3 H), 7.12-7.23 (m, 3 H), 7.23-7.33 (m, 2 H), 7.70 (br. s., 1 H).

HRMS. Calcd for C₃₀H₄₄N₂O₉Na (M+Na): 599.2945 Found: 599.2911.

Example M-2

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy) hexanoate

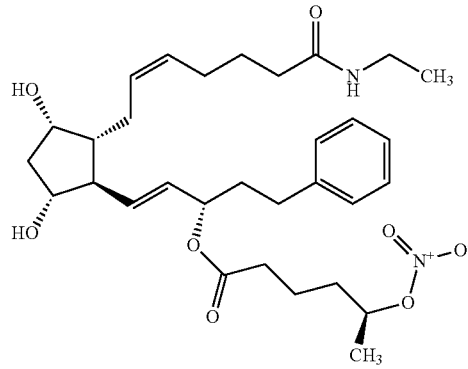

Prepared following a similar route as shown in Scheme M for Example M-1, instead starting from (S)-tert-butyl 5-hydroxyhexanoate (Pamies, O.; Backvall, J. E. *J. Org. Chem.* 2002, 67, 1261-1265).

¹H-NMR (300 MHz, DMSO-d₆): δ 7.68 (1H, t); 7.25 (2H, m); 7.17 (3H, m); 5.48 (3H, m); 5.35-5.05 (3H, m); 4.57 (1H, d); 4.39 (1H, d); 3.90 (1H, m); 3.67 (1H, m); 3.03 (2H, m); 2.59 (2H, t); 2.33 (2H, t); 2.15 (4H, m); 1.96 (7H; m); 1.70-1.40 (7H, m); 1.30 (3H, d); 1.00 (3H, t).

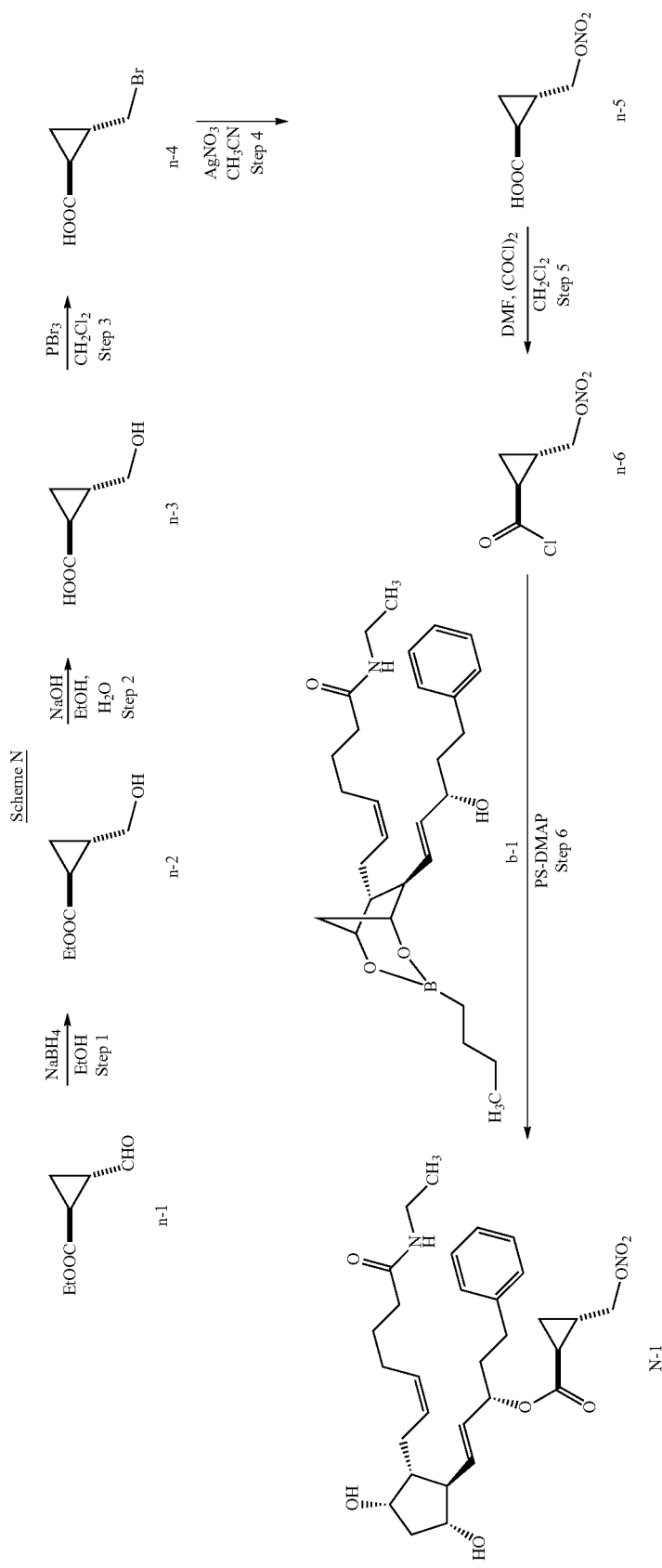

Example N-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl trans-2-[(Nitrooxy)methyl]cyclopropanecarboxylate

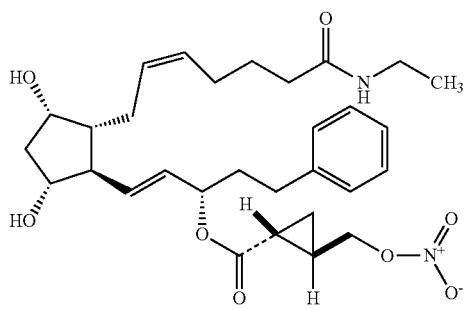

Step 1: Ethyl trans-2-Hydroxymethyl-1-cyclopropanecarboxylate (n-2)

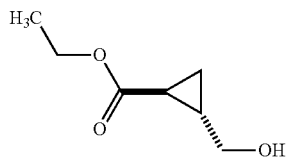

As described in Kajiwara, T.; Nakatomi, T.; Sasaki, Y.; Hatanaka, A. *Agric. Biol. Chem.* 1980, 44, 2099-2104, to a solution of ethyl trans-2-formyl-1-cyclopropane carboxylate (n-1; Aldrich; 335 g, 2.36 mol) in ethanol (2L) in a vessel cooled in an ice bath was added portionwise sodium borohydride (44.6 g, 1.18 mol). After 2h stirring at ambient temperature, water (1L) was carefully added dropwise. The resultant solution was concentrated to remove the ethanol and extracted with ethyl acetate (2×1L). The organic layers were dried over MgSO$_4$, filtered, and evaporated to give 313 g (92%) of alcohol n-2 as a colorless liquid, which had an NMR that matched reported (Ando, W.; Imai, I.; Migita, T. *J. Org. Chem.* 1972, 37, 3596-3600) and was used without further purification.

Step 2: trans-2-Hydroxymethyl-1-cyclopropanecarboxylic Acid (n-3)

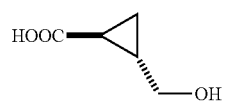

To a solution of ethyl trans-2-hydroxymethyl-1-cyclopropanecarboxylate (n-2; 313 g, 2.17 mol) in ethanol (1L) was slowly added a solution of sodium hydroxide (130 g, 3.26 mol) in water (1.3 L). The resultant solution stirred at ambient temperature for 48h. Ethanol was removed under reduced pressure, then brought to pH ~2 with 2M aq HCl and extracted with ethyl acetate (4L). The organic extract was washed with brine, dried over Na$_2$SO$_4$, filtered, and evaporated under reduced pressure to furnish 144 g (~57%) of acid n-3 as a white solid, which was used without further purification and whose NMR matched that reported (NMR of chiral isomers; see supplementary material for Wellendorph, P.; Hog, S.; Greenwood, J. R.; de Lichtenberg, A.; Nielsen, B.; Frolund, B.; Brehm, L.; Clausen, R. P.; Brauner-Osborne, H. *J Pharmacol Exp Ther* 2005, 315, 346-351).

Step 3: trans-2-Bromomethyl-1-cyclopropanecarboxylic Acid (n-4)

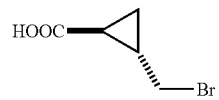

Similar to that reported in D'Yakonov, I. A.; Guseva, O. V. *Sbornik Statei Obshchei Khim., Akad. Nauk S.S.S.R.* 1953, 1, 425-33; Chem. Abstr.; 1955; 882, to a mechanically stirred solution of trans-2-hydroxymethyl-1-cyclopropanecarboxylic acid (n-3; 144 g, 1.24 mol) in CH$_2$Cl$_2$ (1L) was added dropwise PBr$_3$ (111 g, 0.413 mol). After 1h at ambient temperature, CH$_2$Cl$_2$ was removed under reduced pressure to give an oil, which was cooled in an ice bath. Water was added dropwise. The mixture was extracted with ethyl acetate (3×1L). The organic extracts were pooled, dried over MgSO4, filtered and evaporated under reduced pressure to an oil, which was purified via column chromatography with silica gel eluting with EtOAc:hexanes; 1:10) to afford 136 g (60%) of bromide n-4 as white crystals, which was used without further purification.

$^1$H NMR (400 MHz, CDCl$_3$): δ 1.03 (m, 1H), 1.48 (m, 1H), 1.63 (m, 1H), 1.99 (m, 1H), 3.37 (m, 2H), 12.05 (s, 1H).

ESI MS: m/z 178.66; 176.69.

Anal. Calcd for C$_5$H$_7$O$_2$Br: C, 33.55; H, 3.94. Found: C, 34.09; H, 3.83.

Step 4: trans-2-Nitroxymethyl-1-cyclopropanecarboxylic Acid (n-5)

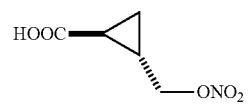

Silver nitrate was added to a solution of trans-2-(bromomethyl)cyclopropanecarboxylic acid (n-4; 4.48 g, 25 mmol) in acetonitrile (25 mL). The mixture immediately turned white, then became a light green suspension. After 72 h at ambient temperature, the resultant mixture was filtered through Celite, which was washed with acetonitrile. The filtrate was concentrated, then extracted with EtOAc (3×200 mL). The combined organic extracts were washed with water and brine, dried over MgSO$_4$, filtered, concentrated, and dried under vacuum to give 3.765 g (93%) of the nitrate n-5 as a white solid, which was used without further purification.

$^1$H NMR (400 MHz, DMSO-d$_6$) δ 12.36 (s, 1 H), 4.53 (dd, J=11.24, 6.95 Hz, 1 H), 4.38 (dd, J=11.24, 7.96 Hz, 1 H), 1.51-1.75 (m, 2 H), 0.93-1.15 (m, 2 H).

Step 5: trans-2-(Chlorocarbonyl)cyclopropylimethyl Nitrate (n-6)

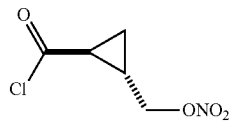

trans-2-[(Nitrooxy)methyl]cyclopropanecarboxylic acid (n-5; 967 mg, 6.00 mmol) was dissolved in anhydrous $CH_2Cl_2$ (60 mL) under $N_2$, then cooled to 0° C. Sequentially added anhydrous DMF (44 mg, 0.6 mmol) and oxalyl chloride (523 uL, 6.0 mmol). Allowed to warm to ambient temperature. After 12h, cooled to 0° C. and again sequentially added anhydrous DMF (44 mg, 0.60 mmol) and oxalyl chloride (261 uL, 3.00 mmol). After 4h, checked by $^{13}CNMR$, which confirmed acid chloride (δ171) with small amount of carboxylic acid (δ173). Filtered through silica plug. Filtrate was concentrated in vacuo to afford 900 mg (80%) of trans-2-(chlorocarbonypcyclopropyl)methyl nitrate (n-6) as an oil, which was used without further purification.

$^1H$ NMR (400 MHz, DMSO-$d_6$): δ 4.47-4.67 (m, 1 H), 4.26-4.47 (m, 1 H), 1.52-1.75 (m, 2 H), 0.88-1.13 (m, 2 H).

Step 6

Example N-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl trans-2-[(Nitrooxy)methyl]cyclopropanecarboxylate

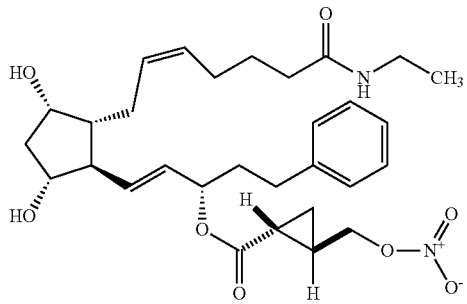

To a solution of bimatoprost boronate b-1 (560 mg, 1.16 mmol) in DCM (6.86 mL) at 0° C. was added DMAP resin (Biotage "PS-DMAP"; 1.125 g of 1.6 mmol/g, 1.80 mmol) and crude acid chloride n-6 (312 mg, 1.74 mmol). After 20 min at 0° C., the cooling bath was removed, and the mixture was allowed to stir at ambient temperature for 12 h. The resultant mixture was cooled to 0° C. and additional acid chloride n-6 (214 mg, 1.2 mmol) and DMAP resin (0.772 g of 1.6 mmol/g, 1.236 mmol, 1.03 eq) were added. After 20 min, allowed to warm and stir at ambient temperature for 12h. Filtered off resin, quenched with water (0.5 mL), and removed solvent under reduced pressure. The residue was partitioned with $CH_2Cl_2$ (50 mL) and water (10 mL). Extracted with $CH_2Cl_2$ (2×50 mL). The combined organic layers were dried with $MgSO_4$, filtered and concentrated in vacuo to an oil, which was purified with silica gel (Biotage; 25S column), eluted with a successive gradient of 25%-100% EtOAc-Hexane, 100% EtOAc, and 5% MeOH—$CH_2Cl_2$. Fractions yielded 404 mg, (60%) of {(1R,2R,3S,5R)-2-[(2Z)-7-(ethylamino)-7-oxohept-2-en-1-yl]-3,5-dihydroxycyclopentyl}-1-(2-phenylethyl)-prop-2-en-1-yl trans-2-[(nitrooxy)methyl]cyclopropanecarboxylate (N-1) as a colorless oil, which was a 1:1 mixture of diastereomers by chiral SFC—HPLC analysis.

$^1H$ NMR (400 MHz, DMSO-$d_6$): δ 7.70 (br. s., 1 H), 7.27 (t, J=7.45 Hz, 2 H), 7.13-7.22 (m, 3 H), 5.37-5.52 (m, 3 H), 5.21-5.34 (m, 1 H), 5.14 (d, J=5.81 Hz, 1 H), 4.47-4.58 (m, 2 H), 4.31-4.45 (m, 2 H), 3.85-3.95 (m, 1 H), 3.63-3.74 (m, 1 H), 2.96-3.09 (m, 2 H), 2.53-2.64 (m, 2 H), 2.04-2.24 (m, 3 H), 1.80-1.97 (m, 6 H), 1.56-1.72 (m, 3 H), 1.38-1.53 (m, 3 H), 1.24-1.37 (m, 1 H), 1.04-1.14 (m, 2 H), 0.92-1.02 (m, 3 H).

LCMS ESI (M+Na)$^+$: 581.2.

HRMS Calcd for $C_{30}H_{42}N_2O_8$ m/z [M+Na]$^+$: 581.2833. Found: 581.2828.

Anal. Calcd for $C_{30}H_{42}N_2O_8$·0.13$H_2O$: C, 64.23; H, 7.59; N, 4.99. Found: C, 64.23; H, 7.57; N, 4.97.

Example O-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 5-(Nitrooxy)pentanoate

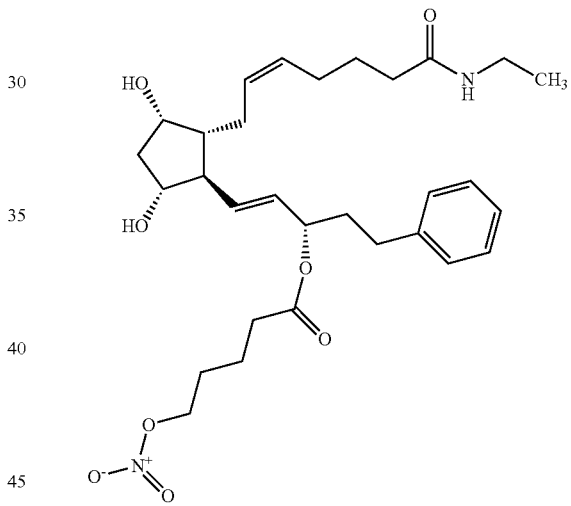

5-(Nitrooxy)pentanoic acid (489 mg, 3.00 mmol; US Patent 2006/189603) was dissolved in anhydrous DCM (30 mL) under $N_2$, cooled to 0° C., and added in succession anhydrous DMF (1 drop) and oxalyl chloride (262 uL, 3.00 mmol). Allowed to stir at ambient temperature for 12 h. $^{13}CNMR$ displayed acid chloride (δ171 ppm) with small amount of carboxylic acid (~δ173 ppm). Evaporated and dried in vacuo to yield 450 mg (80%) of 5-chloro-5-oxopentyl nitrate as light yellow oil, which was used without further purification.

To a solution of bimatoprost boronate b-1 (560 mg, 1.16 mmol) in DCM (2 mL) at 0° C. was added sequentially DMAP resin (1.087 g of 1.6 mmol/g; 1.74 mmol; Biotage "PS-DMAP") and crude 5-chloro-5-oxopentyl nitrate (305 mg, 1.69 mmol). After 20 min at 0° C., the cooling bath was removed, and allowed to stir at ambient temperature. After 24 h, cooled to 0° C. and added more 5-chloro-5-oxopentyl nitrate (125 mg, 0.70 mmol, 0.60 eq) and DMAP resin (0.453 g of 1.6 mmol/1 g, 0.725 mmol, 0.625 eq). Allowed to warm and stir at ambient temperature for 24 h before cooling to 0°

C. and adding additional crude 5-chloro-5-oxopentyl nitrate (209 mg, 1.16 mmol) and DMAP resin (0.743 g of 1.6 mmol/1 g, 1.19 mmol, 1.03 eq). Allowed to warm and stir at ambient temperature 72h. Filtered off resin, quenched with water (0.5 mL), and removed solvent under reduced pressure to give a residue that was partitioned with CH$_2$Cl$_2$ (50 mL) and water (10 mL), extracted with CH$_2$Cl$_2$ (2×50 mL). The combined organic layers were dried with MgSO$_4$, evaporated in vacuo to an oil, which was purified by mass-directed prep-HPLC to yield 233 mg (49.5%) of (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl5-(nitrooxy)pentanoate (0-1) as colorless oil.

$^1$H NMR (400 MHz, DMSO-d$_6$) δ 7.68 (t, J=5.05 Hz, 1 H), 7.22-7.32 (m, 2 H), 7.12-7.21 (m, 3 H), 5.35-5.55 (m, 3 H), 5.11-5.31 (m, 2 H), 4.47-4.61 (m, 3 H), 4.40 (d, J=4.80 Hz, 1 H), 3.85-3.95 (m, 1 H), 3.62-3.76 (m, 1 H), 2.95-3.11 (m, 2 H), 2.53-2.63 (m, 2 H), 2.35 (t, J=7.20 Hz, 2 H), 2.03-2.27 (m, 3 H), 1.81-2.01 (m, 7 H), 1.55-1.72 (m, 4 H), 1.38-1.52 (m, 3 H), 1.26-1.35 (m, 1 H), 0.97 (t, J=7.20 Hz, 3 H).

LCMS ESI (M+Na)$^+$: 584.2

MS: Calcd for C$_{30}$H$_{44}$N$_2$O$_8$Na [M+Na]$^+$: m/z 583.2989. Found: 583.2993.

Anal. Calcd for C$_{30}$H$_{44}$N$_2$O$_8$·0.32H$_2$O·0.06 CH$_2$Cl$_2$: C, 63.10; H, 7.88; N, 5.02. Found: C, 63.17; H, 7.89; N, 4.90.

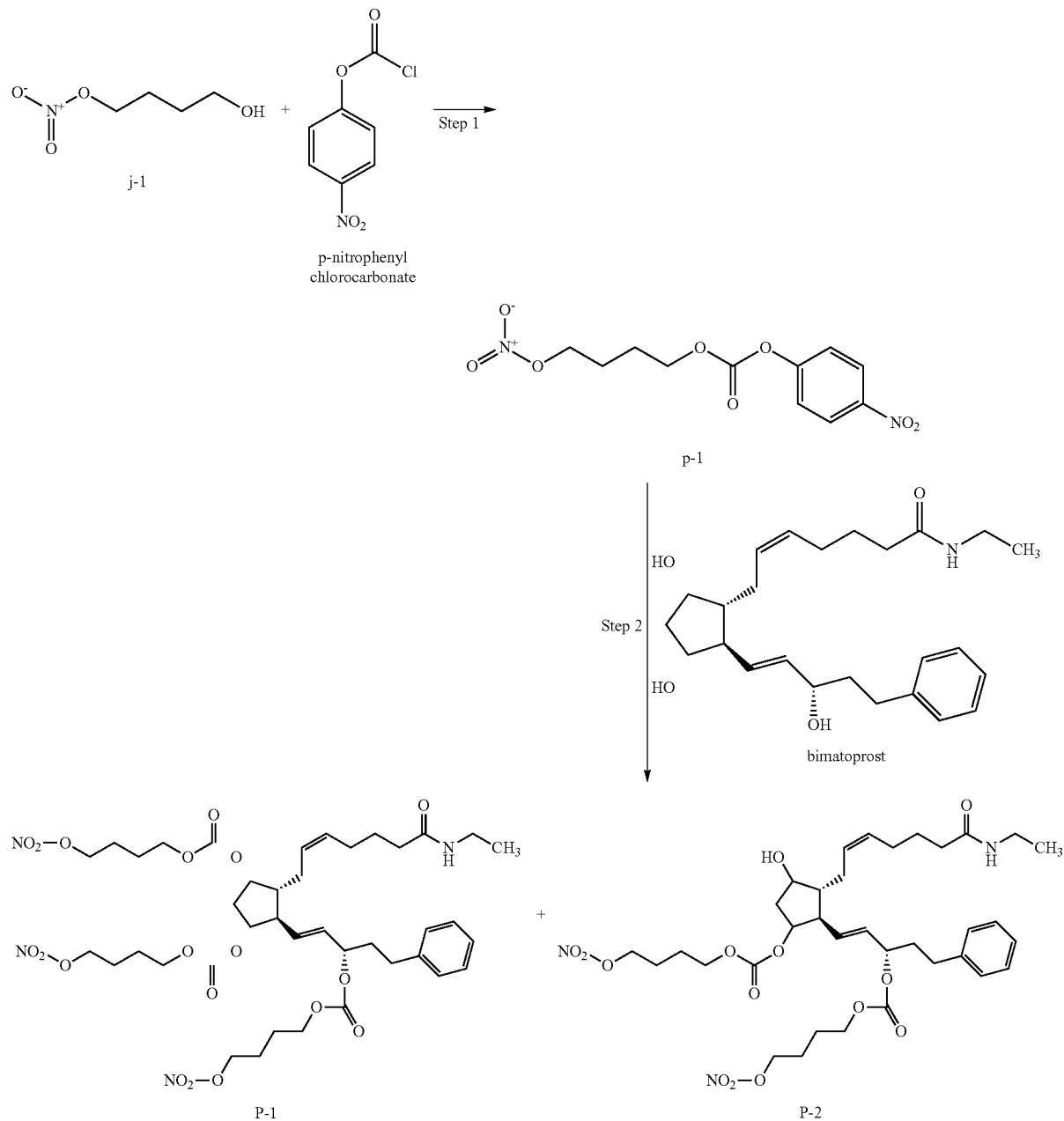

Scheme P

-continued

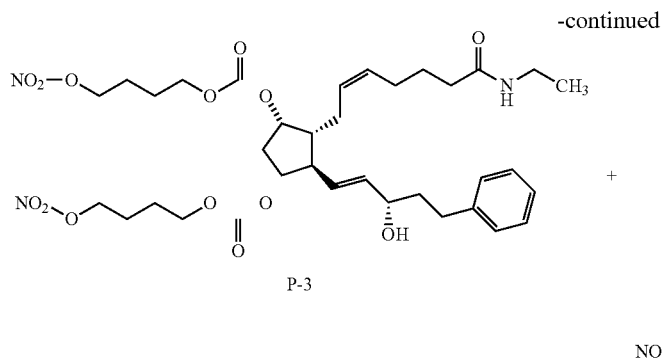

P-3

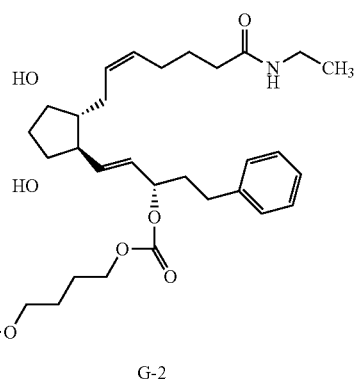

G-2

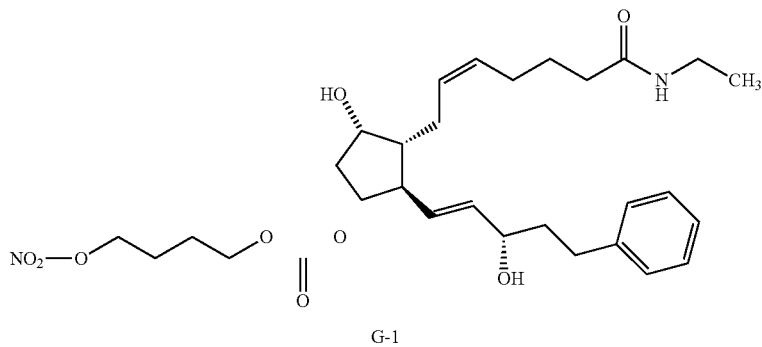

G-1

Step 1.4-(Nitrooxy)butyl 4-Nitrophenyl Carbonate (p-1)

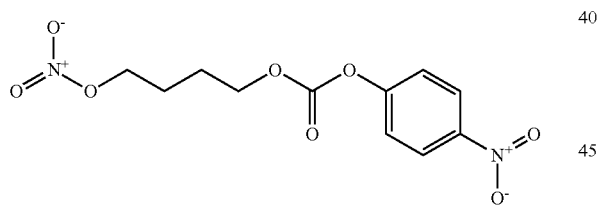

Crude 4-hydroxy-butyl nitrate (j-1; 1580 mg, 11.7 mmol; patent application US2006/189603 A1) was dissolved in ACN and THF (1:3, 112 mL) and treated with p-nitrophenyl chlorocarbonate (4.71 g, 23.4 mmol). Pyridine (2.84 mL, 35.1 mmol) was added slowly and the mix became warm, therefore cooled with an ice-bath during addition. The mix was allowed to stir at ambient temperature overnight. The resultant suspension was filtered. Solids were washed with ACN and THF. The filtrate was concentrated under reduced pressure. The residue was dissolved in EA, washed with water and brine, dried over anhydrous sodium sulfate, filtered, and concentrated to give 1.49 g of a crude solid, which was poorly organic soluble for normal phase chromatography. Purified via preparative HPLC to obtain 1.45 g (41%) of colorless solid, which was used without further purification.

$^1$H NMR (400 MHz, CDCl$_3$) δ 1.91 (dt, J=6.06, 3.03 Hz, 4 H), 4.23-4.45 (m, 2 H), 4.47-4.68 (m, 2 H), 7.32-7.48 (m, 2 H), 8.16-8.50 (m, 2 H).

Step 2. Acylation of Bimatoprost with 4-(Nitrooxy)butyl 4-Nitrophenyl Carbonate (1R,3S,4R,5R)-4-[(2Z)-7-(Ethylamino)-7-oxohept-2-en-1-yl]-5-[(1E,3S)-3-({[4-(nitrooxy)butoxy]carbonyl}oxy)-5-phenylpent-1-en-1-yl]cyclopentane-1,3-diyl bis[4-(Nitrooxy)butyl]Biscarbonate (P-1)

(1S,2E)-3-[(1R,2R,3S,5R)-2-[(2Z)-7-(ethylamino)-7-oxohept-2-en-1-yl]-3-hydroxy-5-({[4-(nitrooxy)butoxy]carbonyl}oxy)cyclopentyl]-1-(2-phenylethyl)prop-2-en-1-yl 4-(nitrooxy)butyl carbonate (P-2)(1R,3S,4R,5R)-4-[(2Z)-7-(ethylamino)-7-oxohept-2-en-1-yl]-5-[(1E,3S)-3-hydroxy-5-phenylpent-1-en-1-yl]cyclopentane-1,3-diyl bis[4-(nitrooxy)butyl] biscarbonate (P-3)

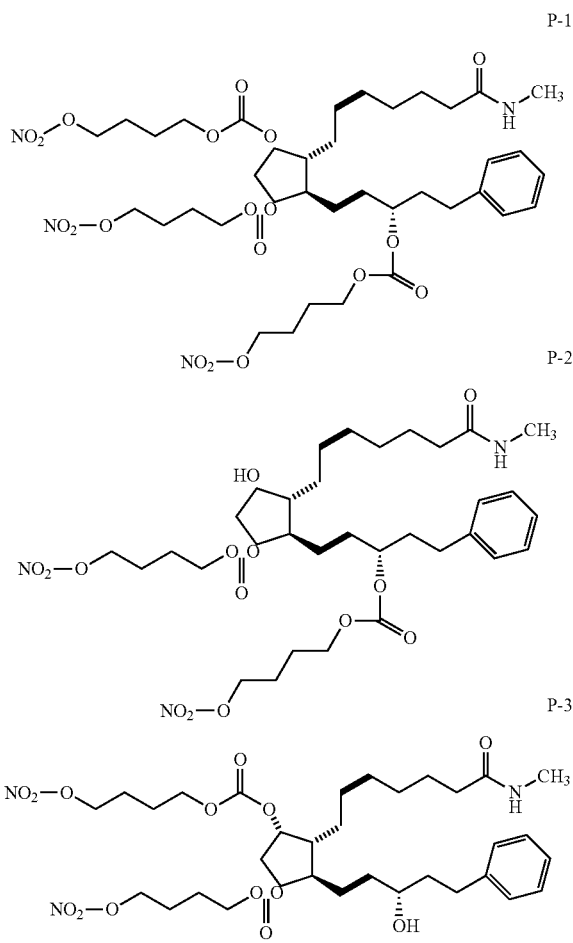

Bimatoprost (1.00 g, 2.41 mmol) was dissolved in DCM (24.1 mL), treated with 4-(nitrooxy)butyl 4-nitrophenyl carbonate (p-1; 1.45 g, 4.82 mmol) and DMAP (607 mg, 4.82 mmol), and allowed to stir at ambient temperature for 60 h. The resultant mixture was diluted with DCM, washed with water and brine, dried over anhydrous sodium sulfate, filtered, and concentrated to a crude mixture, which was purified via successive cycles of chromatography: MPLC (10-100% EA/hexane, followed with 5-15% methanol in DCM), then preparative HPLC to afford several pure compounds as follows:

11-Carbonate G-1: 210 mg (15%) pale yellow oil
15-Carbonate G-2: 30 mg (2%) pale yellow oil.

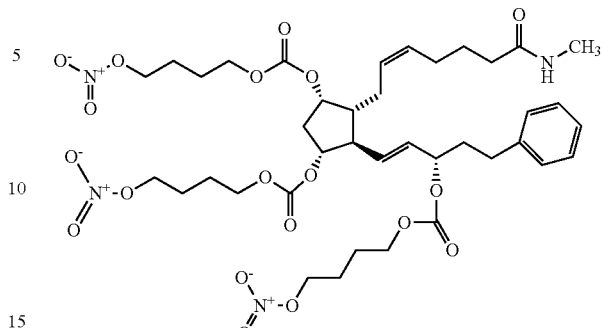

tri-Nitrate P-1: 124 mg (5%) pale yellow oil.
$^1$H NMR (400 MHz, DMSO-$d_6$) δ 0.98 (t, J=7.20 Hz, 3 H), 1.41-1.55 (m, 2 H), 1.59-1.78 (m, 13 H), 1.80-2.15 (m, 9 H), 2.43-2.50 (m, 1 H), 2.54-2.65 (m, 3 H), 2.96-3.10 (m, 2 H), 3.99-4.18 (m, 6 H), 4.33-4.33 (m, 0 H), 4.45-4.62 (m, 6 H), 4.81 (ddd, J=8.91, 7.26, 3.79 Hz, 1 H), 4.87 (t, J=4.67 Hz, 1 H), 4.93-5.04 (m, 1 H), 5.25-5.41 (m, 2 H), 5.59-5.72 (m, 2 H), 7.13-7.23 (m, 3 H), 7.23-7.34 (m, 2 H), 7.69 (t, J=5.18 Hz, 1 H).
Anal. Calcd for $C_{40}H_{58}N_4O_{19}$·0.25$H_2O$: C, 62.00; H, 7.72; N, 4.82. Found C, 62.06; H, 7.76; N, 4.90.

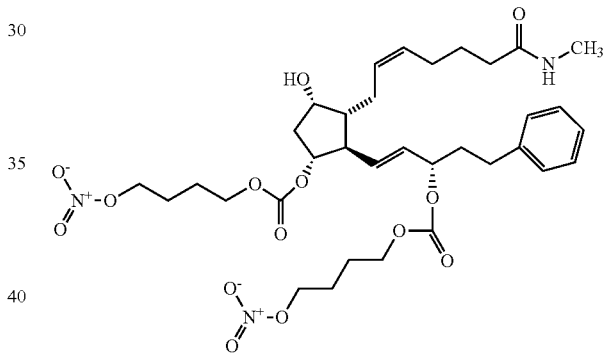

11,15-di-Nitrate P-2: 320 mg (18%) pale yellow oil.
$^1$H NMR (400 MHz, DMSO-$d_6$): δ 0.97 (t, J=7.20 Hz, 3 H), 1.38-1.58 (m, 4 H), 1.58-1.77 (m, 8 H), 1.79-2.03 (m, 7 H), 2.05-2.17 (m, 1 H), 2.34 (ddd, J=14.78, 9.09, 5.43 Hz, 1 H), 2.44-2.48 (m, 1 H), 2.52-2.63 (m, 2 H), 2.96-3.07 (m, 2 H), 3.95 (d, J=4.04 Hz, 1 H), 3.98-4.15 (m, 4 H), 4.51 (ddd, J=12.88, 6.32, 6.06 Hz, 4 H), 4.64-4.76 (m, 2 H), 4.96 (q, J=6.48 Hz, 1 H), 5.28 (dt, J=10.93, 7.17 Hz, 1 H), 5.34-5.46 (m, 1 H), 5.48-5.69 (m, 2 H), 7.11-7.21 (m, 3 H), 7.22-7.32 (m, 2 H), 7.69 (t, J=5.31 Hz, 1 H).
LCMS (M+Na$^+$): m/z 760.2.

The critical aspect of confirming this structure was assignment of methine signals (H-8,H-9,H-11, H-12,H-15-see non-conventional numbering and structure below) and hydroxyl signals through inspection of 1D proton, 2D HSQC,COSY and HMBC spectra. The hydroxyl group at C-9 was identified through inspection of HSQC spectrum, looking for signals in the proton spectrum with an absence of a cross peak in the HSQC. The hydroxyl group was located relative to methine H-8 and methylene H-5 through inspection of COSY spectrum. Clear and distinct coupling from H-15 to H-10a and H-12 to H-9a also observed in COSY spectrum. HMBC spectrum allowed for the assignment of methine protons H-9 and H-15 relative to distinct carbonyls C-7 and C-13a, as shown in the picture below.

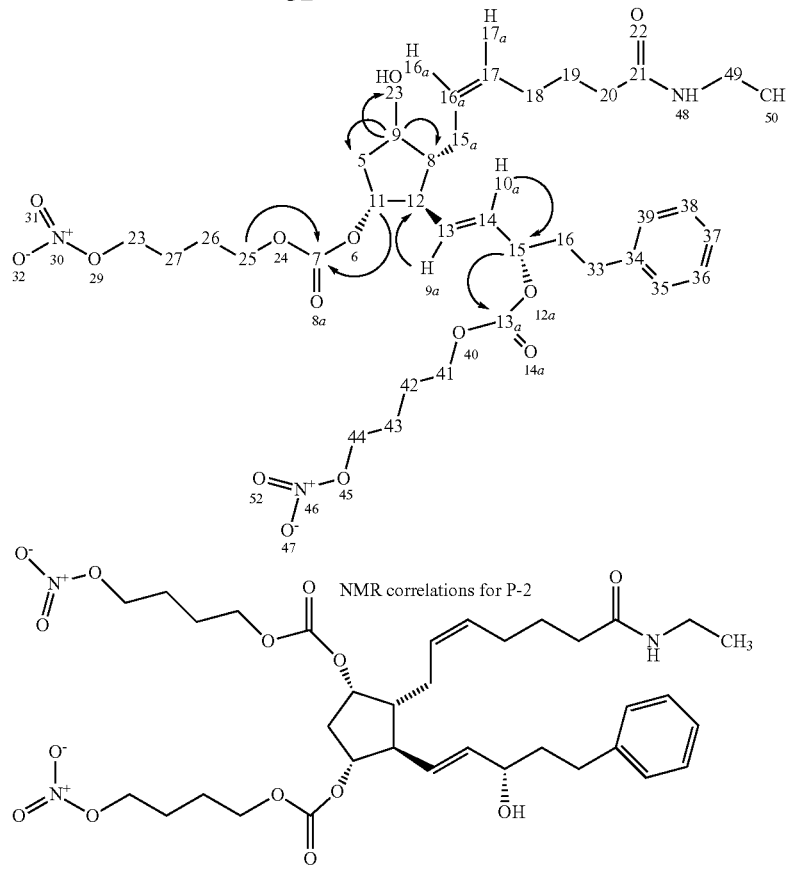

NMR correlations for P-2

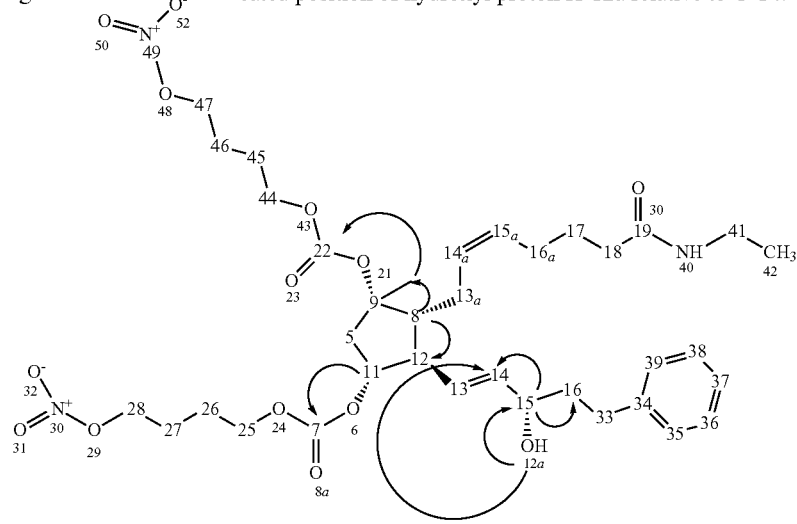

P-3

9,11-di-Nitrate P-3: 78 mg (4%) pale yellow oil.

$^1$H NMR (400 MHz, DMSO-$d_6$): δ 0.97 (t, J=7.20 Hz, 3 H), 1.41-1.51 (m, 2 H), 1.58-1.76 (m, 11 H), 1.76-2.12 (m, 7 H), 2.38-2.48 (m, 1 H), 2.52-2.65 (m, 3 H), 2.96-3.08 (m, 2 H), 3.88-3.98 (m, 1 H), 4.00-4.15 (m, 4 H), 4.52 (dt, J=17.62, 6.09 Hz, 4 H), 4.73-4.83 (m, 2 H), 4.86 (t, J=4.93 Hz, 1 H), 5.25-5.39 (m, 2 H), 5.43-5.63 (m, 2 H), 7.10-7.20 (m, 3 H), 7.21-7.30 (m, 2 H), 7.69 (s, 1 H).

LCMS (M+Na$^+$): m/z 760.2.

The critical aspect that confirmed this structure by NMR was assignment of the methine signals (H-8, H-9, H-11, H-12, H-15—see non-conventional numbering and structure below) and hydroxyl signals through inspection of 1D proton, 2D HSQC, COSY, and HMBC spectra. The hydroxyl group at C-15 was identified through inspection of HSQC spectrum, looking for signals in the proton spectrum with an absence of a cross peak in the HSQC. This hydroxyl group was located relative to methines H-14 and H-16 through inspection of COSY spectrum showing clear and distinct coupling from H-15 to H-14. COSY spectrum also indicated relative position of H-8 to H-9 and H-12. HMBC spectrum allowed for the assignment of methine protons H-9 and H-11 relative to distinct carbonyls C-7 and C-22. HMBC correlations also indicated position of hydroxyl proton H-12a relative to C-14.

NMR Correlations for P-3

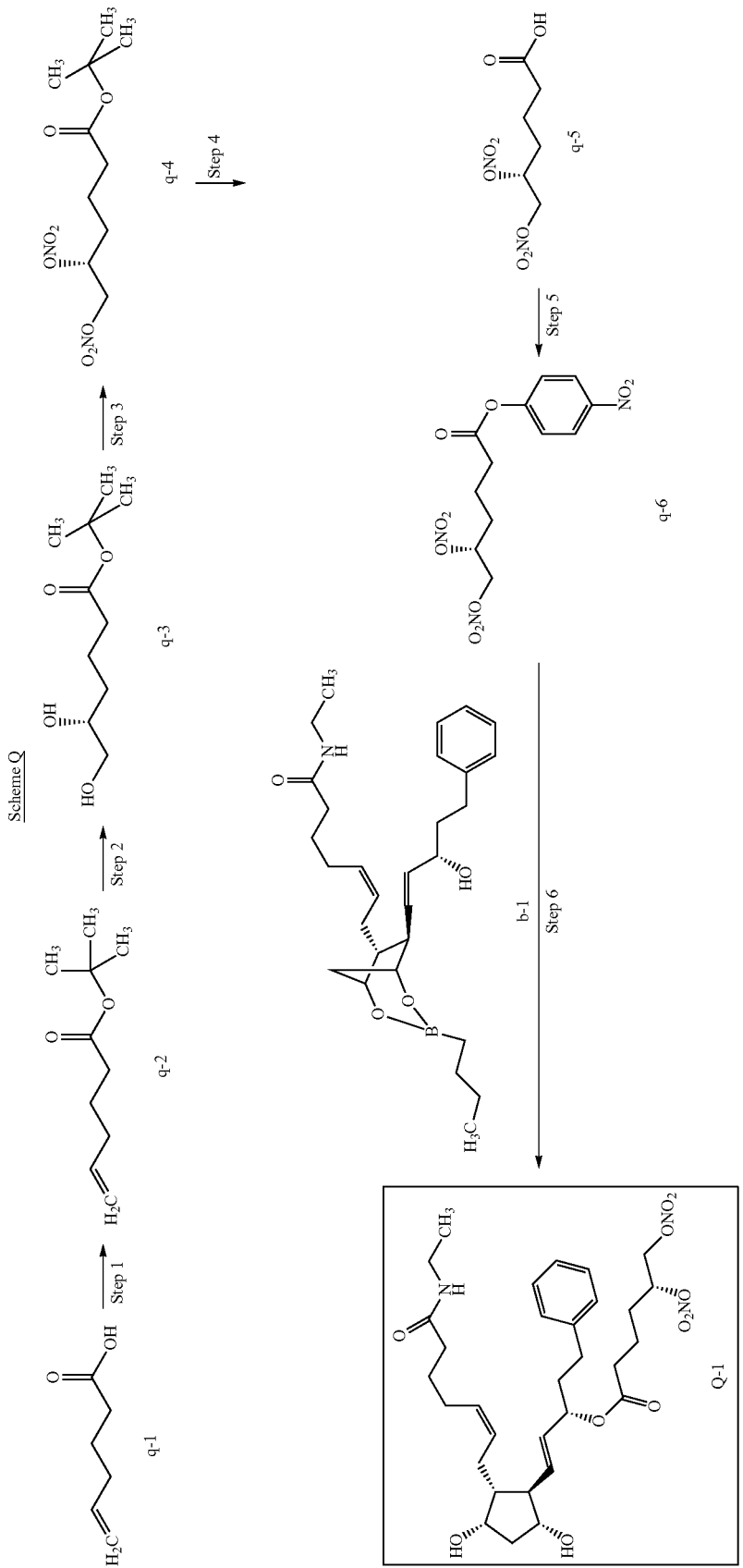

Example Q-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5R)-5,6-bis(Nitrooxy)hexanoate

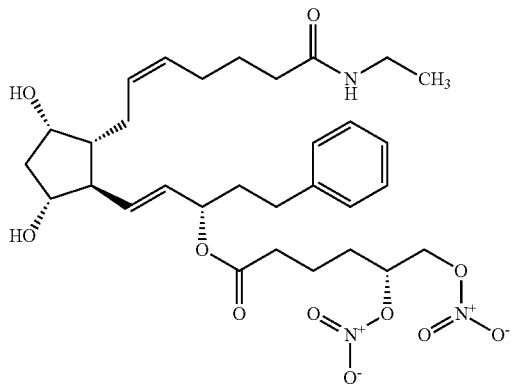

Step 1: tert-Butyl Hex-5-enoate (q-2)

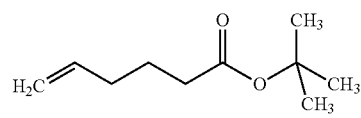

To a stirred solution of 5-hexenoic acid q-1 (6.00 g, 52.6 mmol), t-butyl alcohol (72.2 mL, 735.84 mmol) and DMAP (1.28 g, 10.51 mmol) in DCM (150 mL) at −10° C. was added DCC (16.26 g, 78.84 mmol). After stirring at room temperature overnight, solid was filtered off. The filtrate was evaporated under reduced pressure to give a crude oil, which was purified by chromatography (Biotage; 65i). Elution with a gradient of EtOAc/Hexane from 5/95 to 10/90 yielded 4.16 g (46.53%) of t-butyl ester q-2, which displayed a $^1$H NMR spectrum that matched literature (Johnson, P. Y.; Berchtold, G. A. J. Org. Chem. 1970, 35, 584-592) and was used without further purification).

Step 2: tert-Butyl (5R)-5,6-Dihydroxyhexanoate (q-3)

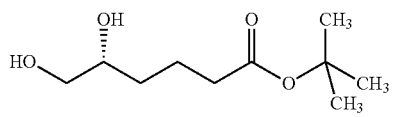

To a stirring suspension of AD-mix-β (Sigma-Aldrich, 40 g, 1.4 g/mol) in H$_2$O/t-butyl alcohol 1:1 (300 mL) at 0° C., olefin q-2 (4.95 g, 28 mmol) was added. The mixture stirred overnight at 4° C., then EtOAc (160 mL) was added keeping the temperature at 0° C. using an ice bath and Na$_2$S$_2$O$_5$ (11.8 g) was added. After 30 min the ice bath was removed and the temperature allowed to rise to 23° C. The aqueous phase was extracted with EtOAc (3×200 mL). The organic phase was washed with brine, dried over Na$_2$SO$_4$, filtered over silica gel, and the solvent evaporated under reduced pressure to give 5.43 g (95%) of chiral diol q-3, which was used without further purification.

Step 3: tert-Butyl (5R)-5,6-bis(Nitrooxy)hexanoate (q-4)

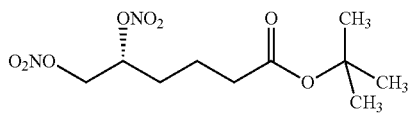

To a solution of HNO$_3$ (5.8 mL, 140 mmol) in Ac$_2$O (20 mL) cooled at 0° C., was added a solution of diol q-3 (5.72 g, 28 mmol) in DCM (20 mL). The mixture was cooled to 0° C. After 30 min, NaOH was added to reach pH 7 and the mixture extracted with DCM (3×50 mL) The organic phase was dried over sodium sulfate and the compound purified by chromatography (Biotage; 100 SNAP), eluting with a gradient of EtOAc-Hexane from 5/95 to 20/80, giving 5 g (61%) of chiral dinitrate q-4, which was used without further purification.

Step 4: (5R)-5,6-bis(Nitrooxy)hexanoic Acid (q-5)

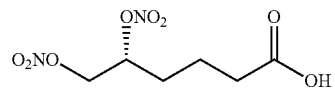

To a solution of t-butyl ester q-4 (5 g, 17 mmol) in DCM (20 mL) cooled at 0° C., was added BF$_3$.Et$_2$O (2.4 mL, 18.7 mmol) and the mixture stirred at 0° C. for 3 h and at room temperature overnight. A sat aq NaHCO$_3$ and NaOH (pellets) were added till pH 10 and the mixture extracted with DCM (3×150 mL). The organic phase was slowly acidified with HCl 3M, extracted with DCM, washed with brine, and dried over Na$_2$SO$_4$. The solvent was partially removed to approximately 20 mL under reduced pressure at ambient temperature and the solution of acid q-5 in DCM used for following reactions (4.05 g theoretical final amount). The $^1$H NMR matched that reported for racemate in Lazzarato, L.; et al. J. Med. Chem. 2005, 48, 1322-1329.

Step 5: 4-Nitrophenyl (5R)-5,6-bis(Nitrooxy)hexanoate (q-6)

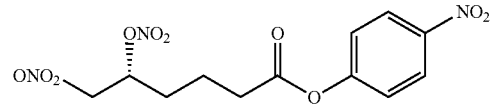

To a solution of acid q-5 (1.33 g, 5.6 mmol) in DCM (20 mL) were added EDAC (1.3 g, 6.7 mmol), DMAP (cat. amount) and p-nitrophenol (780 mg, 5.6 mmol). The mixture was allowed to stir overnight and then a saturated solution of NaHCO$_3$ was added. The solvent was evaporated under reduced pressure and crude purified by chromatography (Biotage; 100 SNAP), eluting with a mixture of DCM/Hexane 80/20, to yield 1.25 g (63%) of p-nitrophenyl ester q-6, which was used without further purification.

Step 6: (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5R)-5,6-bis(Nitrooxy)hexanoate

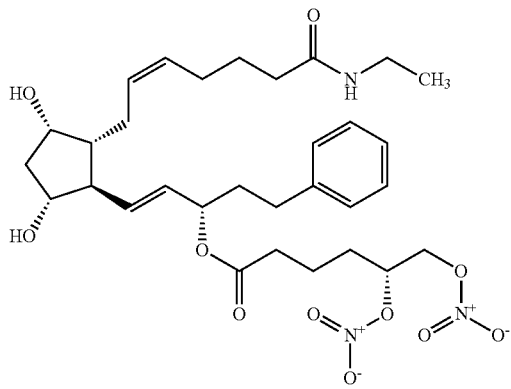

The boronate of bimatoprost b-1 was acylated with crude p-nitrophenyl ester q-6 (1.25 g, 3.48 mmol) and DMAP (430 mg, 3.48 mmol) in DCM (20 mL). The mixture stirred for 8 h and DCM evaporated under reduced pressure. The residue was dissolved in MeOH (20 mL) and stirred overnight to deprotect the compound. The solvent was evaporated and preparative HPLC provided pure 340 mg (55%) of 15-acyl dinitrate Q-1.

$^1$H NMR (300 MHz, DMSO-$d_6$): δ 0.97 (t, 3 H), 1.35 (m, 1 H), 1.40-1.65 (m, 3 H), 1.60-1.80 (m, 4 H), 1.80-2.00 (m, 7 H), 2.05-2.25 (3 H), 2.34-2.38 (m, 2 H), 2.57-2.62 (m, 2 H), 3.01-3.05 (m, 2 H), 3.60-3.71 (m, 1 H), 3.91 (m, 1 H), 4.40 (d, 1 OH), 4.57 (d, 1 OH), 4.67-4.96 (m, 2 H), 5.17 (m, 1 H), 5.28 (m, 1 H), 5.41-5.50 (m, 4 H), 7.16-7.19 (m, 3 H), 7.25-7.30 (m, 2 H), 7.69 (s, 1 H).

MS (M+1): 636.2

Example Q-2:

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5,6-bis(Nitrooxy)hexanoate

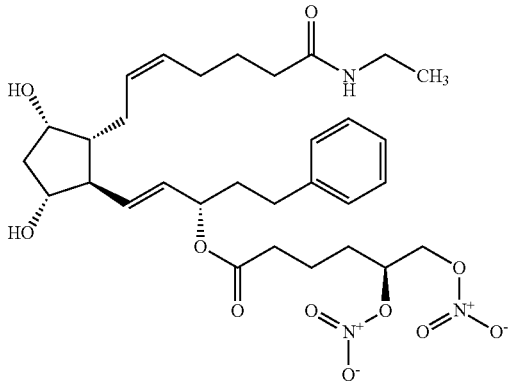

In a manner similar to that for antipode Q-1, AD-mix-alpha was used in Scheme Q to generate the enantiomer of nitrophenyl ester q-6. Thus accordingly Q-2 was prepared and purified via preparative HPLC. As expected, NMR spectra were identical to that for Q-1.

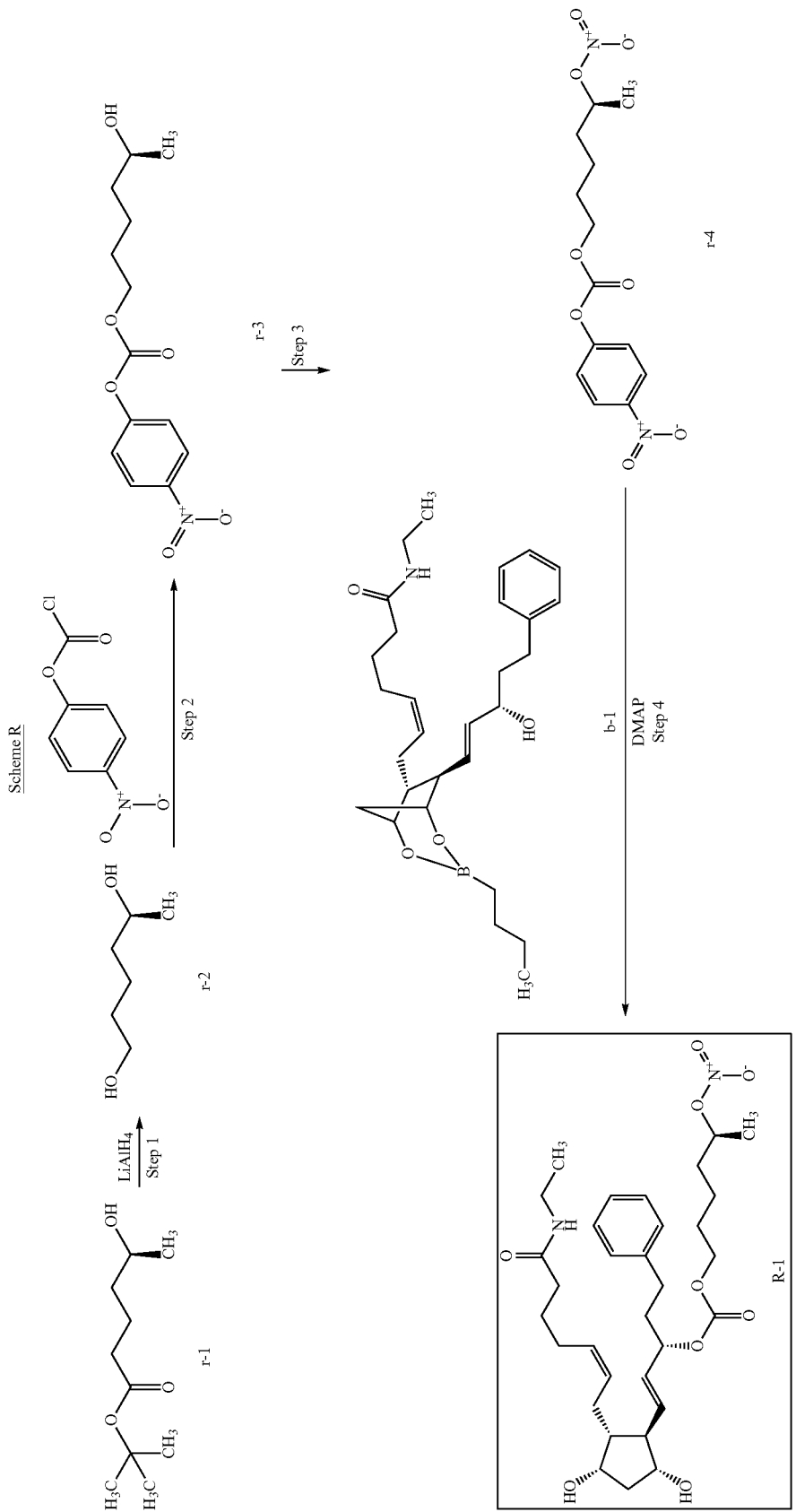

Example R-1

(1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy)hexyl carbonate

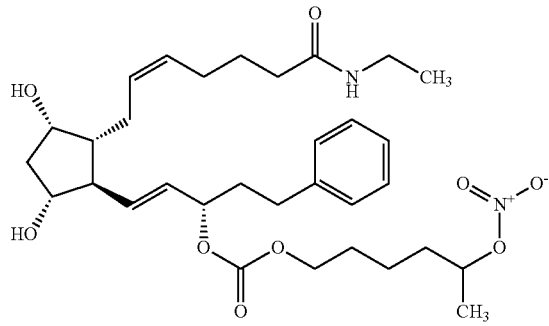

Step 1: (5S)-Hexane-1,5-diol (r-2)

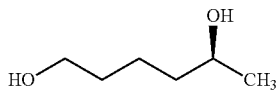

To a stirring solution of tert-butyl (5S)-5-hydroxyhexanoate (r-1; Pamies, O.; Backvall, J.-E. *J. Org. Chem.* 2002, 67, 1261-1265; 3.00 g, 15.9 mmol) in THF (35 mL) at 0° C., was added LiAlH$_4$ (31.88 mL of 1M in THF, 31.88 mmol). The mixture stirred for 4 h, cooled to 0° C., and treated with of NaOH 1N until effervescence stopped. Et$_2$O (600 mL) was added and the mixture was kept under strong stirring. The solution was dried over Na$_2$SO$_4$, filtered and the solvent evaporated under reduced pressure to obtain 1.9 g of chiral diol r-2, which had an NMR identical to reported (Davies, S. G.; Smyth, G. D. *Tetrahedron: Asymmetry* 1996, 7, 1001-1004) and was used without further purification.

Step 2: (5S)-5-Hydroxyhexyl 4-nitrophenyl Carbonate (r-3)

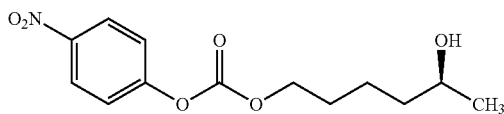

To a solution of diol r-2 (1.75 g, 14.81 mmol) in DCM (36 mL), pyridine (1.31 mL, 16.3 mmol) was added and the mixture was cooled at 0° C. A solution of p-nitrophenyl chloroformate (2.98 g, 14.81 mmol) in DCM (8 mL) was added dropwise and after 3 h the mixture was washed with 5% aq H$_3$PO$_4$ (100 mL). The solution was dried and the solvent was evaporated under reduced pressure to give the crude compound (5 g) that was purified with silica gel (Biotage; 40+M), eluted with a successive gradient of 20%-50% EtOAc-Hexane, 50% EtOAc and giving 2.44 g (58%) of mixed carbonate r-3, which was used without further purification.

Step 3: (5S)-5-Nitroxyhexyl 4-nitrophenyl Carbonate (r-4)

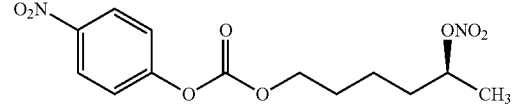

To a solution of HNO$_3$ (2.02 mL, 48.73 mmol) in Ac$_2$O (13 mL) cooled at 0° C., r-3 (2.3 g, 8.12 mmol) solved in DCM (2 mL) was added and the mixture was cooled at 0° C. After 30 minutes NaOH was added to reach pH 7 and the mixture extracted with DCM (3×150 m). The organic phase was dried and the compound purified with silica gel (Biotage; 40+M), eluted with a successive gradient of 5%-20% EtOAc-Hexane, 20% EtOAc giving 1.97 g (74%) of nitrate r-4, which was used without further purification.

Step 4: (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy)hexyl carbonate (R-1)

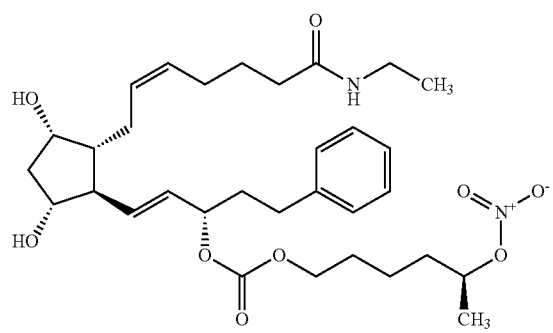

The boronate of bimatoprost b-1 (580 mg, 1.2 mmol) was acylated with crude p-nitrophenyl ester r-4 (1.18 g, 3.61 mmol) and DMAP (441 mg, 3.61 mmol) in DCM (25 mL). The mixture stirred for 8 h and solvent evaporated under reduced pressure. The residue was dissolved in MeOH (20 mL) and stirred overnight to deprotect the compound. The solvent was evaporated and preparative HPLC provided pure 380 mg (52%) of R-1.

$^1$H NMR (300 MHz, DMSO-d$_6$): δ 0.97 (t, 3 H), 1.30 (d, 3 H), 1.30-1.70 (m, 10 H), 1.80-2.00 (m, 7 H), 2.05-2.25 (3 H), 2.60 (m, 2 H), 3.02 (m, 2 H), 3.68 (m, 1 H), 3.90 (m, 1 H), 4.05 (m, 2 H), 4.40 (d, 1 OH), 4.60 (d, 1 OH), 4.96 (m, 1 H), 5.12 (m, 1 H), 5.28 (m, 1 H), 5.37-5.62 (m, 3 H), 7.16-7.19 (m, 3 H), 7.25-7.30 (m, 2 H), 7.69 (s, 1 H)

MS (M+1): 605. .

Example R-2

(1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5R)-5-(nitrooxy) hexyl carbonate

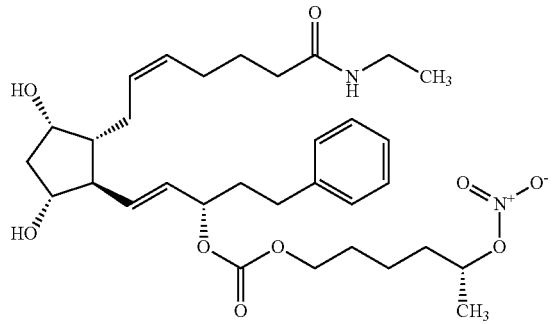

Similar to Example R-1, except started Scheme R with antipodal tert-butyl (5R)-5-(acetoxy)hexanoate (Pamies, O.; Backvall, J.-E. *J. Org. Chem.* 2002, 67, 1261-1265) and eventually prepared antipode of crude p-nitrophenyl carbonate r-4, which was similarly used to acylate bimatoprost boronate (580 mg, 1.2 mmol) to provide after preparative HPLC purification, 420 mg (57%) of 15-acyl nitrate R-2.

$^1$H NMR (300 MHz, DMSO-$d_6$): δ 0.97 (t, 3 H), 1.30 (d, 3 H), 1.30-1.70 (m, 10 H), 1.80-2.00 (m, 7 H), 2.05-2.25 (3 H), 2.60 (m, 2 H), 3.02 (m, 2 H), 3.68 (m, 1 H), 3.90 (m, 1 H), 4.05 (m, 2 H), 4.40 (d, 1 OH), 4.60 (d, 1 OH), 4.96 (m, 1 H), 5.12 (m, 1 H), 5.28 (m, 1 H), 5.37-5.62 (m, 3 H), 7.16-7.19 (m, 3 H), 7.25-7.30 (m, 2 H), 7.69 (s, 1 H).

MS (M+1): 605.

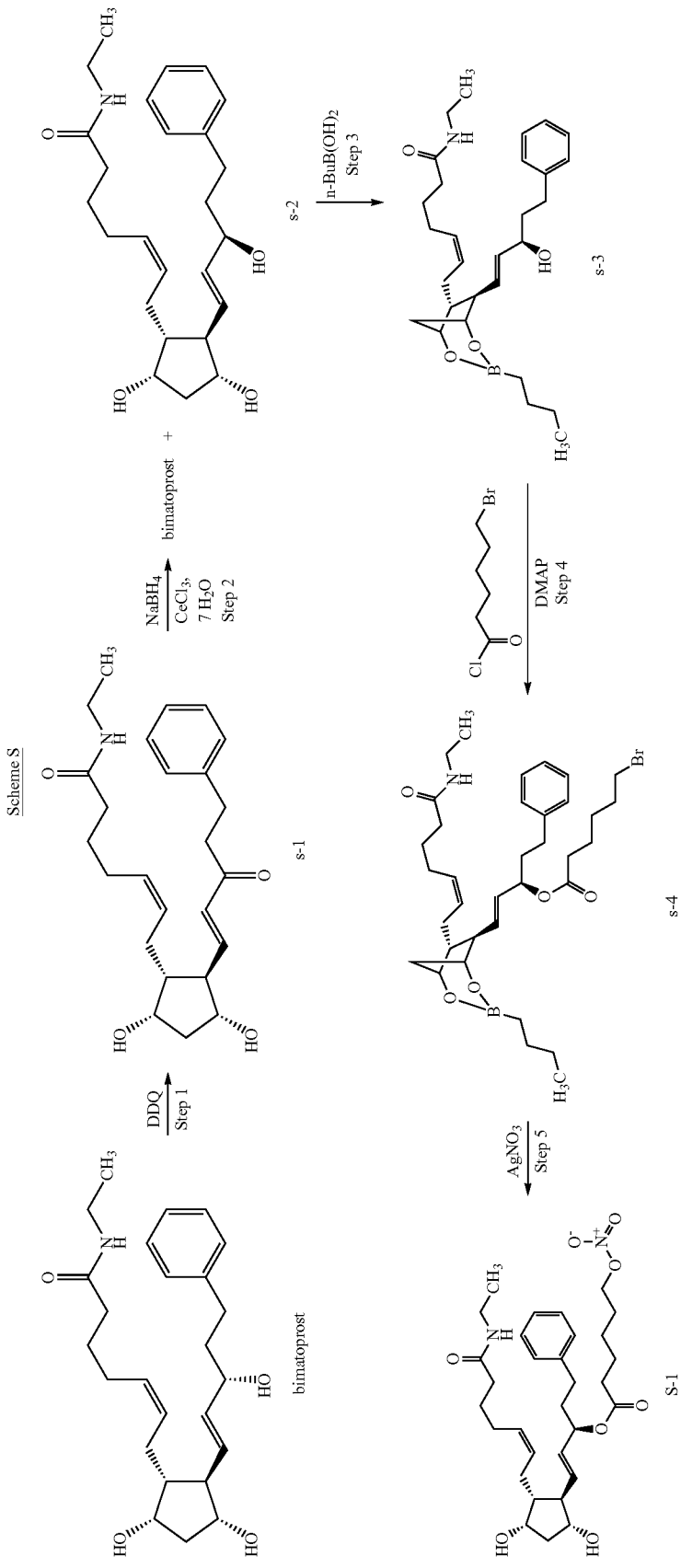

Example S-1

(1R,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 6-(Nitrooxy)hexanoate

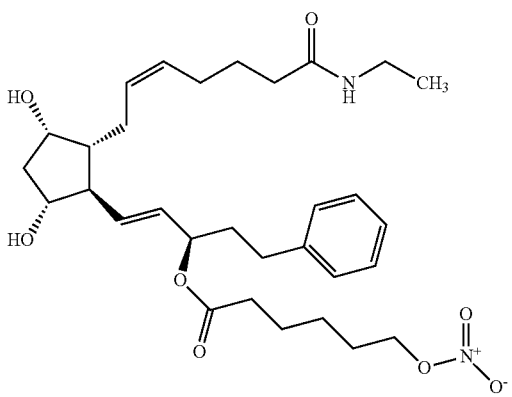

Step 1. (5Z)-7-{(1R,2R,3R,5S)-3,5-Dihydroxy-2-[(1E)-3-oxo-5-phenylpent-1-en-1-yl]cyclopentyl}-N-ethylhept-5-enamide (15-keto-Bimatoprost; s-1)

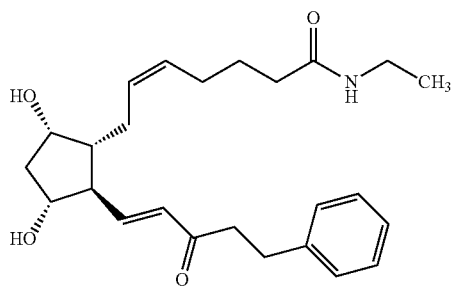

Using a method from Taber, D. F.; Kanai, K. *Tetrahedron* 1998, 54, 11767-11782, to a stirred solution of bimatoprost (100 mg, 0.240 mmol) in 1,4-dioxane (20 mL) was added portionwise DDQ (224 mg, 0.96 mmol). The resultant mixture was stirred at ambient temperature over night and then was washed with water (2×20 mL) and brine (2×20 mL). The organic layer was dried with $Na_2SO_4$, filtered and concentrated in vacuo leading to 15-keto-bimatoprost s-1 (54 mg, 0.13 mmol) in 50% yield as a reddish solid, which was used in the next step without further purification.

$^1$H NMR (300 MHz, CDCl$_3$): δ.1.14 (t, J=7.3 Hz, 3H), 1.35 (d, J=10.5 Hz, 1H), 2.80-2.98 (m, 4H), 3.20-3.35 (m, 2H), 4.05 (bm, 1H), 4.10 (m, 1H), 5.36-5.42 (m, 2H), 6.16 (d, J=15.7 Hz, 1H), 6.68 (dd, J=8.8, 15.7 Hz, 1H).

LCMS ESI (M+Na$^+$): m/z 437.20.

Step 2. (5Z)-7-{(1R,2R,3R,5S)-3,5-Dihydroxy-2-[(1E,3R)-3-hydroxy-5-phenylpent-1-en-1-yl]cyclopentyl}-N-ethylhept-5-enamide (15-epi-Bimatoprost; s-2)

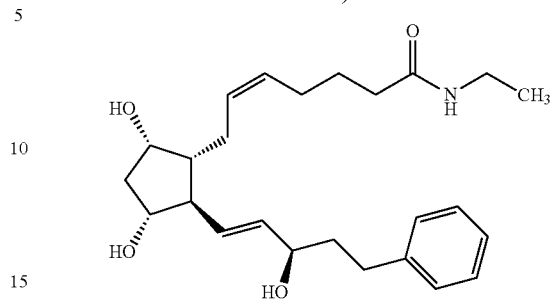

A solution of 15-ketone s-1 (530 mg, max 1.28 mmol) and CeCl$_3$.7H$_2$O (143.3 mg, 0.38 mmol, 0.3 eq.) in MeOH/DCM (2:1, 48 mL) was stirred at −78° C. for 30 minutes under N$_2$ atmosphere. NaBH$_4$ (28.75 mg, 0.77 mmol, 1.6 eq.) was added in one portion. After 1 h at −78° C., the mixture was acidified with aq 1N HCl to pH 3 and diluted with EtOAc (100 mL). Brine (50 mL) was added and the organic layer was separated and washed with brine (2×50 mL) and concentrated in vacuo to lead to 420 mg yellow oil, which was initially purified via MPLC with ISCO apparatus (silica 80 g, DCM/IPA, gradient up to 30%) to first elute 95 mg (18%) of 15-epi-bimatoprost s-2 with a d.e. of 91% by chiral analytical HPLC (Chiralcel OD-H with heptane/EtOH/Et$_2$NH 85/15/0.2). Regenerated bimatoprost (280 mg (53%), with a d.e. of 92%) eluted second, was reused in another cycle as above, combined with other batches, and purified to obtain a d.e. of 97% prior to use below.

$^1$H NMR (300 MHz, CDCl$_3$): δ 1.08 (t, J=6.8 Hz, 3H), 3.18-3.29 (m, 2H), 3.93 (bm, 1H), 4.09 (m, 1H), 4.15 (m, 1H), 5.28-5.63 (m, 4H).

Step 3. (5Z)-7-{(6R,7R)-3-Butyl-7-[(1E,3R)-3-hydroxy-5-phenylpent-1-en-1-yl]-2,4-dioxa-3-borabicyclo[3.2.1]oct-6-yl}-N-ethylhept-5-enamide (s-3)

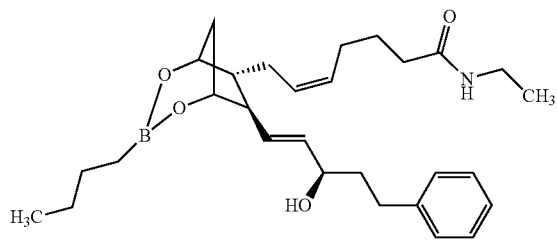

Prepared according to the procedure given for boronate b-1: From 15-epi-bimatoprost s-2 (165 mg, 0.400 mmol) was obtained an oil that was used without further purification.

$^1$H NMR (300 MHz, DMSO-d$_6$): δ.0.82 (t, J=7.3 Hz, 3H), 0.98 (t, J=7.3 Hz, 3H), 3.03 (ddd, J=7.2, 7.3, 12.9 Hz, 2H), 3.88 (m, 1H), 4.03 (s, 1H), 4.78 (d, J=4.7 Hz, 1H), 5.27-5.58 (m, 4H), 7.18-7.37 (m, 5H), 7.73 (bs, 1H).

Step 4. (1R,2E)-3-{(6R,7R)-3-Butyl-7-[(2Z)-7-(ethylamino)-7-oxohept-2-en-1-yl]-2,4-dioxa-3-borabicyclo[3.2.1]oct-6-yl}-1-(2-phenylethyl)prop-2-en-1-yl 6-Bromohexanoate (s-4)

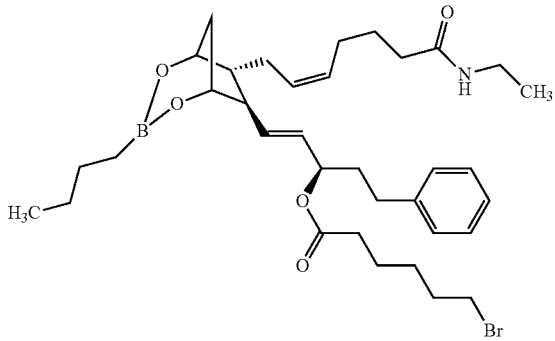

Prepared according to the procedure described for ester b-2: crude alcohol s-3 (theoretical 0.400 mmol) furnished crude halo-ester s-4 as a light yellow oil, which was used in the next step without further purification.

$^1$H NMR (300 MHz, CDCl$_3$): δ 0.88 (t, J=6.9 Hz, 3H), 1.15 (t, J=7.2 Hz, 3H), 2.51 (t, J=7.3 Hz, 1H), 2.62 (t, J=7.2 Hz, 2H), 4.10 (s, 1H), 4.18 (s, 1H), 5.20 (q, J=6.4 Hz, 1H), 5.33-5.58 (m, 4H).

LCESIMS (M+Na): 615.10; 616.10.

Step 5. (1R,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 6-(Nitrooxy)hexanoate S-1)

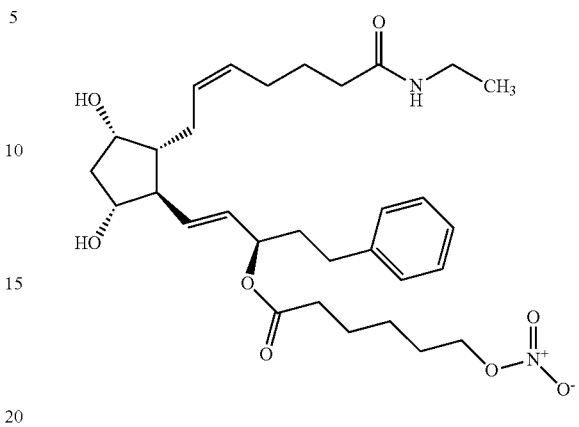

Prepared according to the procedure provided for Example B-1: crude halo-ester s-4 (theoretical 0.400 mmol) afforded 350 mg of a yellow oil, which was purified via MPLC with ISCO apparatus (silica, DCM/IPA, gradient 0-30%) then preparative HPLC (water:acetonitrile:HCOOH) to provide 80 mg (35% yield over three steps) of target nitrate B-1 with a purity of 100% by HPLC-MS.

$^1$H NMR (300 MHz, CDCl$_3$): δ 1.15 (t, J=7.3 Hz, 3H), 2.66 (t, J=7.5 Hz, 1H), 3.30 (ddd, J=1.0, 7.3, 13.0 Hz, 2H), 3.97 (bs, 1H), 4.20 (bs, 1H), 4.46 (t, J=6.6 Hz, 2H), 5.28 (dd, J=6.6, 13.2 Hz, 1H), 5.39 (m, 1H).

LC ESI MS (M+Na$^+$): m/z 597.30.

TABLE 1

Specific Examples

| Example number | Structure | Chemical Name | ¹HNMR | MS |
|---|---|---|---|---|
| A-1 | 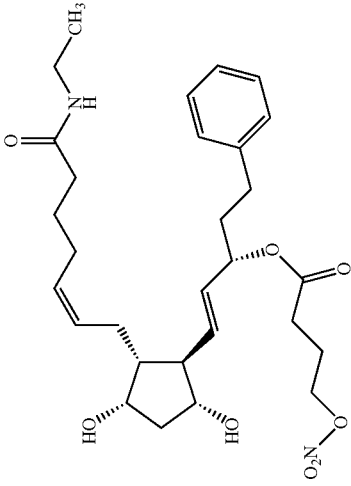 | (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 4-(Nitrooxy)butanoate | ¹H NMR (300 MHz, DMSO-d$_6$) δ 1.00 (t, J = 7.16 Hz, 3H), 1.27-1.58 (m, 4H), 1.83-2.04 (m, 9 H), 2.07-2.30 (m, 3H), 2.45 (t, J = 7.25 Hz, 2H), 2.62 (t, J = 7.72 Hz, 2H), 2.97-3.12 (m, 2H), 3.63-3.77 (m, 1H), 3.88-3.97 (m, 1H), 4.41 (s, 1H), 4.51-4.63 (m, 3H), 5.20 (q, J = 6.47 Hz, 1H), 5.25-5.34 (m, 1H), 5.38-5.57 (m, 3H), 7.14-7.22 (m, 3H), 7.25-7.34 (m, 2H), 7.70 (s, 1H). | 585.0 |
| B-1 | 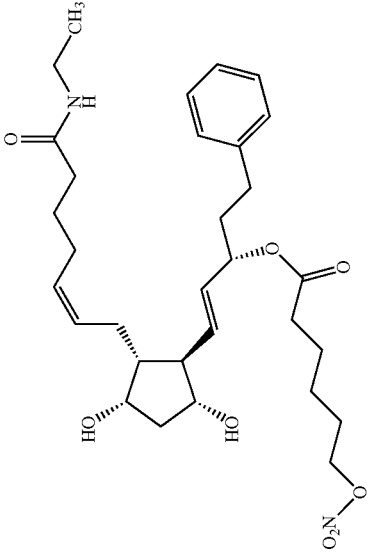 | (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 6-(Nitrooxy)hexanoate | ¹H NMR (400 MHz, DMSO-d$_6$) δ 0.97 (t, J = 7.20 Hz, 3H), 1.25-1.39 (m, 3H), 1.39-1.59 (m, 5 H), 1.60-1.71 (m, 2H), 1.78-2.01 (m, 7H), 2.03-2.25 (m, 3 H), 2.25-2.35 (m, 2H), 2.58 (t, J = 7.83 Hz, 2H), 2.96-3.10 (m, 2H), 3.60-3.72 (m, 1H), 3.85-3.95 (m, 1H), 4.40 (d, J = 4.80 Hz, 1H), 4.49 (t, J = 6.57 Hz, 2 H), 4.57 (d, J = 5.81 Hz, 1H), 5.15 (q, J = 6.32 Hz, 1H), 5.20-5.31 (m, 1H), 5.34-5.55 (m, 3H), 7.11-7.21 (m, 3H), 7.21-7.32 (m, 2H), 7.69 (br. s., 1H). | 597.2 M + Na |

TABLE 1-continued

Specific Examples

| Example number | Structure | Chemical Name | ¹HNMR | MS |
|---|---|---|---|---|
| C-1 | 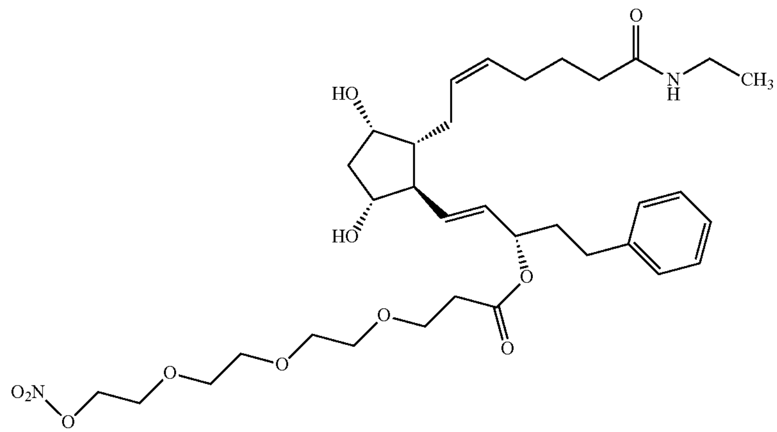 | (1S,2E)-3-{(1R,2R,3S,5R)-2-[(2Z)-7-(Ethylamino)-7-oxohept-2-en-1-yl]-3,5-dihydroxycyclopentyl]-1-(2-phenylethyl)prop-2-en-1-yl 3-(2-{2-[2-(Nitrooxy)ethoxy]ethoxy}ethoxy)propanoate | ¹H NMR (300 MHz, DMSO-d₆) δ 0.98 (t, J = 7.16 Hz, 3H), 1.22-1.36 (m, 1H), 1.40-1.56 (m, 3 H), 1.79-2.03 (m, 7H), 2.06-2.29 (m, 3H), 2.53-2.65 (m, 4 H), 2.94-3.11 (m, 2H), 3.44-3.53 (m, 8H), 3.60-3.71 (m, 5 H), 3.85-3.94 (m, 1H), 4.37-4.41 (m, 1H), 4.54-4.59 (m, 1 H), 4.61-4.65 (m, 2H), 5.13-5.22 (m, 1H), 5.23-5.30 (m, 1 H), 5.38-5.43 (m, 1H), 5.46-5.51 (m, 2H), 7.14-7.20 (m, 3 H), 7.23-7.31 (m, 2H), 7.63-7.73 (m, 1H). | 687.2 |
| D-1 | 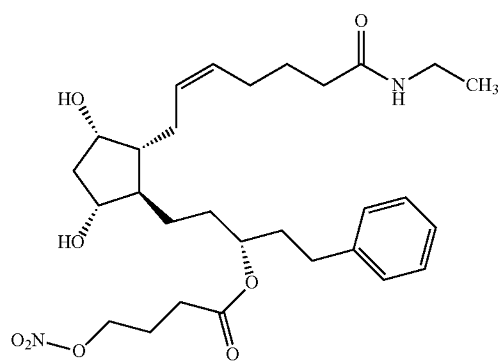 | (1R)-3-{(1R,2R,3S,5R)-2-[(2Z)-7-(Ethylamino)-7-oxohept-2-en-1-yl]-3,5-dihydroxycyclopentyl]-1-(2-phenylethyl)propyl 4-(Nitrooxy)butanoate | 1H NMR (400 MHz, chloroform-d) δ 1.06-1.17 (m, 3H), 1.29-1.48 (m, 2H), 1.61-1.79 (m, 6 H), 1.81-1.94 (m, 4H), 2.04 (qd, J = 6.74, 6.57 Hz, 4H), 2.08-2.26 (m, 4H), 2.31-2.48 (m, 3H), 2.63 (dt, J = 9.16, 6.54 Hz, 2H), 2.76-3.02 (m, 1H), 3.20-3.36 (m, 2H), 3.90 (br. s., 1H), 4.15 (br. s., 1H), 4.51 (t, J = 6.32 Hz, 2 H), 4.86-5.08 (m, 1H), 5.31-5.66 (m, 3H), 7.12-7.23 (m, 3 H), 7.25-7.36 (m, 2 H) | 549.3 |

TABLE 1-continued

Specific Examples

| Example number | Structure | Chemical Name | ¹HNMR | MS |
|---|---|---|---|---|
| E-1 | 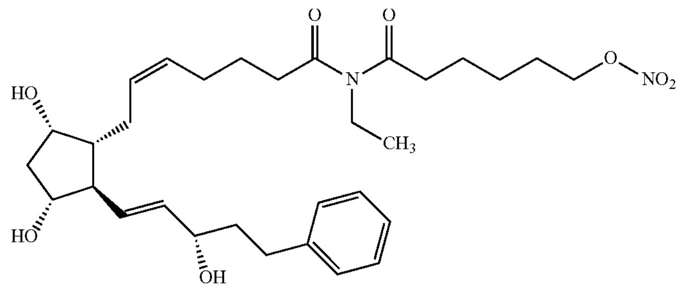 | 6-{[(5Z)-7-{(1R,2R,3R,5S)-3,5-Dihydroxy-2-[(1E,3S)-3-hydroxy-5-phenylpent-1-en-1-yl]cyclopentyl}hept-5-enoyl](ethyl)amino}-6-oxohexyl Nitrate | 1H NMR (400 MHz, DMSO-d₆) δ 1.00-1.10 (m, 3H), 1.25-1.41 (m, 4H), 1.48-1.60 (m, 5H), 1.61-1.77 (m, 5H), 1.89-2.06 (m, 5H), 2.09-2.26 (m, 4H), 3.55-3.73 (m, 4H), 3.83-3.97 (m, 2H), 4.36 (d, J = 4.80 Hz, 1H), 4.44-4.54 (m, 3H), 4.66 (d, J = 4.55 Hz, 1H), 5.21-5.32 (m, 1H), 5.35-5.52 (m, 3H), 7.11-7.20 (m, 3H), 7.25 (t, J = 7.45 Hz, 2H). | 597.2 M + Na |
| E-2 | 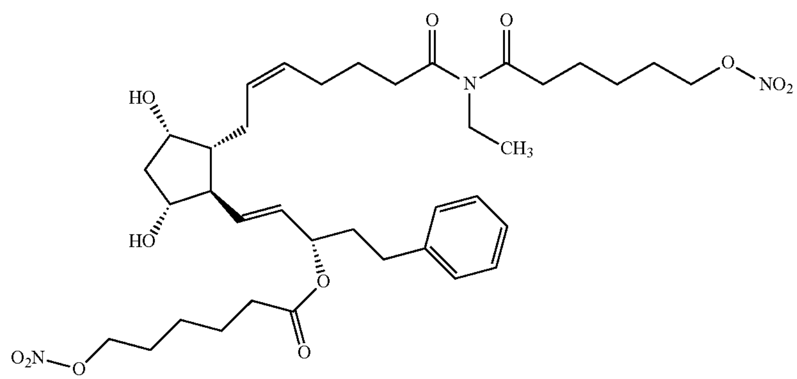 | (1S,2E)-3-{(1R,2R,3S,5R)-2-[(2Z)-7-{Ethyl[6-(nitrooxy)hexanoyl]amino}-7-oxohept-2-en-1-yl]-3,5-dihydroxycyclopentyl}-1-(2-phenylethyl)prop-2-en-1-yl 6-(Nitrooxy)hexanoate | ¹H NMR (700 MHz, DMSO-d6) δ 1.04 (t, J = 7.08 Hz, 3H), 1.26-1.38 (m, 5H), 1.42 (dt, J = 14.15, 2.87 Hz, 1H), 1.48-1.59 (m, 6H), 1.61-1.70 (m, 4H), 1.79-1.92 (m, 2H), 1.93-2.02 (m, 3H), 2.03-2.10 (m, 1H), 2.12-2.23 (m, 2H), 2.24-2.33 (m, 2H), 2.58 (t, J = 7.30 Hz, 4H), 2.65 (t, J = 7.30 Hz, 2H), 3.61 (q, J = 7.08 Hz, 2H), 3.64-3.69 (m, 1H), 3.90 (d, J = 3.54 Hz, 1H), 4.40 (d, J = 4.87 Hz, 1H), 4.50 (q, J = 6.49 Hz, 4H), 4.57 (d, J = 6.19 Hz, 1H), 5.16 (q, J = 5.75 Hz, 1H), 5.23-5.30 (m, 1H), 5.40-5.53 (m, 3H), 7.16 (d, J = 7.96 Hz, 3H), 7.26 (t, J = 7.74 Hz, 2H). | 756.2 M + Na |

TABLE 1-continued

Specific Examples

| Example number | Structure | Chemical Name | ¹HNMR | MS |
|---|---|---|---|---|
| F-1 | 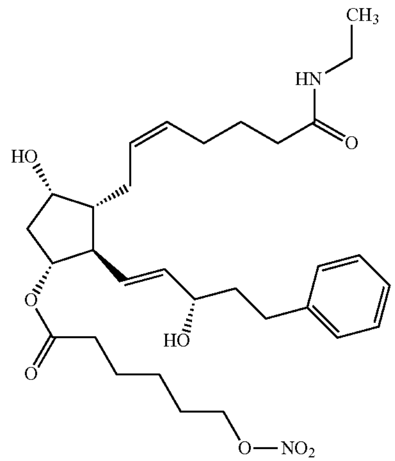 | (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 6-(Nitrooxy)hexanoate | ¹H NMR (700 MHz, DMSO-d₆) δ 0.98 (t, J = 7.30 Hz, 3H), 1.31 (dq, J = 7.74, 7.59 Hz, 2H), 1.42 (dd, J = 15.48, 3.98 Hz, 1H), 1.45-1.50 (m, 2H), 1.50-1.54 (m, 2H), 1.57-1.63 (m, 3H), 7.35, 7.19, 6.86 Hz, 2H), 1.63-1.70 (m, 2H), 1.95 (d, J = 7.08 Hz, 2H), 1.98 (t, J = 7.52 Hz, 3H), 2.11 (t, J = 15.70 Hz, 1H), 2.25 (t, J = 7.30 Hz, 2H), 2.33 (ddd, J = 14.82, 9.29, 5.53 Hz, 1H), 2.45 (t, J = 8.18 Hz, 1H), 2.55-2.64 (m, 2H), 2.98-3.06 (m, 2H), 3.91 (qd, J = 5.68, 5.53 Hz, 1H), 3.95 (d, J = 3.98 Hz, 1H), 4.46 (t, J = 6.63 Hz, 2H), 4.61 (d, J = 3.98 Hz, 1H), 4.75 (d, J = 4.87 Hz, 1H), 4.77 (dd, J = 7.74, 4.64 Hz, 1H), 5.24-5.32 (m, 1H), 5.38-5.49 (m, 3H), 7.16 (d, J = 7.52 Hz, 3H), 7.25 (t, J = 7.74 Hz, 2H), 7.70 (t, J = 4.64 Hz, 1H). | 597.2 M + Na⁺ |
| F-2 | 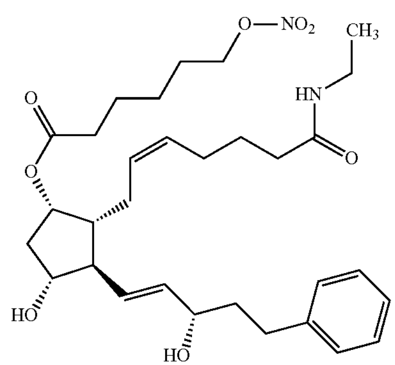 | (1S,2R,3R,4R)-2-[(2Z)-7-(Ethylamino)-7-oxohept-2-en-1-yl]-3-[(1E,3S)-3-hydroxy-5-phenylpent-1-en-1-yl]cyclopentyl 6-(Nitrooxy)hexanoate | ¹H NMR (700 MHz, DMSO-d₆) δ 0.98 (t, J = 7.30 Hz, 3H), 1.17-1.30 (m, 2H), 1.33-1.41 (m, 4H), 1.47 (dt, J = 15.48, 7.74 Hz, 2H), 1.56 (qd, J = 7.67, 7.52 Hz, 2H), 1.59-1.74 (m, 5H), 1.86 (dd, J = 13.71, 7.96 Hz, 1H), 1.90-1.96 (m, 1H), 1.98 (t, J = 7.52 Hz, 2H), 2.02 (t, J = 5.09 Hz, 2H), 2.17 (dt, J = 11.94, 7.96 Hz, 1H), 2.29 (q, J = 7.08 Hz, 2H), 2.36 (ddd, J = 14.82, 8.62, 6.19 Hz, 1H), 2.56-2.66 (m, 2H), 3.03 (dd, J = 7.30, 5.53 Hz, 2H), 3.76 (dd, J = 13.71, 2.65 Hz, 1H), 3.88-3.95 (m, 1H), 4.50 (t, J = 6.63 Hz, 2H), 4.73 (d, J = 4.42 Hz, 1H), 4.75 (d, J = 5.75 Hz, 1H), 4.91 (t, J = 4.64 Hz, 1H), 5.29 (d, J = 4.42 Hz, 1H), 5.36-5.44 (m, 1H), 5.46-5.53 (m, 1H), 7.10-7.20 (m, 3H), 7.26 (t, J = 7.52 Hz, 2H), 7.70 (qd, J = 5.68, 5.53 Hz, 1H). | 597.2 M + Na⁺ |

TABLE 1-continued

Specific Examples

| Example number | Structure | Chemical Name | ¹HNMR | MS |
|---|---|---|---|---|
| F-3 | 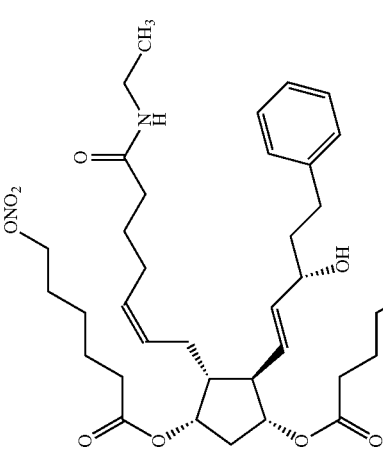 | (1R,3S,4R,5R)-4-[(2Z)-7-(Ethylamino)-7-oxohept-2-en-1-yl]-5-[(1E,3S)-3-hydroxy-5-phenylpent-1-en-1-yl]cyclopentane-1,3-diyl bis[6-(Nitrooxy)hexanoate] | ¹H NMR (400 MHz, DMSO-$d_6$) δ 7.71 (br. s., 1H), 7.23-7.32 (m, 2H), 7.17 (d, J = 7.33 Hz, 3H), 5.44-5.61 (m, 2H), 5.25-5.38 (m, 2H), 4.95-5.22 (m, 1H), 4.84-4.90 (m, 1H), 4.76-4.83 (m, 1H), 4.43-4.55 (m, 5H), 3.86-4.03 (m, 1H), 2.97-3.10 (m, 2H), 2.57-2.64 (m, 2H), 2.54-2.57 (m, 1H), 2.41-2.48 (m, 1H), 2.21-2.36 (m, 5H), 1.84-2.10 (m, 6H), 1.43-1.72 (m, 12H), 1.25-1.41 (m, 4H), 0.99 (t, J = 7.33 Hz, 3H). | 757.2 M + Na+ |
| F-4 | 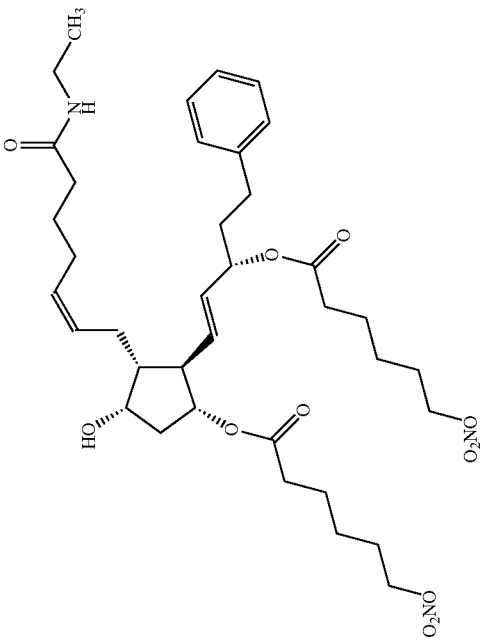 | (1S,2E)-3-[(1R,2R,3S,5R)-2-[(2Z)-7-(Ethylamino)-7-oxohept-2-en-1-yl]-3-hydroxy-5-{[6-(nitrooxy)hexanoyl]oxy}cyclopentyl]-1-(2-phenylethyl)prop-2-en-1-yl 6-(Nitrooxy)hexanoate | ¹H NMR (400 MHz, DMSO-$d_6$) δ 7.70 (br. s., 1H), 7.27 (t, J = 7.45 Hz, 2H), 7.11-7.22 (m, 3H), 5.35-5.46 (m, 1H), 5.48-5.57 (m, 2H), 5.21-5.34 (m, 1H), 5.09-5.18 (m, 1H), 4.74-4.85 (m, 1H), 4.66 (d, J = 4.04 Hz, 1H), 4.48 (dt, J = 12.95, 6.54 Hz, 5 H), 3.89-4.02 (m, 1H), 2.97-3.09 (m, 2H), 2.63-2.74 (m, 1H), 2.55-2.70 (m, 2H), 2.19-2.37 (m, 6H), 1.82-2.03 (m, 6H), 1.57-1.71 (m, 4H), 1.41-1.57 (m, 8H), 1.25-1.41 (m, 4H), 0.98 (t, J = 7.20 Hz, 3H). | 757.2 M + Na+ |

TABLE 1-continued

Specific Examples

| Example number | Structure | Chemical Name | ¹HNMR | MS |
|---|---|---|---|---|
| G-1 | 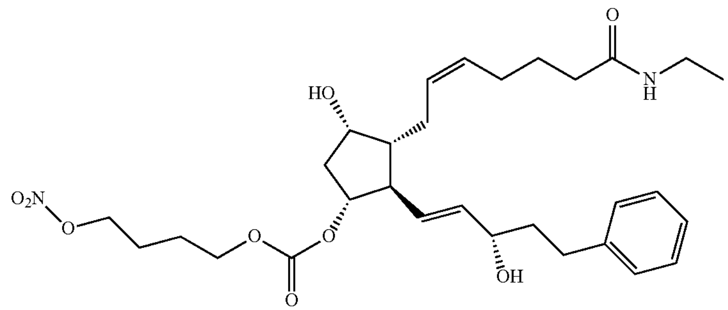 | (2R,3R)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butyl carbonate | ¹H NMR (400 MHz, DMSO-d6) δ 0.98 (t, J = 7.33 Hz, 3H), 1.35-1.57 (m, 4H), 1.58-1.74 (m, 6 H), 1.90-2.03 (m, 5H), 2.03-2.17 (m, 1H), 2.34 (ddd, J = 14.65, 9.09, 5.31 Hz, 1H), 2.42-2.49 (m, 1H), 2.52-2.63 (m, 2H), 2.96-3.09 (m, 2H), 3.85-3.98 (m, 2H), 3.99-4.14 (m, 2H), 4.44-4.57 (m, 2H), 4.62-4.74 (m, 2H), 4.78 (d, J = 4.55 Hz, 1H), 5.29 (dt, J = 10.67, 7.17 Hz, 1H), 5.37-5.55 (m, 3H), 7.10-7.20 (m, 3 H), 7.21-7.32 (m, 2H), 7.70 (t, J = 5.05 Hz, 1H). | 599.2 M + Na⁺ |
| G-2 | 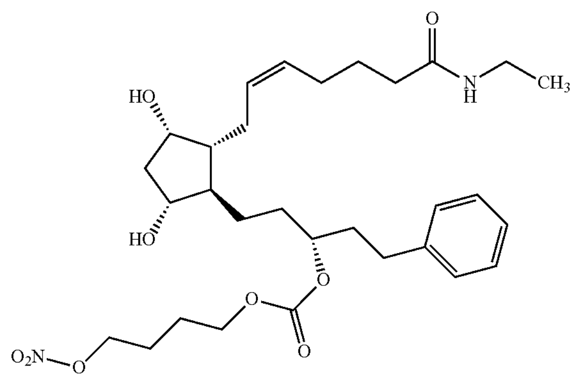 | (1S,2E)-3-{(1R,2R,3S,5R)-2-[(2Z)-7-(Ethylamino)-7-oxohept-2-en-1-yl]-3,5-dihydroxycyclopentyl]-1-(2-phenylethyl)prop-2-en-1-yl 4-(Nitrooxy)butyl carbonate | ¹H NMR (400 MHz, DMSO-d6) δ 0.98 (t, J = 7.33 Hz, 3H), 1.27-1.39 (m, 1H), 1.39-1.55 (m, 3 H), 1.60-1.83 (m, 4H), 1.80-2.03 (m, 7H), 2.04-2.26 (m, 3 H), 2.60 (t, J = 7.83 Hz, 2H), 2.97-3.10 (m, 2H), 3.60-3.74 (m, 2 H), 3.91 (br. s., 1H), 4.02-4.16 (m, 2H), 4.35-4.48 (m, 1H), 4.54 (t, J = 6.19 Hz, 1H), 4.57-4.69 (m, 1H), 4.97 (q, J = 6.74 Hz, 1H), 5.20-5.33 (m, 1H), 5.37-5.63 (m, 3H), 7.12-7.22 (m, 3H), 7.23-7.35 (m, 2H), 7.63-7.77 (m, 1H). | 599.2 M + Na |
| H-1 | 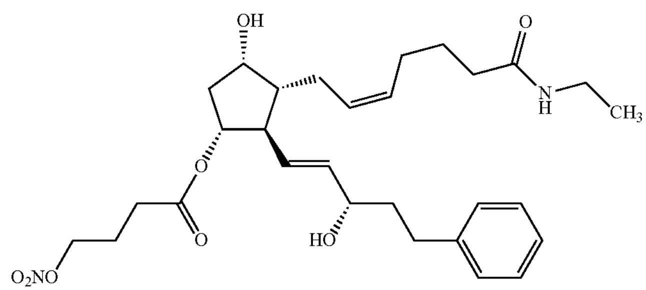 | (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butanoate | ¹H NMR (400 MHz, DMSO-d6) δ 7.71 (bs, 1H), 7.26 (t, J = 7.45 Hz, 2H), 7.10-7.19 (m, 3H), 5.37-5.51 (m, 3H), 5.21-5.35 (m, 1H), 4.70-4.83 (m, 2H), 4.63 (d, J = 4.04 Hz, 1H), 4.51 (t, J = 6.57 Hz, 2H), 3.86-3.99 (m, 2H), 2.96-3.10 (m, 2H), 2.53-2.64 (m, 3H), 2.26-2.41 (m, 3 H), 2.05-2.17 (m, 7H), 1.81-2.05 (m, 3H), 1.59-1.74 (m, 2 H), 1.34-1.54 (m, 4H), 0.98 (t, J = 7.20 Hz, 3H). | 569.2 M + Na⁺ |

TABLE 1-continued

Specific Examples

| Example number | Structure | Chemical Name | ¹HNMR | MS |
|---|---|---|---|---|
| J-1 | 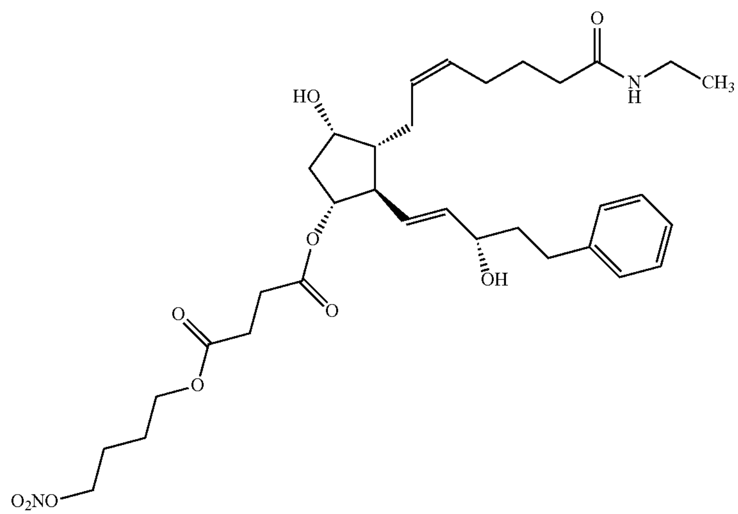 | (1R,2R,3R,4S)-3-[(2Z)-7-(Ethylamino)-7-oxohept-2-en-1-yl]-4-hydroxy-2-[(1E,3S)-3-hydroxy-5-phenylpent-1-en-1-yl]cyclopentyl 4-(Nitrooxy)butyl butanedioate | ¹H NMR (400 MHz, DMSO-d6) δ 7.70 (s, 1H), 7.26 (t, J = 7.45 Hz, 2 H), 7.17 (d, J = 7.83 Hz, 3H), 5.76 (s, 2H), 5.36-5.52 (m, 3H), 5.31 (s, 1H), 4.75 (d, J = 4.80 Hz, 2H), 4.62 (d, J = 4.04 Hz, 1H), 4.48-4.58 (m, 4H), 3.93 (d, J = 18.44 Hz, 2H), 2.96-3.09 (m, 2H), 2.63-2.71 (m, 1H), 2.56 (d, J = 1.77 Hz, 3H), 2.22-2.36 (m, 2H), 1.96 (s, 2H), 1.56-1.80 (m, 10H), 1.34-1.53 (m, 4 H), 0.98 (t, J = 7.20 Hz, 3H). | 655.2 M + Na⁺ |
| J-2 | 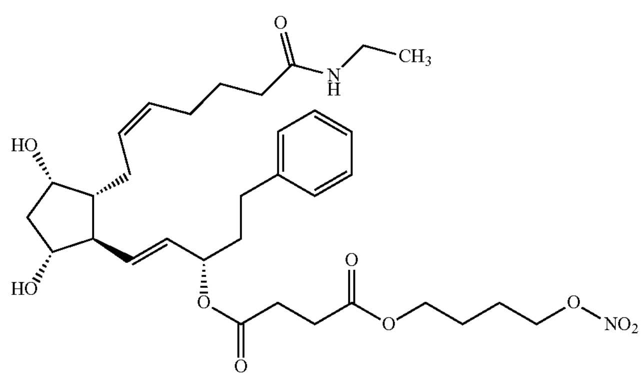 | (1R,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 4-(Nitrooxy)butyl Butanedioate | ¹H NMR (700 MHz, DMSO-d6) δ 0.98 (t, J = 7.30 Hz, 3H), 1.21-1.32 (m, 2H), 1.42 (dd, J = 15.48, 3.98 Hz, 2H), 1.44-1.55 (m, 4H), 1.56-1.70 (m, J = 7.35, 7.35, 7.19, 6.86 Hz, 4H), 1.85-2.05 (m, 5H), 2.05-2.17 (m, 1H), 2.25 (t, J = 7.30 Hz, 2H), 2.33 (ddd, J = 14.82, 9.29, 5.53 Hz, 1H), 2.46 (ddd, J = 11.83, 8.07, 7.96 Hz, 1H), 2.54-2.65 (m, 2H), 2.95-3.08 (m, 2H), 3.84-4.00 (m, 2H), 4.46 (t, J = 6.63 Hz, 2H), 4.61 (d, J = 3.98 Hz, 1H), 4.77 (ddd, J = 12.27, 4.53, 4.42 Hz, 2H), 5.21-5.35 (m, 1H), 5.36-5.55 (m, 3H), 7.16 (d, J = 7.52 Hz, 3H), 7.25 (t, J = 7.74 Hz, 2H), 7.70 (t, J = 4.64 Hz, 1H). | 656.2 M + Na⁺ |

TABLE 1-continued

Specific Examples

| Example number | Structure | Chemical Name | $^1$HNMR | MS |
|---|---|---|---|---|
| K-1 | 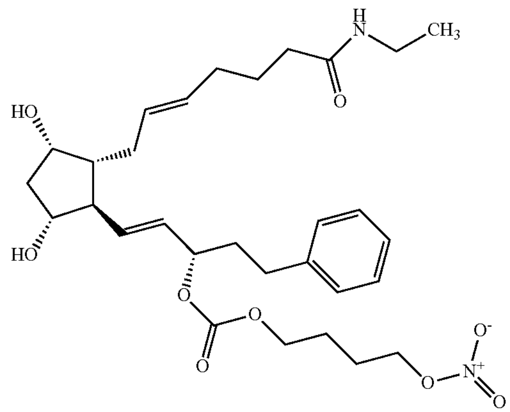 | (1S,2E)-3-{(1R,2R,3S,5R)-2-[(2E)-7-(Ethylamino)-7-oxohept-2-en-1-yl]-3,5-dihydroxycyclopentyl}-1-(2-phenylethyl)prop-2-en-1-yl 4-(Nitrooxy)butyl carbonate | $^1$H NMR (400 MHz, DMSO-d$_6$) δ 0.97 (t, J = 7.20 Hz, 3H), 1.27-1.56 (m, 4H), 1.59-1.80 (m, 4H), 1.80-2.04 (m, 7H), 2.04-2.28 (m, 3H), 2.60 (t, J = 7.83 Hz, 2H), 2.96-3.09 (m, 2H), 3.66 (t, J = 6.32 Hz, 2H), 3.92 (br. s., 1H), 4.09 (t, J = 5.81 Hz, 2H), 4.38 (br. s., 1H), 4.54 (t, J = 6.06 Hz, 1H), 4.60 (br. s., 1H), 4.96 (q, J = 6.65 Hz, 1H), 5.26-5.38 (m, 1H), 5.39-5.59 (m, 3H), 7.12-7.23 (m, 3H), 7.23-7.33 (m, 2H), 7.70 (br. s., 1H). | 599.29 M + Na |
| M-1 | 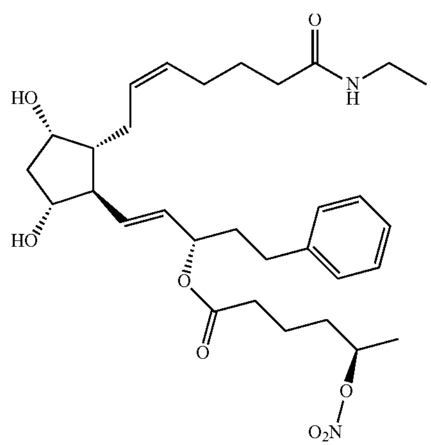 | (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl (5S)-5-(Nitrooxy)hexanoate | $^1$H NMR (300 MHz, DMSO-d6) δ 7.68 (1H, t); 7.25 (2H, m); 7.17 (3H, m); 5.48 (3H, m); 5.35-5.05 (3H, m); 4.57 (1H, d); 4.39 (1H, d); 3.90 (1H, m); 3.67 (1H, m); 3.03 (2H, m); 2.59 (2H, t); 2.33 (2H, t); 2.15 (4H, m); 1.96 (7H, m); 1.70-1.40 (7H, m); 1.30 (3H, d); 1.00 (3H, t). | |

TABLE 1-continued

Specific Examples

| Example number | Structure | Chemical Name | ¹HNMR | MS |
|---|---|---|---|---|
| M-2 | 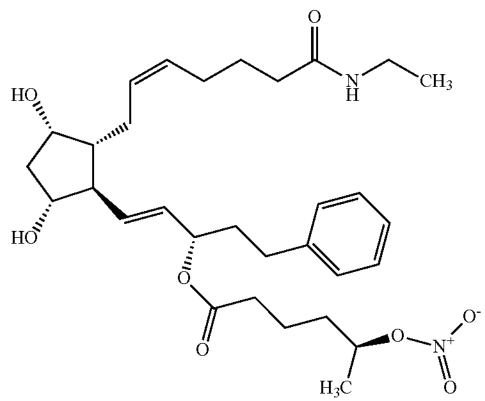 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5S)-5-(nitrooxy)hexanoate | (300 MHz, DMSO-d₆): δ 7.68 (1H, t); 7.25 (2H, m); 7.17 (3H, m); 5.48 (3H, m); 5.35-5.05 (3H, m); 4.57 (1H, d); 4.39 (1H, d); 3.90 (1H, m); 3.67 (1H, m); 3.03 (2H, m); 2.59 (2H, t); 2.33 (2H, t); 2.15 (4H, m); 1.96 (7H; m); 1.70-1.40 (7H, m); 1.30 (3H, d); 1.00 (3H, t). | |
| N-1 | 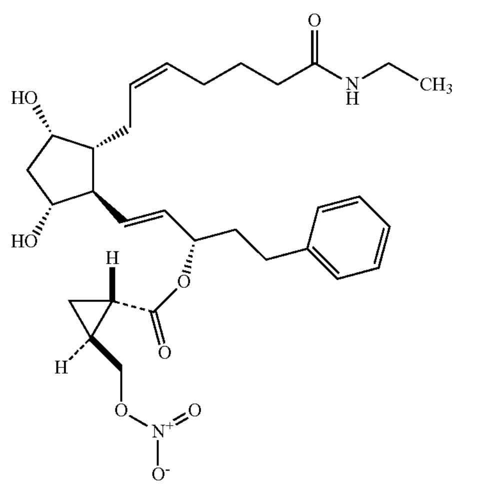 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (1S,2S)-2-[(nitrooxy)methyl]cyclopropanecarboxylate | (400 MHz, DMSO-d₆): δ 7.70 (br. s., 1H), 7.27 (t, J = 7.45 Hz, 2H), 7.13-7.22 (m, 3H), 5.37-5.52 (m, 3H), 5.21-5.34 (m, 1 H), 5.14 (d, J = 5.81 Hz, 1 H), 4.47-4.58 (m, 2H), 4.31-4.45 (m, 2H), 3.85-3.95 (m, 1H), 3.63-3.74 (m, 1H), 2.96-3.09 (m, 2H), 2.53-2.64 (m, 2 H), 2.04-2.24 (m, 3H), 1.80-1.97 (m, 6H), 1.56-1.72 (m, 3H), 1.38-1.53 (m, 3H), 1.24-1.37 (m, 1H), 1.04-1.14 (m, 2 H), 0.92-1.02 (m, 3H), | 581.2 M + Na |

| Example number | Structure | Chemical Name | ¹HNMR | MS |
|---|---|---|---|---|
| O-1 | 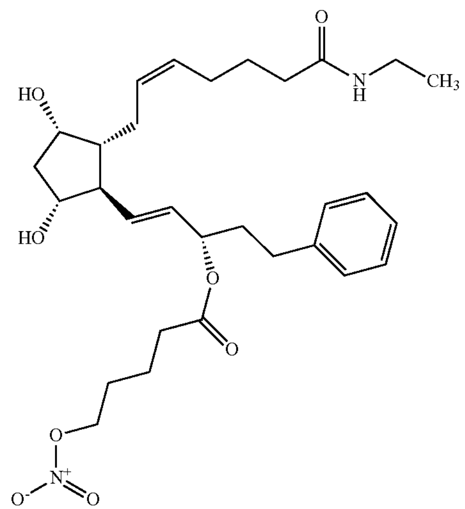 | (1S,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 5-(Nitrooxy)pentanoate | (400 MHz, DMSO-d₆) δ 7.68 (t, J = 5.05 Hz, 1H), 7.22-7.32 (m, 2H), 7.12-7.21 (m, 3H), 5.35-5.55 (m, 3H), 5.11-5.31 (m, 2H), 4.47-4.61 (m, 3H), 4.40 (d, J = 4.80 Hz, 1H), 3.85-3.95 (m, 1H), 3.62-3.76 (m, 1H), 2.95-3.11 (m, 2H), 2.53-2.63 (m, 2H), 2.35 (t, J = 7.20 Hz, 2H), 2.03-2.27 (m, 3H), 1.81-2.01 (m, 7H), 1.55-1.72 (m, 4H), 1.38-1.52 (m, 3H), 1.26-1.35 (m, 1H), 0.97 (t, J = 7.20 Hz, 3H). | |
| P-1 | 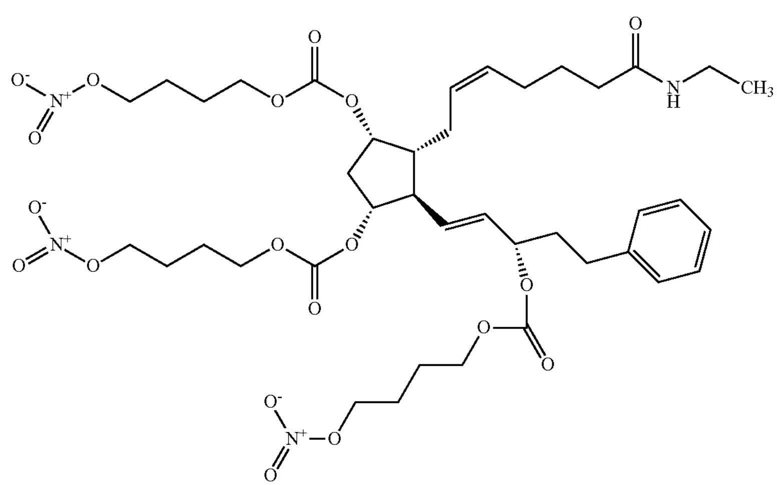 | (1R,3S,4R,5R)-4-[(2Z)-7-(ethylamino)-7-oxohept-2-en-1-yl]-5-[(1E,3S)-3-({[4-(nitrooxy)butoxy]carbonyl}oxy)-5-phenylpent-1-en-1-yl]cyclopentane-1,3-diyl bis[4-(nitrooxy)butyl] biscarbonate | (400 MHz, DMSO-d₆) δ 0.98 (t, J = 7.20 Hz, 3H), 1.41-1.55 (m, 2H), 1.59-1.78 (m, 13H), 1.80-2.15 (m, 9H), 2.43-2.50 (m, 1H), 2.54-2.65 (m, 3H), 2.96-3.10 (m, 2H), 3.99-4.18 (m, 6H), 4.33-4.33 (m, 0H), 4.45-4.62 (m, 6H), 4.81 (ddd, J = 8.91, 7.26, 3.79 Hz, 1H), 4.87 (t, J = 4.67 Hz, 1H), 4.93-5.04 (m, 1H), 5.25-5.41 (m, 2H), 5.59-5.72 (m, 2H), 7.13-7.23 (m, 3H), 7.23-7.34 (m, 2H), 7.69 (t, J = 5.18 Hz, 1H). | |

TABLE 1-continued

Specific Examples

| Example number | Structure | Chemical Name | ¹HNMR | MS |
|---|---|---|---|---|
| P-2 | 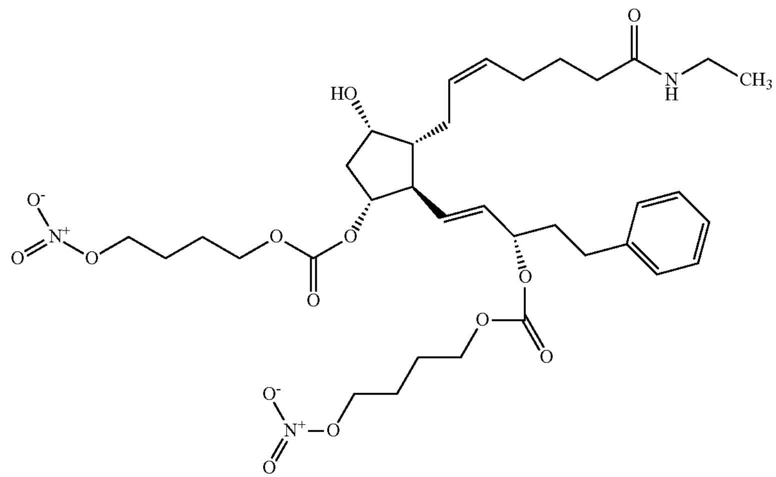 | (1S,2E)-3-[(1R,2R,3S,5R)-2-[(2Z)-7-(ethylamino)-7-oxohept-2-en-1-yl]-3-hydroxy-5-({[4-(nitrooxy)butoxy]carbonyl}oxy)cyclopentyl]-1-(2-phenylethyl)prop-2-en-1-yl 4-(nitrooxy)butyl carbonate | (400 MHz, DMSO-d₆): δ 0.97 (t, J = 7.20 Hz, 3H), 1.38-1.58 (m, 4H), 1.58-1.77 (m, 8H), 1.79-2.03 (m, 7H), 2.05-2.17 (m, 1H), 2.34 (ddd, J = 14.78, 9.09, 5.43 Hz, 1H), 2.44-2.48 (m, 1H), 2.52-2.63 (m, 2H), 2.96-3.07 (m, 2H), 3.95 (d, J = 4.04 Hz, 1H), 3.98-4.15 (m, 4H), 4.51 (ddd, J = 12.88, 6.32, 6.06 Hz, 4H), 4.64-4.76 (m, 2H), 4.96 (q, J = 6.48 Hz, 1H), 5.28 (dt, J = 10.93, 7.17 Hz, 1H), 5.34-5.46 (m, 1H), 5.48-5.69 (m, 2H), 7.11-7.21 (m, 3H), 7.22-7.32 (m, 2H), 7.69 (t, J = 5.31 Hz, 1H). | 760.2 M + Na |
| P-3 | 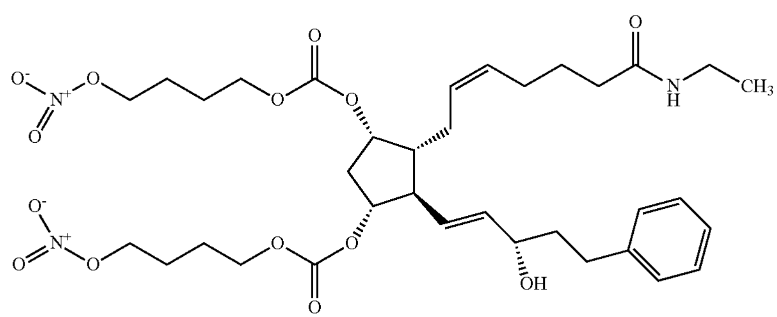 | (1R,3S,4R,5R)-4-[(2Z)-7-(ethylamino)-7-oxohept-2-en-1-yl]-5-[(1E,3S)-3-hydroxy-5-phenylpent-1-en-1-yl]cyclopentane-1,3-diyl bis[4-(nitrooxy)butyl] biscarbonate | (400 MHz, DMSO-d₆): δ 0.97 (t, J = 7.20 Hz, 3H), 1.41-1.51 (m, 2H), 1.58-1.76 (m, 11H), 1.76-2.12 (m, 7H), 2.38-2.48 (m, 1H), 2.52-2.65 (m, 3H), 2.96-3.08 (m, 2H), 3.88-3.98 (m, 1H), 4.00-4.15 (m, 4H), 4.52 (dt, J = 17.62, 6.09 Hz, 4H), 4.73-4.83 (m, 2H), 4.86 (t, J = 4.93 Hz, 1H), 5.25-5.39 (m, 2H), 5.43-5.63 (m, 2H), 7.10-7.20 (m, 3H), 7.21-7.30 (m, 2H), 7.69 (s, 1H). | 760.2 M + Na |

TABLE 1-continued

Specific Examples

| Example number | Structure | Chemical Name | ¹HNMR | MS |
|---|---|---|---|---|
| Q-1 | 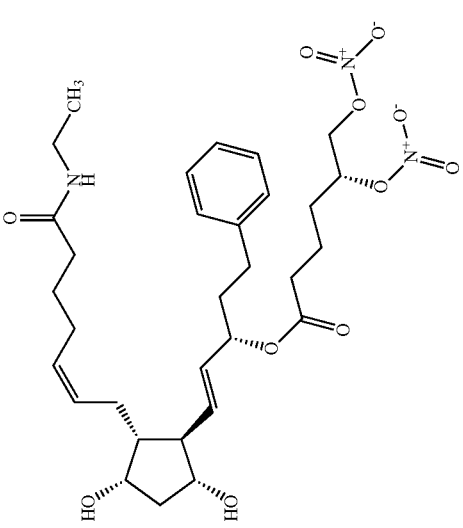 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5R)-5,6-bis(nitrooxy)hexanoate | (300 MHz, DMSO-d6): δ 0.97 (t, 3H), 1.35 (m, 1 H), 1.40-1.65 (m, 3H), 1.60-1.80 (m, 4H), 1.80-2.00 (m, 7H), 2.05-2.25 (3H), 2.34-2.38 (m, 2H), 2.57-2.62 (m, 2 H), 3.01-3.05 (m, 2H), 3.60-3.71 (m, 1H), 3.91 (m, 1H), 4.40 (d, 1 OH), 4.57 (d, 1 OH), 4.67-4.96 (m, 2H), 5.17 (m, 1 H), 5.28 (m, 1H), 5.41-5.50 (m, 4H), 7.16-7.19 (m, 3H), 7.25-7.30 (m, 2 H), 7.69 (s, 1H). | 636.2 M + 1 |
| Q-2 | 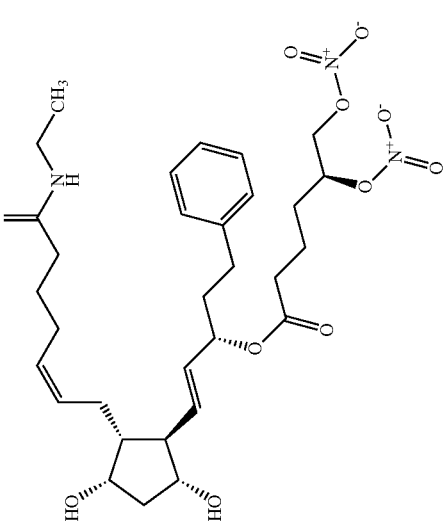 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5S)-5,6-bis(nitrooxy)hexanoate | (300 MHz, DMSO-d6): δ 0.97 (t, 3H), 1.35 (m, 1 H), 1.40-1.65 (m, 3H), 1.60-1.80 (m, 4H), 1.80-2.00 (m, 7H), 2.05-2.25 (3H), 2.34-2.38 (m, 2H), 2.57-2.62 (m, 2 H), 3.01-3.05 (m, 2H), 3.60-3.71 (m, 1H), 3.91 (m, 1H), 4.40 (d, 1 OH), 4.57 (d, 1 OH), 4.67-4.96 (m, 2H), 5.17 (m, 1 H), 5.28 (m, 1H), 5.41-5.50 (m, 4H), 7.16-7.19 (m, 3H), 7.25-7.30 (m, 2 H), 7.69 (s, 1H). | 636.2 M + 1 |

TABLE 1-continued

Specific Examples

| Example number | Structure | Chemical Name | ¹HNMR | MS |
|---|---|---|---|---|
| R-1 | 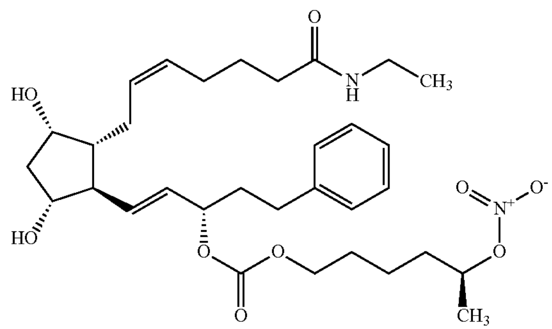 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5S)-5-(nitrooxy)hexyl carbonate | (300 MHz, DMSO-d6): δ 0.97 (t, 3H), 1.30 (d, 3 H), 1.30-1.70 (m, 10H), 1.80-2.00 (m, 7H), 2.05-2.25 (3H), 2.60 (m, 2 H), 3.02 (m, 2H), 3.68 (m, 1H), 3.90 (m, 1H), 4.05 (m, 2H), 4.40 (d, 1 OH), 4.60 (d, 1 OH), 4.96 (m, 1H), 5.12 (m, 1H), 5.28 (m, 1H), 5.37-5.62 (m, 3 H), 7.16-7.19 (m, 2H), 7.25-7.30 (m, 2H), 7.69 (s, 1H). | 605 M + 1 |
| R-2 | 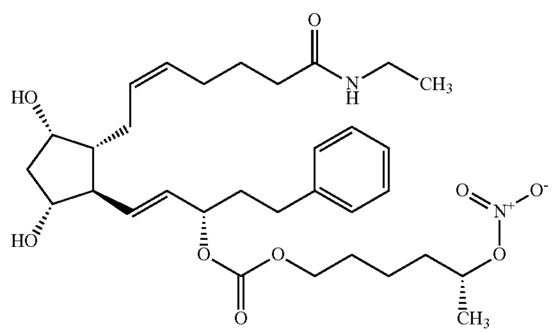 | (1S,2E)-3-{(1R,2R,3S,5R)-2-[(2Z)-7-(ethylamino)-7-oxohept-2-en-1-yl]-3,5-dihydroxycyclopentyl}-1-(2-phenylethyl)prop-2-en-1-yl (5R)-5-(nitrooxy)hexyl carbonate | (300 MHz, DMSO-d6): δ 0.97 (t, 3H), 1.30 (d, 3 H), 1.30-1.70 (m, 10H), 1.80-2.00 (m, 7H), 2.05-2.25 (3H), 2.60 (m, 2 H), 3.02 (m, 2H), 3.68 (m, 1H), 3.90 (m, 1H), 4.05 (m, 2H), 4.40 (d, 1 OH), 4.60 (d, 1 OH), 4.96 (m, 1H), 5.12 (m, 1H), 5.28 (m, 1H), 5.37-5.62 (m, 3 H), 7.16-7.19 (m, 2H), 7.25-7.30 (m, 2H), 7.69 (s, 1H). | 605 M + 1 |

TABLE 1-continued
Specific Examples
| Example number | Structure | Chemical Name | $^1$HNMR | MS |
|---|---|---|---|---|
| S-1 | 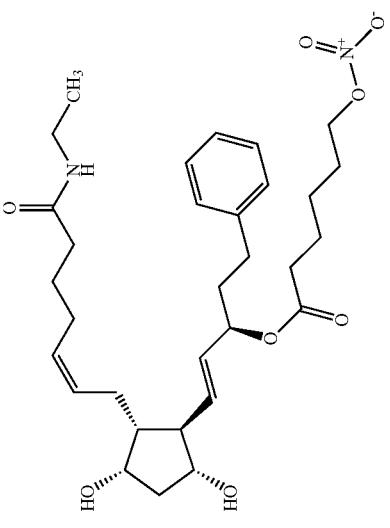 | (1R,2E)-3-{(1R,2R,3S,5R)-2-[(2Z)-7-(Ethylamino)-7-oxohept-2-en-1-yl]-3,5-dihydroxycyclopentyl}-1-(2-phenylethyl)prop-2-en-1-yl 6-(Nitrooxy)hexanoate | (300 MHz, CDCl$_3$): δ, 1.15 (t, J = 7.3 Hz, 3H), 2.66 (t, J = 7.5 Hz, 1H), 3.30 (ddd, J = 1.0, 7.3, 13.0 Hz, 2H), 3.97 (bs, 1H), 4.20 (bs, 1H), 4.46 (t, J = 6.6 Hz, 2H), 5.28 (dd, J = 6.6, 13.2 Hz, 1H), 5.39 (m, 1H). | 597.30 M + Na |

Efficacy of Selected Examples. Intraocular Pressure Measured by Pneumatonometry

Intraocular pressure was measured by pneumatonometry in ocular normotensive dogs (Beagle) and ocular hypertensive non human primates (for example, although dosing different here, see hypertensive primates described by Toris, C. B.; Zhan, G.-L.; Feilmeier, M. R.; Camras, C. B.; McLaughlin, M. A. J. Ocular Pharm. Ther. 2006, 22, 86-92). As described, only one eye is hypertensive in this primate model. Studies were performed in conscious animals (n=8/study) trained to accept pneumatonometry. The test compound and controls were formulated in a 10 mM citrate buffer vehicle at pH 5.5 with 0.5% Tween 80 and 0.02% benzalkonium chloride, and were administered in the evening. All test compounds were formulated at a dose equimolar to 0.03% Bimatoprost. Intraocular pressure was measured at −12 (baseline), 12 and 18 hours post treatment. Tetracaine hydrochloride (0.5%) was used to anesthetize the cornea when the intraocular pressure measurements were taken.

In the primate model, the hypertensive eye received 2×25 µl volume drops of the test compound. After a washout period of one week, the ocular hypertensive eye was then dosed with Bimatoprost (2×25 µl volume drops) as a control. The contralateral, normotensive eye was not treated in the study. In the normotensive dog model, the test compound was administered topically to one eye in a 50 µl volume drop. The contralateral eye received a 50 µl volume drop of blank vehicle or Bimatoprost (in the case of the head-to-head study only) to serve as a control. Students paired t test was used to compare treatment with test compound vs vehicle or Bimatoprost control for significant differences.

Tables 2 and 3 describe the intraocular pressure (IOP) changes that were seen following topical application of novel NO-prostamides in ocular hypertensive non-human primates and normotensive dogs. ΔEmax represents the maximal efficacy as compared to baseline (BL) values. ΔΔEmax reflects the difference in IOP from compound-treated eye over that seen for vehicle-treated eye at the timepoint wherein maximum IOP reduction for compound was seen. The percent change from vehicle control was the percentage change in IOP reduction conferred by compound over that for vehicle (set at 100%). Tmax represents the time point at which maximum IOP reduction of compound was observed.

TABLE 2

Primate IOP Summary - Example B-1 and Bimatoprost

| Compound | Conc (%) | BL (mmHg) | ΔEmax (mm Hg) | % change from Baseline (%) | Tmax (h) |
|---|---|---|---|---|---|
| Bimatoprost | 0.03 | 32 | −4.8* | −13 | 18 |
| Example B-1 | 0.04 | 32 | −7.7** | −24** | 18 |

*p < 0.05 vs. baseline,
**p < 0.01 vs. baseline

TABLE 3

Dog IOP Summary - NO-Prostamide test compounds and Bimatoprost

| Compound | Conc (%) | BL (mmHg) | ΔΔEmax (mm H/g) | % Change from vehicle control (%) | Tmax (h) |
|---|---|---|---|---|---|
| Bimatoprost | 0.03 | 20.2 | −4.0** | −16** | 12 |
| Example B-1 | 0.04 | 21.1 | −5.8** | −28** | 18 |
|  |  | 22.1 | −7.4** | −34** | 18 |
| Example F-1 | 0.04 | 19 | −4.9** | −25** | 12 |
| Example A-1 | 0.04 | 18 | −3.6** | −20** | 12 |
| Example C-1 | 0.04 | 21 | −3.6** | 18** | 12 |
| Example G-1 | 0.04 | 19 | −3.8** | 20** | 18 |

**p < 0.01 vs. vehicle control

FIG. 1 illustrates topical dosing of Example B-1 and Bimatoprost in the ocular hypertensive primate, FIG. 1 illustrates the intraocular pressure (IOP) response in ocular hypertensive primates to B-1 (squares) and Bimatoprost (circles), expressed as percent change from baseline.

Figure 2:
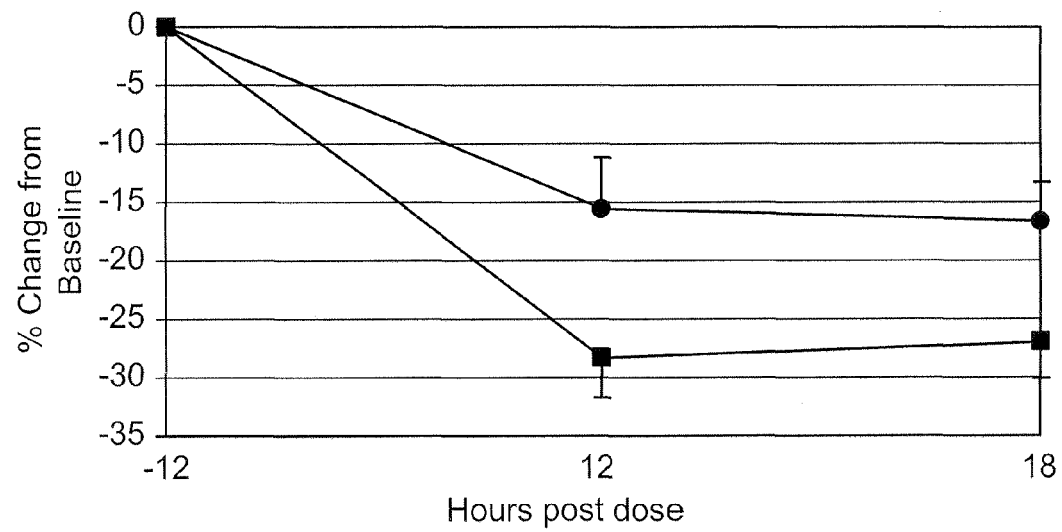
FIG. 2 is a graph illustrating the intraocular pressure response when administering an example compound and Bimatoprost to a normotensive dog in accordance with aspects of the present invention.

FIG. 2 illustrates topical dosing of Example B-1 and Bimatoprost in the normotensive dog.

FIG. 2 illustrates the IOP response in ocularnormotensive dogs to B-1 (squares) and Bimatoprost (circles), expressed as percent change from baseline.

What is claimed is:

1. A compound of formula (I):

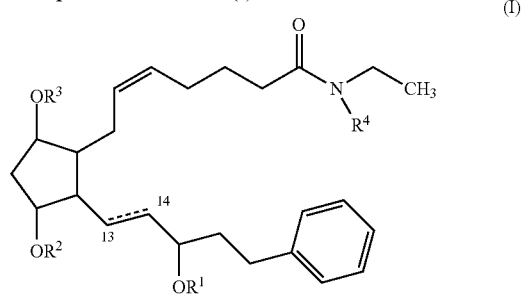

(I)

wherein:
  the symbol ═ represents a single or double bond in the cis or trans configuration;
  $R^1$, $R^2$, $R^3$ and $R^4$ are each independently H, —C(O)$R^5$—ONO$_2$, —C(O)OR$^5$—ONO$_2$, —C(O)$R^5R^6$—ONO$_2$, —[C(O)$R^5$]$_m$—ONO$_2$, —C(O)$R^5$—[OC(O)$R^6$]$_n$—ONO$_2$, —C(O)$R^5$—[(O)CR$^6$]$_n$—ONO$_2$, —C(O)$R^5$—[(O)$R^6$]$_n$—ONO$_2$, —[C(O)$R^5$]$_m$—[C(O)OR$^6$]$_n$—ONO$_2$, with the proviso that $R^1$, $R^2$, $R^3$ and $R^4$ cannot all be H;
  each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic;
  wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$;
  each m is independently selected from 1 to 6; and
  each n is independently selected from 1 to 6;
or a pharmaceutically acceptable salt or stereoisomer thereof.

2. A compound of formula (I) according to claim 1 wherein:
  $R^1$ and $R^2$ are both H; and
  the bond between the carbon atoms in positions 13 and 14 is a double bond.

3. A compound of formula (I) according to claim 1 wherein:
R$^1$, R$^2$ and R$^3$ are H; and
the bond between the carbon atoms in positions 13 and 14 is a double bond.

4. A compound according to claim 1 of Formula (II):

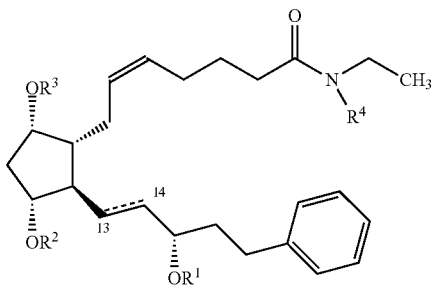

(II)

wherein:
the symbol = represents a single or double bond in the cis or trans configuration;
R$^1$, R$^2$, R$^3$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—(OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$_5$]$_m$—[C(O)OR$^6$]$_n$—ONO$_2$, with the proviso that R$^1$, R$^2$, R$^3$ and R$^4$ cannot all be H;
each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;
wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;
each m is independently selected from 1 to 6; and
each n is independently selected from 1 to 6;
or a pharmaceutically acceptable salt or stereoisomer thereof.

5. A compound of formula (II) according to claim 4 wherein:
R$^1$ and R$^2$ are both H; and
the bond between the carbon atoms in positions 13 and 14 is a double bond.

6. A compound according to claim 1 of Formula (III):

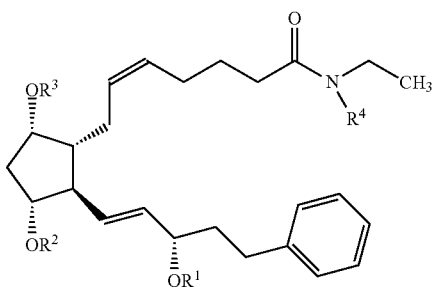

(III)

wherein:
R$^1$, R$^2$, R$^3$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^1$, R$^2$, R$^3$ and R$^4$ cannot all be H;
each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;
wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;
each m is independently selected from 1 to 6; and
each n is independently selected from 1 to 6;
or a pharmaceutically acceptable salt or stereoisomer thereof.

7. A compound according to claim 1 of Formula (IV):

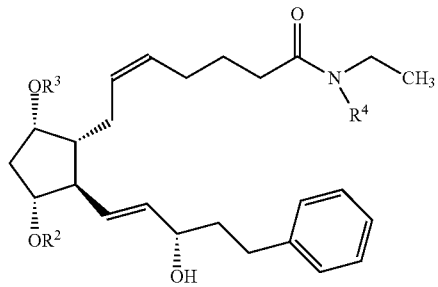

(IV)

wherein:
R$^2$, R$^3$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—(OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^2$, R$^3$ and R$^4$ cannot all be H;
each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;
wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;
each m is independently selected from 1 to 6;
each n is independently selected from 1 to 6;
or a pharmaceutically acceptable salt or stereoisomer thereof.

8. A compound according to claim 1 of Formula (V):

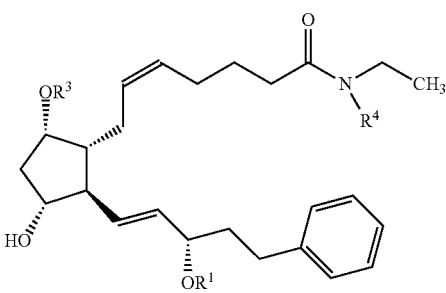

(V)

wherein:
R$^1$, R$^3$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^1$, R$^3$ and R$^4$ cannot all be H;

each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;

wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;

each m is independently selected from 1 to 6;
each n is independently selected from 1 to 6;
or a pharmaceutically acceptable salt or stereoisomer thereof.

9. A compound according to claim 1 of Formula (VI):

(VI)

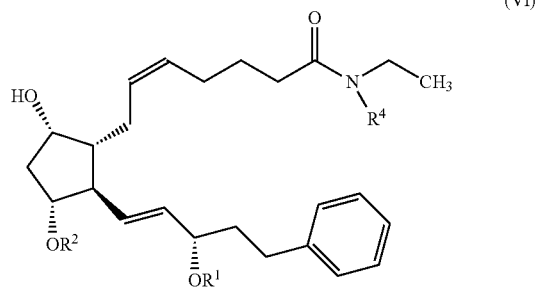

wherein:
R$^1$, R$^2$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^1$, R$^2$ and R$^4$ cannot all be H;

each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;

wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;

each m is independently selected from 1 to 6; and
each n is independently selected from 1 to 6;
or a pharmaceutically acceptable salt or stereoisomer thereof.

10. A compound according to claim 1 of Formula (VII):

(VII)

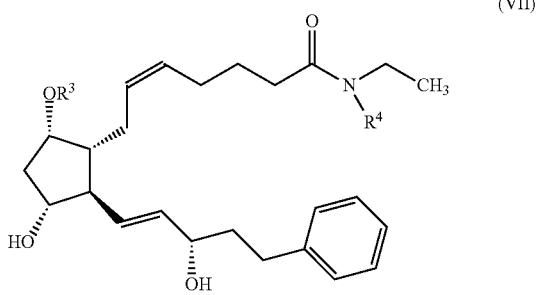

wherein:
R$^3$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^3$ and R$^4$ cannot both be H;

each R$^5$ and R$^6$, which may be the same or different, is independently selected from C$_{1-9}$ alkyl, C$_{2-9}$ alkenyl, C$_{2-9}$ alkynyl, alkoxy, C$_{2-9}$ alkoxyalkyl, C$_{3-10}$ cycloalkyl, C$_{3-10}$ cycloalkoxy and C$_{4-10}$ membered heterocyclic;

wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyano, nitro, azido, N, O, S, NO$_2$ or ONO$_2$;

each m is independently selected from 1 to 6; and
each n is independently selected from 1 to 6;
or a pharmaceutically acceptable salt or stereoisomer thereof.

11. A compound according to claim 1 of Formula (VIII):

(VIII)

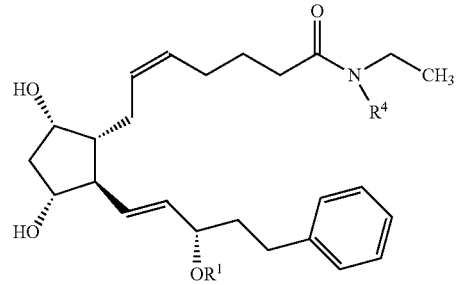

wherein:
R$^1$ and R$^4$ are each independently H, —C(O)R$^5$—ONO$_2$, —C(O)OR$^5$—ONO$_2$, —C(O)R$^5$R$^6$—ONO$_2$, —[C(O)R$^5$]$_m$—ONO$_2$, —C(O)R$^5$—[OC(O)R$^6$]$_n$—ONO$_2$, —C(O)R$^5$—[(O)CR$^6$]$_n$—ONO$_2$, —C(O)R$^5$—[(O)R$^6$]$_n$—ONO$_2$, —[C(O)R$^5$]$_m$—[C(O)OR$^6$]$_n$—ONO$_2$, with the proviso that R$^1$ and R$^4$ cannot both be H;

each R$^5$ and R$^6$, which may be the same or different, is independently selected from C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic;

wherein each of said C$_{1-9}$ alkyl, C$_{2-9}$ alkenyl, C$_{2-9}$ alkynyl, C$_{1-9}$ alkoxy, C$_{2-9}$ alkoxyalkyl, C$_{3-10}$ cycloalkyl, C$_{3-10}$ cycloalkoxy and C$_{4-10}$ membered heterocyclic moieties is optionally substituted with one or more of halo, cyan, nitro, azido, N, O, S, NO$_2$ or ONO$_2$;

each m is independently selected from 1 to 6; and
each n is independently selected from 1 to 6;
or a pharmaceutically acceptable salt or stereoisomer thereof.

12. A compound according to claim 1 of Formula (IX):

(IX)

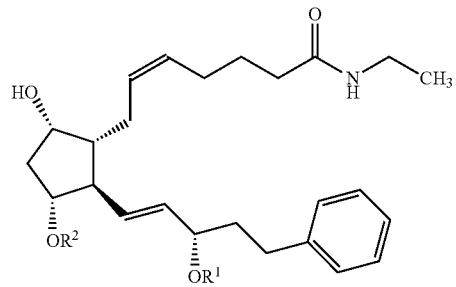

wherein:

$R^1$ and $R^2$ are each independently H, —C(O)$R^5$—ONO$_2$, —C(O)O$R^5$—ONO$_2$, —C(O)$R^5R^6$—ONO$_2$, —[C(O)$R^5$]$_m$—ONO$_2$, —C(O)$R^5$—[OC(O)$R^6$]$_n$—ONO$_2$, —C(O)$R^5$—[(O)C$R^6$]$_n$—ONO$_2$, —C(O)$R^5$—[(O)$R^6$]$_n$—ONO$_2$, —[C(O)$R^5$]$_m$—[C(O)O$R^6$]$_n$—ONO$_2$, with the proviso that $R^1$ and $R^2$ cannot both be H;

each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic;

wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$;

each m is independently selected from 1 to 6; and each n is independently selected from 1 to 6;

or a pharmaceutically acceptable salt or stereoisomer thereof.

13. A compound according to claim 1 of Formula (X)

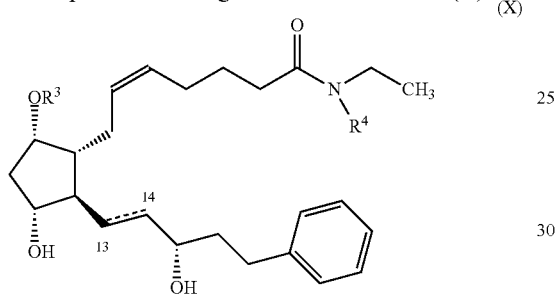

wherein:

the symbol ═ represents a single or double bond in the cis or trans configuration;

$R^3$ and $R^4$ are each independently H, —C(O)$R^5$—ONO$_2$, —C(O)O$R^5$—ONO$_2$, —C(O)$R^5R^6$—ONO$_2$, —[C(O)$R^5$]$_m$—ONO$_2$, —C(O)$R^5$—[OC(O)$R^6$]$_n$—ONO$_2$, —C(O)$R^5$—[(O)C$R^6$]$_n$—ONO$_2$, —C(O)$R^5$—[(O)$R^6$]$_n$—ONO$_2$, —[C(O)$R^5$]$_m$—[C(O)O$R^6$]$_n$—ONO$_2$, with the proviso that $R^3$ and $R^4$ cannot both be H;

each $R^5$ and $R^6$, which may be the same or different, is independently selected from $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic;

wherein each of said $C_{1-9}$ alkyl, $C_{2-9}$ alkenyl, $C_{2-9}$ alkynyl, $C_{1-9}$ alkoxy, $C_{2-9}$ alkoxyalkyl, $C_{3-10}$ cycloalkyl, $C_{3-10}$ cycloalkoxy and $C_{4-10}$ membered heterocyclic moieties is optionally substituted with one or more of halo, cyano, nitro, azido, N, O, S, NO$_2$ or ONO$_2$:

each m is independently selected from 1 to 6; and each n is independently selected from 1 to 6;

or a pharmaceutically acceptable salt or stereoisomer thereof.

14. A compound according to claim 1 selected from the group consisting of:

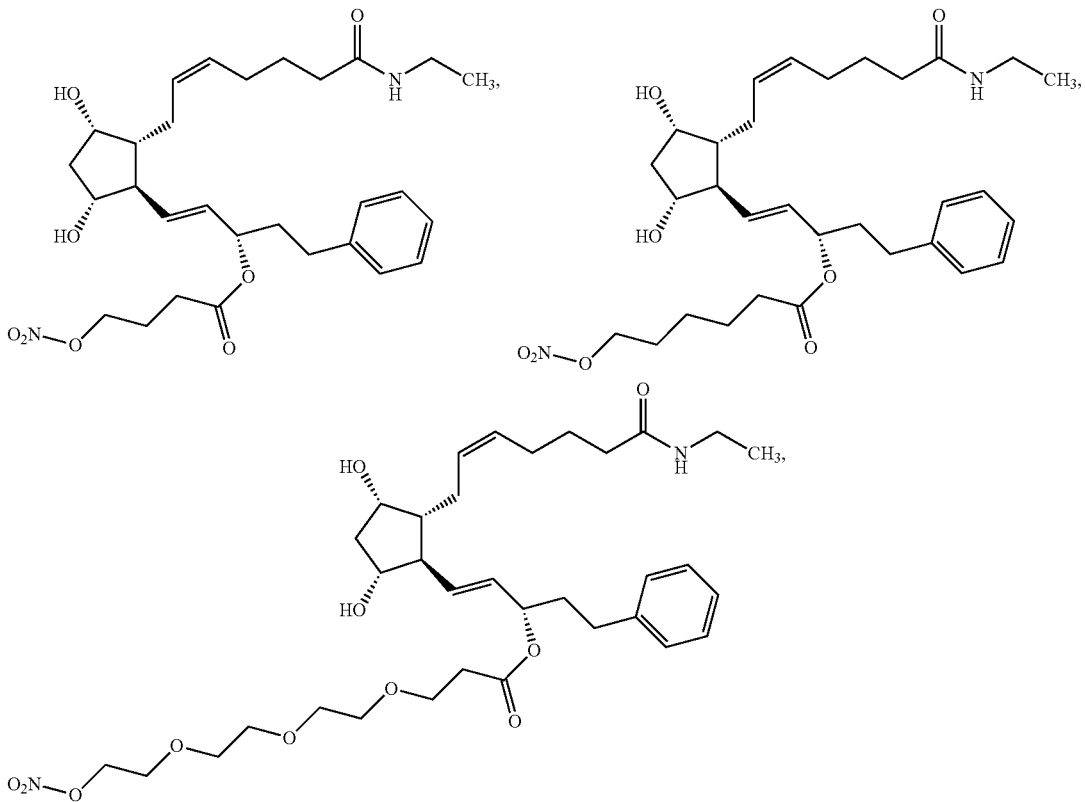

137 138
-continued
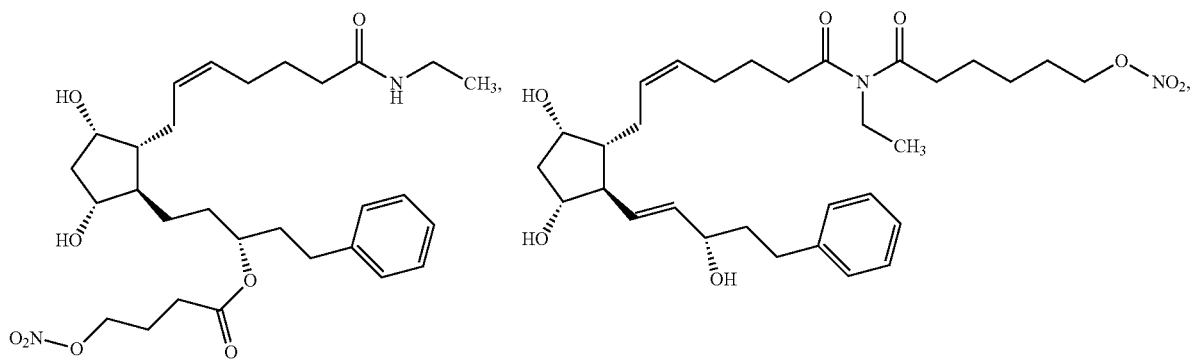
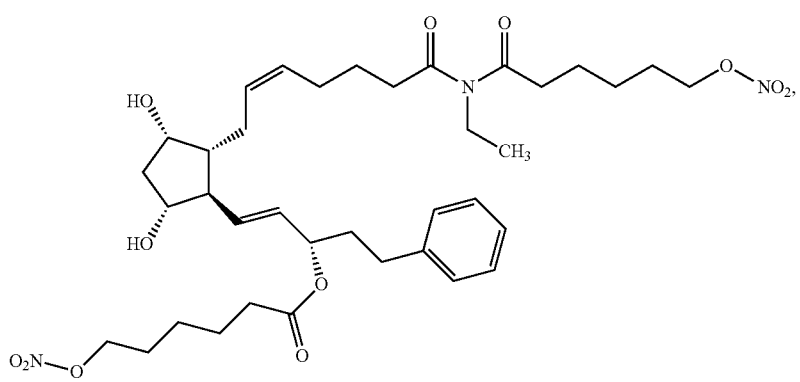
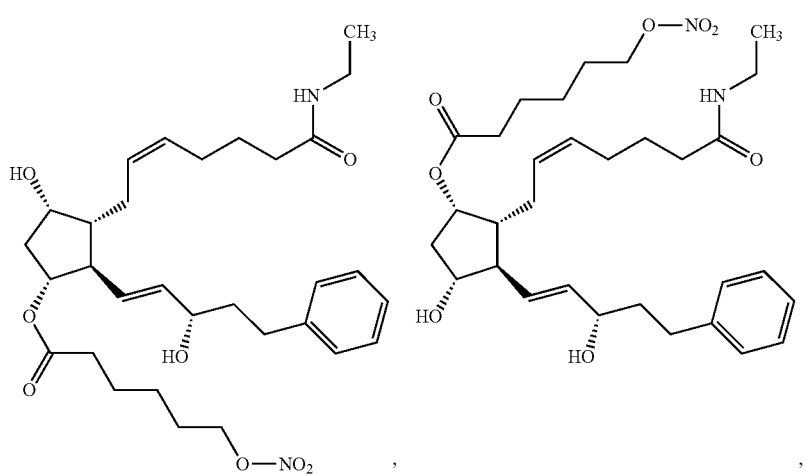

-continued
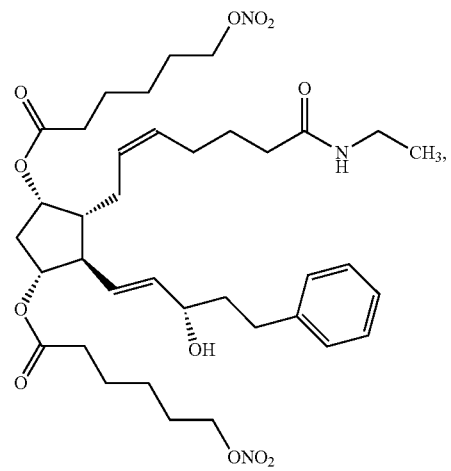
139
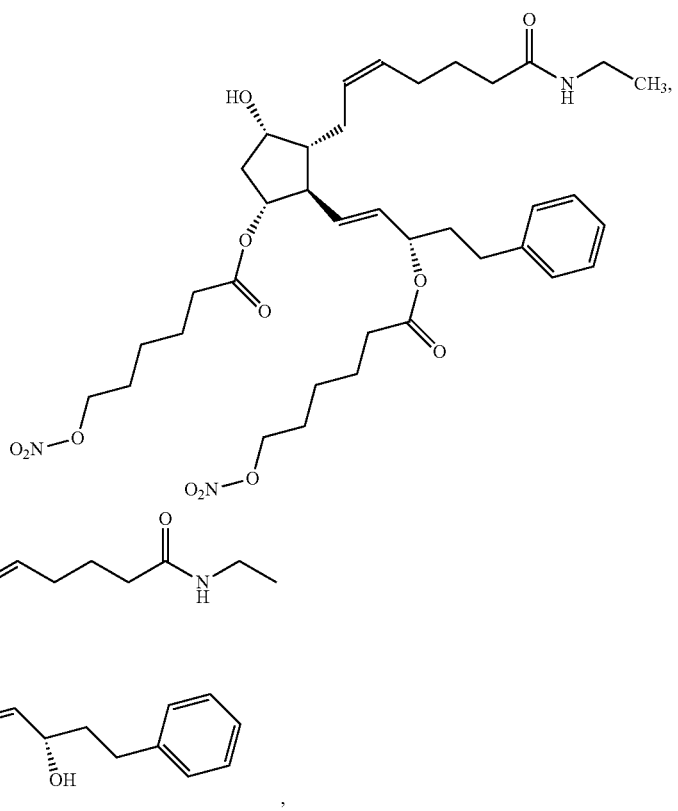
140
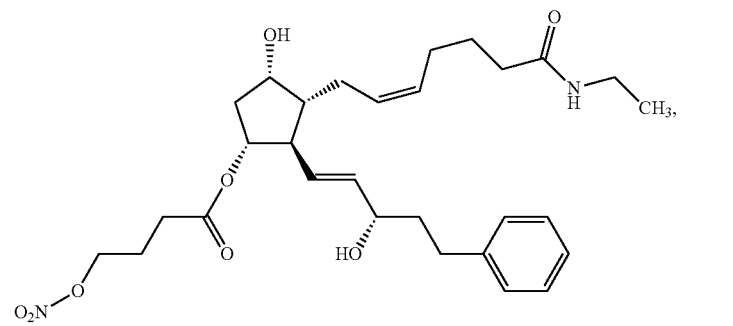
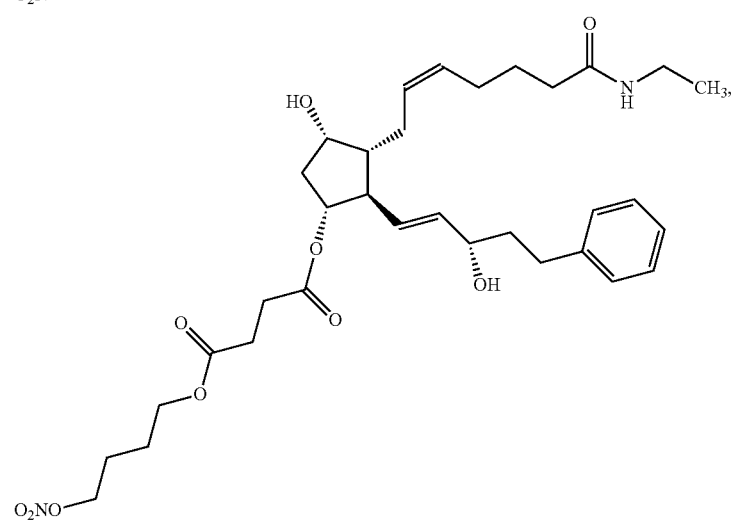

-continued
141
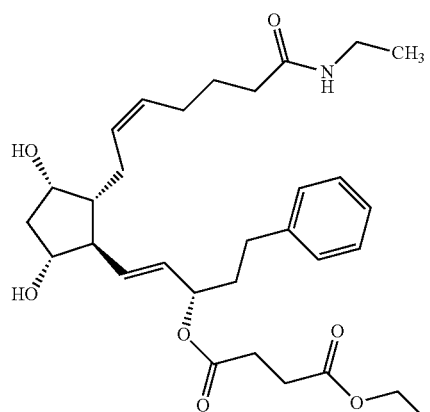
142
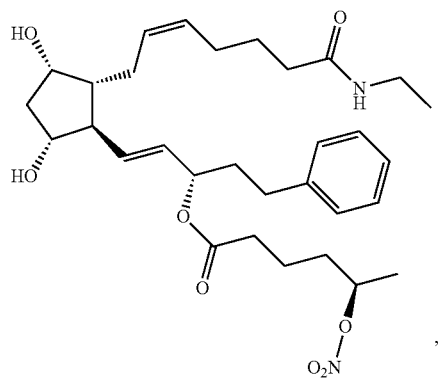
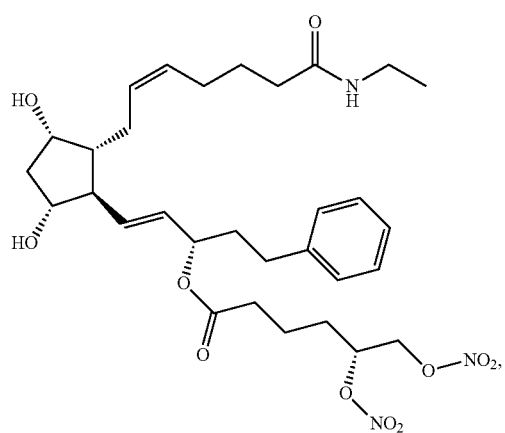
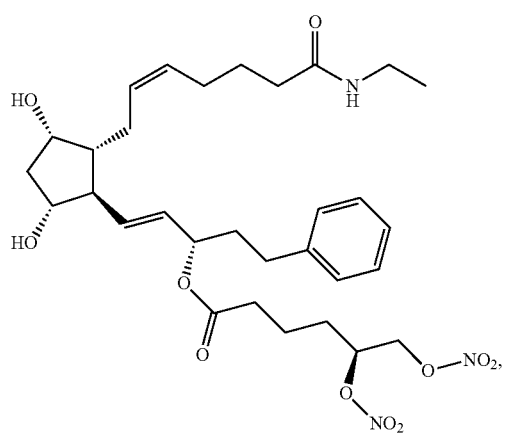
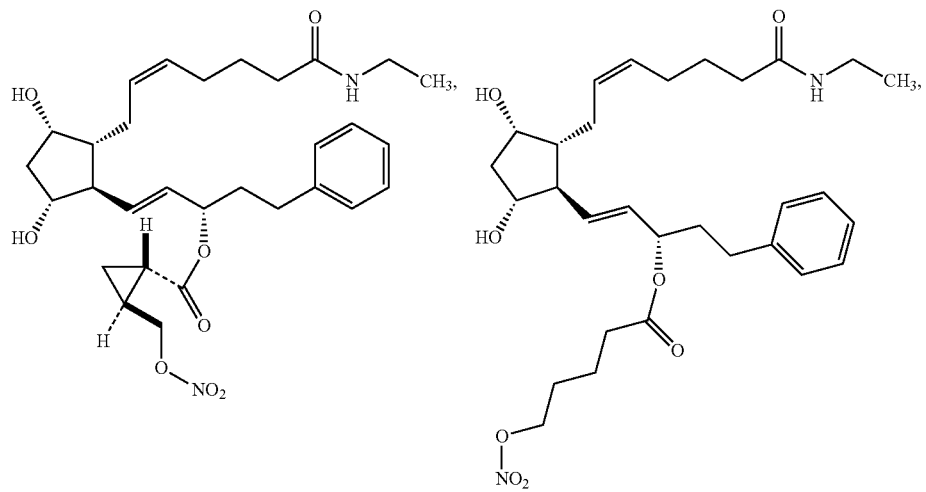

-continued
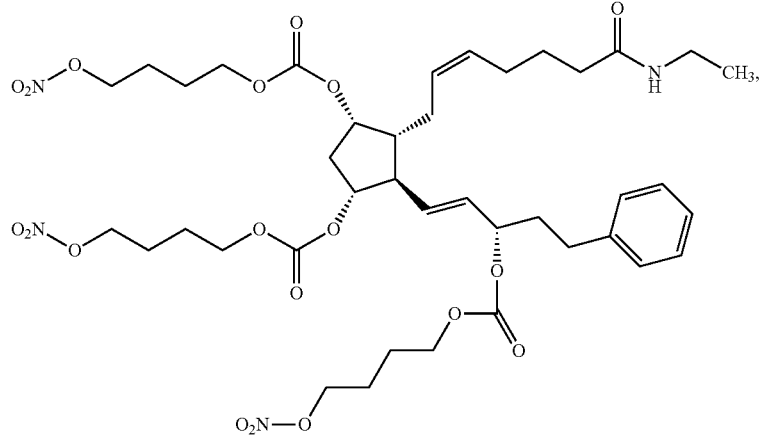
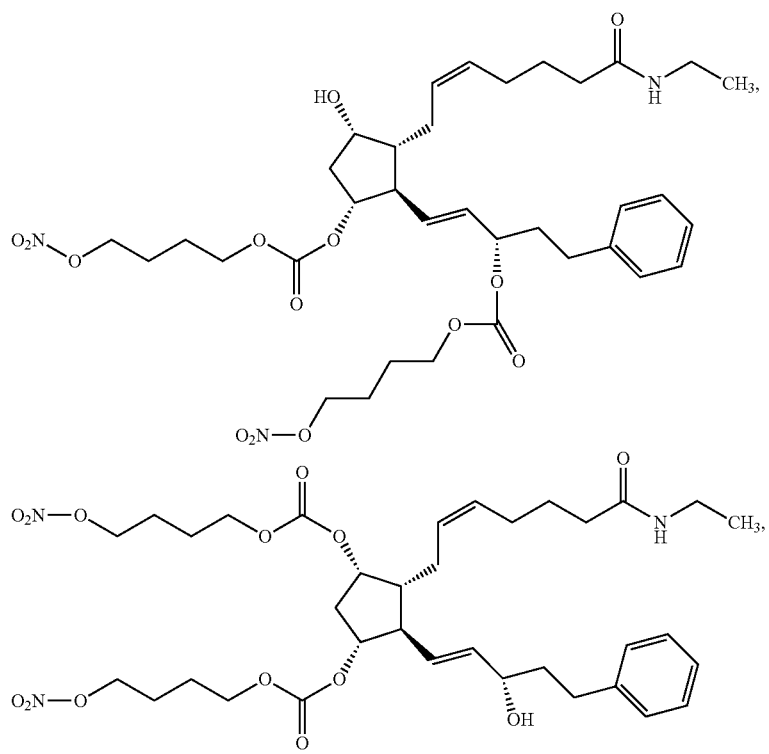
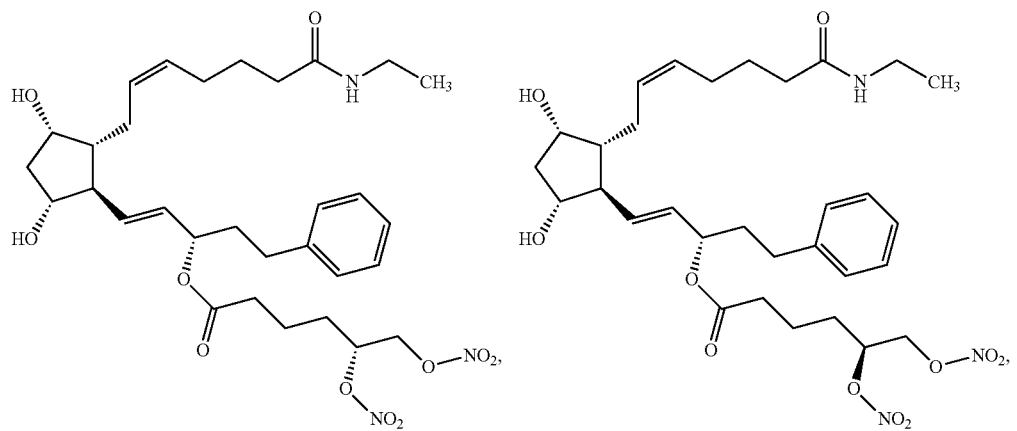

-continued

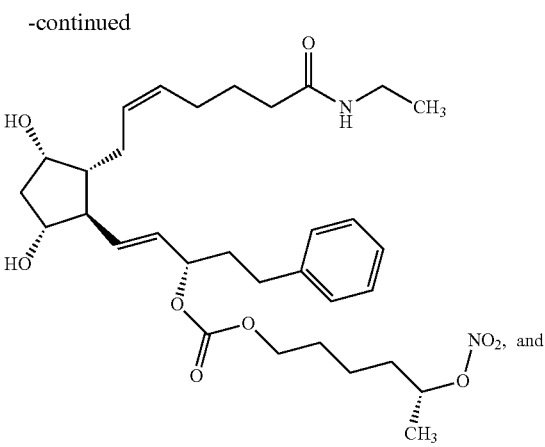
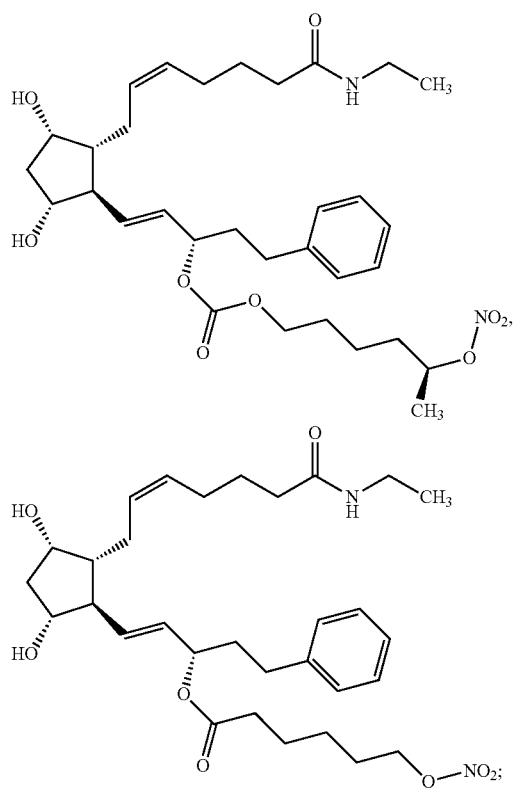

or a pharmaceutically acceptable salt or stereoisomer thereof.

15. A method for palliatively treating glaucoma and ocular hypertension comprising administering a compound of claim 1 and/or a pharmaceutically acceptable salt or stereoisomer thereof.

16. A pharmaceutical composition comprising a pharmaceutically acceptable carrier and a pharmaceutically effective amount of a compound and/or a salt or stereoisomer thereof as defined in claim 1.

17. A pharmaceutical composition according to claim 16 for the treatment of glaucoma and ocular hypertension.

18. A method for treating glaucoma or ocular hypertension comprising contacting an effective intraocular pressure reducing amount of a pharmaceutical composition according to claim 16 with the eye in order to reduce eye pressure and to maintain said pressure on a reduced level.

19. A pharmaceutical composition comprising a mixture of a compound and/or a salt or stereoisomer thereof as defined in claim 1 and:
  (i) a beta-blocker; or
  (ii) a carbonic anhydrase inhibitor; or
  (iii) an adrenergic agonist;
or a nitrooxy derivative of (i), (ii) or (iii).

* * * * *